United States Patent
Jadhav et al.

(10) Patent No.: US 8,722,901 B2
(45) Date of Patent: May 13, 2014

(54) CARBOXY OXAZOLE OR THIAZOLE COMPOUNDS AS DGAT-1 INHIBITORS USEFUL FOR THE TREATMENT OF OBESITY

(75) Inventors: Ravindra Dnyandev Jadhav, Mumbai (IN); Rajiv Sharma, Mumbai (IN); Kishorkumar Shivajirao Kadam, Mumbai (IN); Shivaji Sadashiv Kandre, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 0 days.

(21) Appl. No.: 13/505,917

(22) PCT Filed: Nov. 1, 2010

(86) PCT No.: PCT/IB2010/054930
§ 371 (c)(1),
(2), (4) Date: May 3, 2012

(87) PCT Pub. No.: WO2011/055289
PCT Pub. Date: May 12, 2011

(65) Prior Publication Data
US 2012/0214854 A1 Aug. 23, 2012

Related U.S. Application Data

(60) Provisional application No. 61/258,272, filed on Nov. 5, 2009.

(51) Int. Cl.
*A61K 31/426* (2006.01)
*A61K 31/421* (2006.01)
*C07D 277/30* (2006.01)
*C07D 263/32* (2006.01)

(52) U.S. Cl.
USPC ............ 548/236; 548/200; 514/365; 514/374

(58) Field of Classification Search
USPC .................................................. 548/200, 236
See application file for complete search history.

(56) References Cited

FOREIGN PATENT DOCUMENTS

| WO | 2004/100881 A2 | 11/2004 |
| WO | 2006/113919 A2 | 10/2006 |
| WO | 2007/137107 A2 | 11/2007 |
| WO | 2008/100423 A1 | 8/2008 |
| WO | 2010/023609 A1 | 3/2010 |

OTHER PUBLICATIONS

Chemical Abstract 147:250590, 2007.*
Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*

(Continued)

*Primary Examiner* — Laura L. Stockton
(74) *Attorney, Agent, or Firm* — Ladas & Parry LLP

(57) ABSTRACT

Heteroaryl compounds, processes for their preparation, pharmaceutical compositions containing them and their use in the treatment of diseases or disorders mediated by Diacylglycerol acyltransferase (DGAT) enzyme, particularly DGAT-1 is described.

29 Claims, No Drawings

(56) References Cited

OTHER PUBLICATIONS

King, Andrew J. et al, Diacylglycerol Acyltransferase 1 Inhibition Lowers Serum Triglycerides in the Zucker Fatty Rat the Hyperlipidemic Hamster. The Journal of Pharmacology and Experimental Therapeutics, 2009, 300 (2), 526-531.

Poirier, Paul et al, Obesity and Cardiovascular Disease: Pathophysiology, Evaluation, and Effect of Weight Loss. Circulation 2006, 113, 898-918.

Tomic, Martina, et al, Obesity—A Risk Factor for Microvascular and Neuropathic Complications in Diabetes? Diabetologia Croatica, 2003, 32-2, 73-78.

Poh, Z. X. et al, A Current Update on the Use of Alpha Lipoic Acid in management of Type 2 Diabetes Mellitus. Endocrine, Metabolic & Immune Disorders—Drug Targets, 2009, 9, 392-398.

Ottaviani, Monica, et al, Lipid Mediators in Acne. Mediators of Inflammation, 2010, Article ID 858176, 1-6.

Yen, Chi-Liang Eric et al, DGAT enzymes and triacylglycerol biosysnthesis. Journal of Lipid Research, 2008, 49 (11), 2283-2301.

Chen, Hubert C. et al, Inhibition of Triglyceride Synthesis as a Treatment Strategy for Obesity. Arteriosclerosis, Thrombosis, and Vascular Biology, 2005, 25, 482-486.

Villanueva, Claudio J. et al, Specific Role for Acyl COA:Diacylglycerol Acyltransferase 1 (Dgat1) in Hepatic Steatosis Due to Exogenous Fatty Acids. Hepatology, 2009, 50, 434-442.

* cited by examiner

CARBOXY OXAZOLE OR THIAZOLE COMPOUNDS AS DGAT-1 INHIBITORS USEFUL FOR THE TREATMENT OF OBESITY

This is a 371 application of PCT/IN2010/054930 filed on 1 Nov. 2010, entitled "CARBOXY OXAZOLE OR THIAZOLE COMPOUNDS AS DGAT 1 INHIBITORS USEFUL FOR THE TREATMENT OF OBESITY", which was published in the English language on 12 May 2011, with International Publication Number WO 2011/055289 A2, and which claims priority from U.S. Patent Application 61/258,272 filed 5 Nov. 2009.

FIELD OF THE INVENTION

The present invention relates to novel heteroaryl compounds, processes for their preparation, pharmaceutical compositions containing them and their use as medicaments, in particular to the use of these compounds for the treatment of diseases or disorders mediated by diacylglycerol acyltransferase (DGAT), particularly DGAT-1.

BACKGROUND OF THE INVENTION

Obesity, generally defined as a body mass index (BMI) of more than 30 kilogram per square meter ($Kg/m^2$), is a major health problem throughout the world. It is a risk factor for hypertension, diabetes and cardiovascular disease. Obesity is viewed as an energy storage disorder, resulting when energy input exceeds energy output. Most of the excess calories are stored as fat (more than 95% of fat is triglyceride) in the adipose tissue leading to obesity, and when stored in non-adipose tissue it leads to insulin resistance. Hence, inhibition of triglyceride synthesis represents a potential therapeutic strategy for human obesity and type 2 diabetes.

Metabolic syndrome, also known as Syndrome-X, is characterized by increased body weight, altered glucose homeostasis with insulin resistance, elevated plasma triglyceride levels and low-density lipoprotein-cholesterol, high blood pressure, and increased risk of cardiovascular morbidity and mortality. The prevalence of metabolic syndrome has risen dramatically in the US and rest of the world. In the US, metabolic syndrome affects roughly 25% of adults over the age of 20 years and up to 45% of the population over the age of 50 years (*JAMA*, 287, 356-359 (2002)). The currently available therapies for addressing the disorders associated with metabolic syndrome are far from satisfactory.

A key enzyme in the synthesis of triglycerides is acylCoA: diacylglycerol acyltransferase (DGAT). Genes for two DGAT enzymes, DGAT-1 and DGAT-2 have been identified. Both DGAT-1 and DGAT-2 are highly expressed in tissues that are active in triglyceride synthesis such as white adipose tissue (WAT), intestine, liver, skeletal muscle and mammary gland (*Proc. Natl. Acad. Sciences U.S.A.*, 95, 13018-13023 (1998)); *J. Biol. Chem.*, 276, 38870-38876 (2001)).

Studies in experimental animals suggest that inhibiting or reducing the activity of the DGAT-1 enzyme results in resistance to the development of obesity, diabetes and associated complications. DGAT-1 knockout studies in mice have shown that these mice are viable and resistant to obesity (*Nat. Genet.*, 25, 87-90 (2000)), whereas DGAT-2 knockout mice die soon after birth as there is no stored form of energy source due to lack of adipose tissues (*J. Biol. Chem.*, 279, 11767-11776 (2004)). In contrast to DGAT-2 knockout mice, DGAT-1 knockout mice are viable and are resistant to diet-induced obesity and steatosis. In addition, these mice are more sensitive to insulin and leptin (*J. Clin. Invest.*, 109, 1049-1055 (2002)). Heterozygous DGAT-1 knockout mice are also resistant to obesity (*Thromb. Vasc. Biol.*, 25, 482-486 (2005)); *Nutr. Metab (Lond.)*, 3, 10 (2006)). These studies together suggest that DGAT-2 plays a fundamental role in triglyceride synthesis and is essential for survival, whereas DGAT-1 contributes to triglyceride synthesis and plays an important role in regulating energy metabolism.

Additional studies with DGAT-1 antisense oligonucleotides indicate that inhibition of DGAT-1 results in decrease in blood glucose in ob/ob mice. Thus, resistance to obesity due to increased energy expenditure and reduced energy absorption along with an apparent improvement in insulin sensitivity associated with DGAT-1 deficiency suggests that inhibition of DGAT-1 could be a potential treatment strategy for addressing metabolic syndrome.

One target that has received much attention for treatment of metabolic syndrome is the DGAT-1 enzyme (*Trends Cardiovasc. Medicine*, 10, 188-192 (2000)); *Curr. Drug Targets Immune Endocr. Metabol. Disorders*, 3, 263-270 (2003)).

DGAT-1 inhibitors may also find use in the treatment of Hepatitis C infection *Nature Medicine* (10 Oct. 2010)

The following patent publications describe compounds that inhibit DGAT-1 activity:

WO2004/100881 and WO2006/044775 describe biphenyl-4-yl-carbonyl amino acid derivatives, WO2006/019020 describes substituted ureas, WO2006/134317 describes oxadiazole derivatives, WO2006/019020 describes substituted ureas, WO2009/071483 describes indazol-5-yl-ureas, WO2006/113919 and US 2004/0224997 describe aryl alkyl acid, and JP2004-67635 describes thiazoleamido substituted phenyl compounds.

WO 2007/087429 describes phenyl and pyridyl compounds for inflammation and immune related uses.

WO 2008/154601 describes compounds, composition and methods for treating viral infections mediated by virus in the Flaviviridae family of viruses.

SUMMARY OF THE INVENTION

According to one aspect of the present invention, there is provided a compound of formula (I) (as described herein below).

According to another aspect of the present invention, there is provided a method of inhibition of DGAT-1 in a subject, comprising administering to the subject in need of such treatment, a therapeutically effective amount of a compound of formula (I) or a pharmaceutically acceptable salt thereof.

According to another aspect of the present invention, there is provided a method for the treatment of obesity and obesity related disorders comprising administering to the subject in need of such treatment a therapeutically effective amount of a compound of formula (I) or a pharmaceutically acceptable salt thereof.

According to another aspect of the present invention, there is provided a method for the treatment of obesity, diabetes, insulin resistance or impaired glucose tolerance comprising administering to the subject in need of such treatment a therapeutically effective amount of a compound of formula (I) or a pharmaceutically acceptable salt thereof.

According to yet another aspect of the present invention, there is provided a compound of formula (I) for use in the treatment of obesity and obesity related disorders.

According to yet another aspect of the present invention, there is provided a compound of formula (I) for use in the treatment of diabetes, obesity, insulin resistance or impaired glucose tolerance.

According to another aspect of the present invention, there is provided a pharmaceutical composition, comprising a compound of the formula (I) or a pharmaceutically acceptable salt thereof and a pharmaceutically acceptable carrier, vehicle, diluent or excipient.

According to another aspect of the present invention, there is provided a process for the preparation of a pharmaceutical composition, comprising bringing a compound of formula (I) into association with a pharmaceutically acceptable excipient or carrier.

According to another aspect of the present invention, there is provided a process for the preparation of a compound of formula (I).

DETAILED DESCRIPTION OF THE INVENTION

The present invention provides a compound of formula (I),

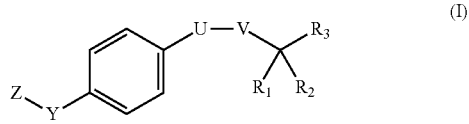

and stereoisomers thereof and tautomers thereof and prodrugs thereof and pharmaceutically acceptable salts and solvates thereof, wherein,

- Z is selected from unsubstituted or substituted alkylcycloalkyl, unsubstituted or substituted cycloalkyl, unsubstituted or substituted aryl, unsubstituted or substituted heteroaryl and unsubstituted or substituted heterocycle, wherein each of substituted alkylcycloalkyl, cycloalkyl, aryl, heteroaryl and heterocycle is substituted with one or more substituents selected from $R^a$;
- $R^a$ at each occurrence is selected from halogen, oxo, thio, nitro, —CN, —$OR_x$, —$S(=O)_mR_x$, —$S(=O)_nNR_1R_2$, —$OCOR_x$, —$SCOR_x$, —$NR_xR_y$, —$NR_xCOR_y$, —$NR_x$-$COOR_y$, —$NR_xSOR_y$, —$NR_xSO_2R_y$, —$NR_xCONR_xR_y$, —$COR_x$, —$COOR_x$, —$CONR_xR_y$, —$(CR_xR_y)_n$—$OR_x$, alkyl, haloalkyl, alkenyl, alkynyl, cycloalkyl, alkylcycloalkyl, aryl, alkylaryl, heterocyclyl, alkylheterocyclyl, heteroaryl and alkylheteroaryl; wherein $R_x$ and $R_y$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl; said alkyl, haloalkyl, alkenyl, alkynyl, cycloalkyl, alkylcycloalkyl, aryl, alkylaryl, heterocyclyl, alkylheterocyclyl, heteroaryl and alkylheteroaryl are optionally substituted with $R^b$;
- $R^b$ at each occurrence is selected from halogen, nitro, —CN, hydroxy, alkoxy, —COOH, —$NH_2$ and alkyl;
- Y is selected from —$(CH_2)$—$N(R_4)$—, —$N(R_4)$—, —$N(R_4)CON(R_5)$—, —$N(R_4)CSN(R_5)$—, —$N(R_4)(C=NR_4)N(R_5)$—, —$NR_4C(O)$—, —$CONR_4$—, —$NR_4SO_2$— and —$SO_2NR_4$—;
- U is selected from

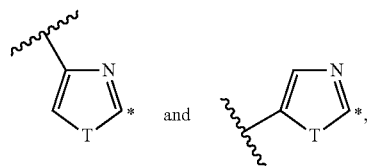

wherein T is —O— or —S—;
- V is selected from —$CONR_4$—, —$CSNR_4$—, —C(O), —C(S)—, —$COC(R_4)(R_5)$ and —$SO_2NR_4$;
- $R_3$ is selected from —$COOR_p$, —$CONR_pR_q$, —$CONR_pSO_2R_q$ and a carboxylic acid isostere such as tetrazol-5-yl, 5-trifluoromethyl-1,2,4-triazol-3-yl, 5-(methylsulfonyl)-1,2,4-triazol-3-yl, and 2,5-dihydro-5-oxo-1,2,4-oxadiazol-3-yl;
- $R_1$, $R_2$, $R_4$ and $R_5$ at each occurrence are independently selected from H and unsubstituted or substituted alkyl wherein substituted alkyl is substituted with substituents selected from $R^a$;
- $R_p$ and $R_q$ are independently selected from H, unsubstituted or substituted alkyl, unsubstituted or substituted aryl, unsubstituted or substituted heterocyclyl, unsubstituted or substituted heteroaryl, wherein each of substituted alkyl, aryl, heterocycle and heteroaryl is substituted with one or more substituents selected from $R^a$;
- or $R_1$ and $R_2$ together with the carbon to which they are attached form a three- to six-membered carbocylic ring, wherein the ring may be optionally substituted with one or more substituents selected from $R^a$;
- m is an integer from 0 to 2;
- n is an integer from 1 to 2;
- * indicates the point of attachment to —V— and

indicates the point of attachment to phenyl ring.

Definitions

Listed below are definitions, which apply to the terms as they are used throughout the specification (unless they are limited in specific instances).

It will be understood that "substitution" or "substituted with" includes the implicit proviso that such substitution is in accordance with permitted valence of the substituted atom and the substituent, as well as represents a stable compound, which does not readily undergo transformation such as rearrangement, cyclization, elimination, etc.

The term "halogen" denotes an atom selected from F, Cl, Br and I.

As used herein, the term "alkyl" refers to a saturated aliphatic group, including straight or branched-chain alkyl groups containing 1 to 10 carbon atoms, suitably 1 to 6 carbon atoms, preferably 1 to 4 carbon atoms. Examples of alkyl groups include but are not limited to methyl, ethyl, propyl, butyl, isopropyl, isobutyl, 1-methylbutyl, isopentyl, neopentyl, 2,2-dimethylbutyl, 2-methylpentyl, 3-methylpentyl, sec-butyl, tert-butyl and the like.

The term "alkenyl" refers to an unsaturated, branched or straight chain alkyl group having from 2 to 10 carbon atoms, suitably 2 to 6 carbon atoms, preferably 2 to 4 carbon atoms, and at least one carbon-carbon double bond (two adjacent $sp^2$ carbon atoms). Depending on the placement of double bond and substituents if any, the geometry of the double bond may be entgegen (E), or zusammen (Z), cis or trans. Examples of alkenyl include but are not limited to ethenyl, propenyl, 2-propenyl, cis-2-butenyl, trans-2-butenyl, 2-methyl-2-propenyl, pent-2-enyl, 2-isopentenyl and the like.

The term "alkynyl" refers to an unsaturated, branched or straight chain alkyl group having from 2 to 10 carbon atoms, suitably 2 to 6 carbon atoms, preferably 2 to 4 carbon atoms, and at least one carbon-carbon triple bond (two adjacent sp carbon atoms). Examples of alkynyl include but are not limited to ethynyl, 1-propynyl, 3-propynyl, 3-butynyl and the like.

As used herein, the term "haloalkyl" refers to an alkyl group in which one or more hydrogen atoms are replaced by one or more halogen atoms. "Halo-$C_1$-$C_8$ alkyl" groups have 1 to 8 carbon atoms, "halo-$C_1$-$C_6$ alkyl" groups have 1 to 6 carbon atoms. Examples of haloalkyl include, but are not limited to, mono-, di- or tri-fluoromethyl; mono-, di- or tri-chloromethyl; mono-, di-, tri-, tetra- or pentafluoroethyl; heptafluoropropyl; difluorochloromethyl and dichlorofluoromethyl.

The term "alkoxy" refers to —O-alkyl, where alkyl is as defined above.

The term "cycloalkyl" refers to a saturated or partially unsaturated cyclic hydrocarbon group including a mono-, bi- or poly-cyclic ring system and including a total of 3 to 20 ring carbon atoms. Examples of cycloalkyl include but are not limited to cyclopropyl, cyclobutyl, cyclopentyl, cyclohexyl, adamantyl, [3,3,0]bicyclooctanyl-, [4,4,0]bicyclodecanyl and the like. A poly-cyclic cycloalkyl ring system may include cyclic hydrocarbon group fused to an aryl group such as indanyl, tetrahydronaphthyl and the like. The cycloalkyl ring system may be bonded via any desired position. A poly-cyclic cycloalkyl ring system may be bonded via $sp^a$ carbon or $sp^2$ carbon.

The term "aryl" refers to a monocyclic or polycyclic hydrocarbon group having up to 20 ring carbon atoms, preferably up to 10 ring carbon atoms, in which at least one carbocyclic ring is present that has a conjugated π electron system. Examples of aryl include but are not limited to phenyl, naphthyl and the like.

The term "alkylaryl" refers to an aryl group bonded through an alkyl, wherein the terms "alkyl" and "aryl" are as defined herein above. Examples of alkylaryl include but are not limited to benzyl, 1-naphthyl ethyl, 1-phenyl ethyl and the like.

The term "alkylcycloalkyl" refers to a cycloalkyl group bonded through an alkyl group, wherein the terms "alkyl" and "cycloalkyl" are as defined herein above.

The term "heterocyclyl" or "heterocycle" refers to a saturated or partially unsaturated monocyclic or polycyclic ring system containing 5 to 20 ring atoms of which 1, 2, 3 or 4 are identical or different heteroatoms selected from N, O and S. The "heterocyclyl" or "heterocycle" may, for example, have 1 or 2 oxygen atoms and/or 1 or 2 sulfur atoms and/or 1 to 4 nitrogen atoms in the ring. The, "heterocyclyl" or "heterocycle" preferably is a 5- or 6-membered ring. The ring heteroatoms can be present in any position with respect to each other provided that the resulting "heterocyclyl" or "heterocycle" is stable. Examples of "heterocyclyl" or "heterocycle" include but are not limited to: azocinyl, chromanyl, decahydroquinolinyl, furazanyl, imidazolidinyl, indolinyl, isobenzofuranyl, isoindolinyl, isooxazolinyl, morpholinyl, octahydroisoquinolinyl, oxazolidinyl, piperidinyl, piperazinyl, pyranyl, benzopyranyl, pyrazolinyl, pyrazolidinyl, pyrrolidinyl, pyrrolinyl, 4H-quinolizinyl, tetrahydrofuranyl, benzodioxolyl, tetrahydroisoquinolinyl, tetrahydroquinolinyl, 6H-1,2,5-thiadiazinyl and xanthenyl.

The term "alkylheterocycle" refers to a heterocycle group bonded through an alkyl, wherein the terms "alkyl" and "heterocycle" are as defined herein above.

The term "heteroaryl" as used herein refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. The rings may contain from 1 to 4 heteroatoms selected from N, O and S, wherein the N or S atom is optionally oxidized, or the N atom is optionally quaternized. Any suitable ring position of the heteroaryl moiety may be covalently linked to the defined chemical structure. Examples of heteroaryl include but are not limited to: furan, thiophene, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl, and the like.

The term "alkylheteroaryl" refers to a heteroaryl group bonded through an alkyl, wherein the terms "alkyl" and "heteroaryl" are as defined herein above.

As used herein, the term "solvate" preferably refers to a compound formed by the interaction of a solute (in this invention, a compound of formula (I) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Examples for suitable solvates are the mono- or dihydrates or alcoholates of the compounds according to the invention.

As used herein, the term "stereoisomer" is a general term used for all isomers of individual compounds that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers). The compounds of the present invention may have asymmetric centers and occur as racemates, racemic mixtures, individual diastereoisomers, or enantiomers, or may exist as geometric isomers, with all isomeric forms of said compounds being included in the present invention.

As used herein, the term "tautomer" refers to the coexistence of two (or more) compounds that differ from each other only in the position of one (or more) mobile atoms and in electron distribution, for example, keto-enol tautomers.

The term "pharmaceutically acceptable salts" refers to the non-toxic, inorganic and organic acid addition salts and base addition salts of compounds of the present invention.

As used herein, the terms "treatment" and "therapy" and the like refer to alleviate, slow the progression, prophylaxis, attenuation or cure of existing disease (e.g., diabetes or obesity).

As used herein the term "prodrug" refers to a compound that is a drug precursor, which, following administration into or onto the body, releases the drug in vivo via a chemical or physiological process, e.g., a prodrug on being brought to physiological pH or through an enzyme action is converted to the desired drug form. Various forms of prodrugs are known in the art and further information is discussed in Pro-drugs as Novel Delivery Systems, Vol. 14, ACS Symposium Series (T. Higuchi and W. Stella), Bioreversible Carriers in Drug Design, Pergamon Press, 1987 (Ed. E. B. Roche, American Pharmaceutical Association) and Design of Prodrugs, Elsevier 1985, (edited by H. Bundgaard). Exemplary prodrugs include esters of carboxylic acids such as methyl and ethyl esters. Pharmaceutically acceptable esters can be converted under physiological conditions to the carboxylic acid of formula (I).

As used herein the term "pharmaceutically acceptable" is meant that the carrier, diluent, excipients, and/or salt must be compatible with the other ingredients of the formulation, and not deleterious to the recipient thereof.

Embodiments

One embodiment of the present invention is a compound of formula I, wherein Z is selected from unsubstituted or substituted alkylcycloalkyl, unsubstituted or substituted cycloalkyl, unsubstituted or substituted aryl and unsubstituted or substituted heteroaryl.

Another embodiment is a compound of formula I, wherein Z is unsubstituted or substituted alkylcycloalkyl.

Another embodiment is a compound of formula I, wherein Z is ethylcyclohexyl.

Another embodiment is a compound of formula I, wherein Z is unsubstituted or substituted cycloalkyl.

Another embodiment is a compound of formula I, wherein Z is cycloalkyl substituted with one or more halogen.

Another embodiment is a compound of formula I, wherein Z is selected from indanyl and 4,4-difluorocyclohexyl.

Another embodiment is a compound of formula I, wherein Z is unsubstituted or substituted aryl.

Yet another embodiment is a compound of formula I, wherein Z is unsubstituted or substituted phenyl.

Yet another embodiment is a compound of formula I, wherein Z is phenyl substituted with one or more groups selected from haloalkyl, halogen, aryl, —$OR_x$ and alkyl; wherein alkyl is optionally substituted with one or more halogen or cyano groups and $R_x$ is aryl.

Another embodiment is a compound of formula I, wherein Z is unsubstituted or substituted heteroaryl.

Yet another embodiment is a compound of formula I, wherein Z is heteroaryl substituted with alkyl or halogen.

Yet another embodiment is a compound of formula I, wherein Z is selected from unsubstituted or substituted benzothiazolyl and unsubstituted or substituted pyridyl, wherein the substituent is fluoro or alkyl.

Yet another embodiment is a compound of formula I, wherein Z is selected from 6-fluoro-benzothiazol-2-yl and 5-butyl-pyridin-2-yl.

Yet another embodiment is a compound of formula I, wherein Z is selected from ethylcyclohexyl, indanyl, 4,4-difluorocyclohexyl, phenyl, 4-fluorophenyl, 4-(2-cyanopropan-2-yl)phenyl, 4-(3-cyanopentan-3-yl)phenyl, 3-trifluoromethylphenyl, 4-trifluoromethylphenyl, 2-chlorophenyl, 3-chlorophenyl, 4-chlorophenyl, 4-chloro-2-fluorophenyl, 4-chloro-2-phenoxyphenyl, 2-chloro-4-trifluoromethylphenyl, 3,4-dimethylphenyl, 2,4-dichlorophenyl, 2-phenoxyphenyl, 4-tert-butylphenyl, 4-pentylphenyl, biphenyl, 6-fluorobenzothiazol-2-yl and 5-butyl-pyridin-2-yl.

Another embodiment is a compound of formula I, wherein Y is selected from —$N(R_4)$—, —$N(R_4)CON(R_5)$—, —$N(R_4)C(O)$—, —$(CH_2)$—$N(R_4)$—, —$CON(R_4)$— and —$SO_2N(R_4)$— wherein $R_4$ and $R_5$ are independently selected from H and unsubstituted alkyl.

Another embodiment is a compound of formula I, wherein Y is selected from —NH—, —NHCONH—, —$CH_2$—N($CH_2$-Phenyl)-, —$CH_2$—NH—, —CONH— and —$SO_2$NH—.

Another embodiment is a compound of formula I, wherein U is,

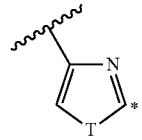

wherein T is —O— or —S—.

Yet another embodiment is a compound of formula I, wherein U is,

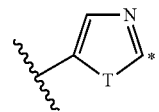

wherein T is —O— or —S—.

Another embodiment is a compound of formula I, wherein V is —$CON(R_4)$—.

Another embodiment is a compound of formula I, wherein $R_4$ is selected from H and unsubstituted alkyl.

Another embodiment is a compound of formula I, wherein V is selected from —CONH— and —$CON(CH_3)$—.

Another embodiment is a compound of formula I, wherein $R_1$ and $R_2$ are independently selected from H and unsubstituted or substituted alkyl.

Another embodiment is a compound of formula I, wherein $R_1$ and $R_2$ are independently selected from H and isopropyl.

Another embodiment is a compound of formula I, wherein $R_3$ is —$COOR_p$.

Another embodiment is a compound of formula I, wherein $R_p$ is H or alkyl.

Another embodiment is a compound of formula I, wherein $R_3$ is selected from —COOH and —$COOCH_3$.

Another embodiment is a compound of formula I, wherein Z is selected from unsubstituted or substituted alkylcycloalkyl, unsubstituted or substituted cycloalkyl, unsubstituted or substituted aryl, unsubstituted or substituted heteroaryl and unsubstituted or substituted heterocycle, wherein each of substituted alkylcycloalkyl, cycloalkyl, aryl, heteroaryl and heterocycle is substituted with one or more substituents selected from $R^a$;

$R^a$ at each occurrence is selected from halogen, nitro, —CN, —$OR_x$, —$S(=O)_m R_x$, —$S(=O)_n NR_1 R_2$, —$NR_x R_y$, —$NR_x COR_y$, —$NR_x SOR_y$, —$NR_x SO_2 R_y$, —$NR_x CONR_x R_y$, —$COOR_x$, —$CONR_x R_y$, —$(CR_x R_y)_n$ —$OR_x$, haloalkyl, aryl, heteroaryl and alkyl; wherein alkyl is optionally substituted with one or more halogen or cyano groups, and $R_x$ and $R_y$ are independently selected from H, alkyl and aryl;

Y is selected from —(CH$_2$)—N(R$_4$)—, —N(R$_4$)—, —N(R$_4$)CON(R$_5$)—, —NR$_4$C(O)—, —CON(R$_4$)—, —N(R$_4$)SO$_2$— and —SO$_2$N(R$_4$)—;

U is selected from

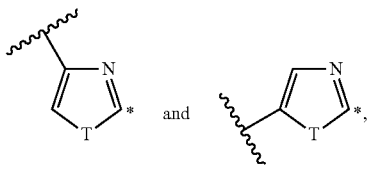

wherein T is —O— or —S—;

V is —CONR$_4$—;

R$_1$, R$_2$, R$_4$ and R$_5$ at each occurrence are independently selected from H and unsubstituted alkyl;

R$_3$ is selected from —COOR$_p$ and a carboxylic acid isostere such as tetrazol-5-yl, 5-trifluoromethyl-1,2,4-triazol-3-yl, 5-(methylsulfonyl)-1,2,4-triazol-3-yl and 2,5-dihydro-5-oxo-1,2,4-oxadiazol-3-yl; wherein R$_p$ is selected from H and unsubstituted or substituted alkyl;

m is an integer from 0 to 2; n is an integer from 1 to 2;

* indicates the point of attachment to —V— and

indicates the point of attachment to phenyl ring.

Another embodiment is a compound of formula I, wherein Z is selected from unsubstituted or substituted alkylcycloalkyl, unsubstituted or substituted cycloalkyl, unsubstituted or substituted aryl and unsubstituted or substituted heteroaryl wherein each of substituted alkylcycloalkyl, cycloalkyl, aryl, heteroaryl and heterocycle is substituted with one or more substituents selected from halogen, —OR$_x$, haloalkyl, aryl and unsubstituted alkyl or alkyl substituted with one or more substituents selected from halogen and cyano; R$_x$ is selected from H, alkyl and aryl;

Y is selected from —(CH$_2$)—N(R$_4$)—, —N(R$_4$)—, —N(R$_4$)CON(R$_5$)—, —NR$_4$C(O)—, —CON(R$_4$)—, —N(R$_4$)SO$_2$— and —SO$_2$NR$_4$—;

U is selected from

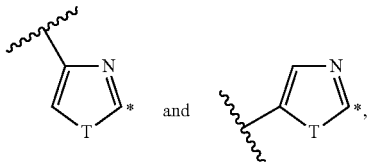

wherein T is —O— or —S—;

V is —CON(R$_4$)—;

R$_1$, R$_2$, R$_4$ and R$_5$ at each occurrence are independently selected from H and unsubstituted alkyl and R$_3$ is selected from —COOR$_p$ and a carboxylic acid isostere such as tetrazol-5-yl, 5-trifluoromethyl-1,2,4-triazol-3-yl, 5-(methylsulfonyl)-1,2,4-triazol-3-yl and 2,5-dihydro-5-oxo-1,2,4-oxadiazol-3-yl; wherein R$_p$ is selected from H and unsubstituted alkyl;

* indicates the point of attachment to —V— and

indicates the point of attachment to phenyl ring.

Another embodiment is a compound of formula I, wherein Z is selected from unsubstituted or substituted alkylcycloalkyl, unsubstituted or substituted cycloalkyl, unsubstituted or substituted aryl and unsubstituted or substituted heteroaryl wherein each of substituted alkylcycloalkyl, cycloalkyl, aryl, heteroaryl and heterocycle is substituted with one or more substituents selected from halogen, haloalkyl, —OR$_x$, aryl and unsubstituted alkyl or alkyl substituted with one or more substituents selected from halogen and cyano; R$_x$ is selected from H, alkyl and aryl;

Y is selected from —CH$_2$—NH—, —NH—, —NH-CONH—, —NHC(O)—, —CON(H)—, —NHSO$_2$— and —SO$_2$NH;

U is selected from

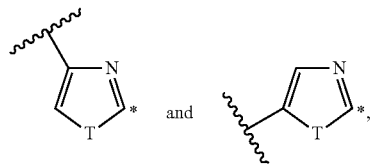

wherein T is —O— or —S—;

V is —CONR$_4$—;

R$_1$, R$_2$, R$_4$ and R$_5$ at each occurrence are independently selected from H and unsubstituted alkyl and R$_3$ is selected from —COOR$_p$ and a carboxylic acid isostere such as tetrazol-5-yl, 5-trifluoromethyl-1,2,4-triazol-3-yl, 5-(methylsulfonyl)-1,2,4-triazol-3-yl, and 2,5-dihydro-5-oxo-1,2,4-oxadiazol-3-yl; wherein R$_p$ is selected from H and unsubstituted alkyl;

* indicates the point of attachment to —V— and

indicates the point of attachment to phenyl ring.

Another embodiment is a compound of formula I, wherein Z is selected from unsubstituted or substituted alkylcycloalkyl, unsubstituted or substituted cycloalkyl, unsubstituted or substituted aryl and unsubstituted or substituted heteroaryl wherein each of substituted alkylcycloalkyl, cycloalkyl, aryl, heteroaryl and heterocycle is substituted with one or more substituents selected from R$^a$;

R$^a$ at each occurrence is selected from halogen, nitro, —CN, —OR$_x$, —S(=O)$_m$R$_x$, —S(=O)$_n$NR$_1$R$_2$, —NR$_x$R$_y$, —NR$_x$COR$_y$, —NR$_x$SOR$_y$, —NR$_x$SO$_2$R$_y$, —NR$_x$CONR$_x$R$_y$, —COOR$_x$, —CONR$_x$R$_y$, —(CR$_x$R$_y$)$_n$—OR$_x$, haloalkyl, aryl, heteroaryl and alkyl; wherein alkyl is optionally substituted with one or more halogen or cyano groups, and $R_x$ and $R_y$ are independently selected from H, alkyl and aryl;

Y is selected from —CH₂—NH—, —CH₂—N(CH₂-Phenyl)-, —NH—, —NHCONH—, —NHC(O)—, —CON(H)—, —NHSO₂— and —SO₂NH;

U is selected from

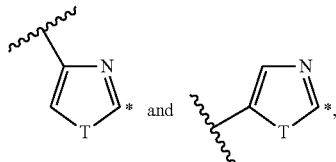

wherein T is —O— or —S—;

V is —CONR₄—;

$R_1$, $R_2$, $R_4$ and $R_5$ at each occurrence are independently selected from H and unsubstituted alkyl and $R_3$ is selected from —COOR$_p$ and a carboxylic acid isostere such as tetrazol-5-yl, 5-trifluoromethyl-1,2,4-triazol-3-yl, 5-(methylsulfonyl)-1,2,4-triazol-3-yl, and 2,5-dihydro-5-oxo-1,2,4-oxadiazol-3-yl; wherein $R_p$ is selected from H and unsubstituted alkyl;

m is an integer from 0 to 2; n is an integer from 1 to 2;

* indicates the point of attachment to —V— and

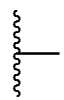

indicates the point of attachment to phenyl ring.

Another embodiment is a compound of formula I, wherein Z is selected from ethylcyclohexyl, indanyl, 4,4-difluorocyclohexyl, phenyl, 4-fluorophenyl, 4-(2-cyanopropan-2-yl)phenyl, 4-(3-cyanopentan-3-yl)phenyl, 3-trifluoromethylphenyl, 4-trifluoromethylphenyl, 2-chlorophenyl, 3-chlorophenyl, 4-chlorophenyl, 4-chloro-2-fluorophenyl, 4-chloro-2-phenoxyphenyl, 2-chloro-4-trifluoromethylphenyl, 3,4-dimethylphenyl, 2,4-dichlorophenyl, 2-phenoxyphenyl, 4-tert-butylphenyl, 4-pentylphenyl, biphenyl, 6-fluorobenzothiazol-2-yl and 5-butyl-pyridin-2-yl;

Y is selected from —CH₂—NH—, —CH₂—N(CH₂-Phenyl)-, —NH—, —NHCONH—, —CON(H)— and —SO₂NH;

U is selected from

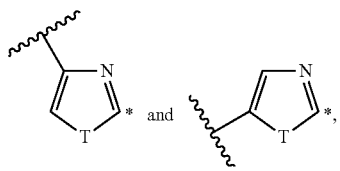

wherein T is —O— or —S—;

V is —CONR₄—;

$R_1$, $R_2$, $R_4$ and $R_5$ at each occurrence are independently selected from H and unsubstituted alkyl and $R_3$ is selected from —COOR$_p$ and carboxylic acid isostere selected from a group such as tetrazol-5-yl, 5-trifluoromethyl-1,2,4-triazol-3-yl, 5-(methylsulfonyl)-1,2,4-triazol-3-yl, and 2,5-dihydro-5-oxo-1,2,4-oxadiazol-3-yl; wherein $R_p$ is selected from H and unsubstituted alkyl;

* indicates the point of attachment to —V— and

indicates the point of attachment to phenyl ring.

Compounds of formula (I):

Methyl 3-methyl-2-(5-(4-(3-(3-(trifluoromethyl)phenyl)ureido)phenyl)oxazole-2-carboxamido)butanoate, 3-Methyl-2-(5-(4-(3-(3-(trifluoromethyl)phenyl)ureido)phenyl)oxazole-2-carboxamido)butanoic acid, Methyl 2-(5-(4-(3-(2-chlorophenyl)ureido)phenyl)oxazole-2-carboxamido)-3-methylbutanoate, 2-(5-(4-(3-(2-Chlorophenyl)ureido)phenyl)oxazole-2-carboxamido)-3-methylbutanoic acid, Methyl 2-(5-(4-(3-(3,4-dimethylphenyl)ureido)phenyl)oxazole-2-carboxamido)-3-methylbutanoate, 2-(5-(4-(3-(3,4-dimethylphenyl)ureido)phenyl)oxazole-2-carboxamido)-3-methylbutanoic acid, Methyl 2-(5-(4-(3-(4-chloro-2-phenoxyphenyl)ureido)phenyl)oxazole-2-carboxamido)-3-methylbutanoate, 2-(5-(4-(3-(4-chloro-2-phenoxyphenyl)ureido)phenyl)oxazole-2-carboxamido)-3-methylbutanoic acid, Methyl 3-methyl-2-(5-(4-(3-(3-(trifluoromethyl)phenyl)ureido)phenyl)thiazole-2-carboxamido)butanoate, 3-methyl-2-(5-(4-(3-(3-(trifluoromethyl)phenyl)ureido)phenyl)thiazole-2-carboxamido)butanoic acid, Methyl 2-(5-(4-(3-(2-chlorophenyl)ureido)phenyl)thiazole-2-carboxamido)-3-methylbutanoate, 2-(5-(4-(3-(2-Chlorophenyl)ureido)phenyl)thiazole-2-carboxamido)-3-methylbutanoic acid, Methyl 2-(5-(4-(3-(3,4-dimethylphenyl)ureido)phenyl)oxazole-2-carboxamido)-3-methylbutanoate, 2-(5-(4-(3-(3,4-dimethylphenyl)ureido)phenyl)oxazole-2-carboxamido)-3-methylbutanoic acid, Methyl 3-methyl-2-(5-(4-(3-(2-phenoxyphenyl)ureido)phenyl)thiazole-2-carboxamido)butanoate, 3-methyl-2-(5-(4-(3-(2-phenoxyphenyl)ureido)phenyl)thiazole-2-carboxamido)butanoic acid, Methyl 2-(5-(4-(3-(4-chloro-2-phenoxyphenyl)ureido)phenyl)thiazole-2-carboxamido)-3-methylbutanoate, 2-(5-(4-(3-(4-chloro-2-phenoxyphenyl)ureido)phenyl)thiazole-2-carboxamido)-3-methylbutanoic acid, Ethyl 2-(5-(4-(6-fluorobenzo[d]thiazol-2-ylamino)phenyl)thiazole-2-carboxamido)-3-methylbutanoate, 2-(5-(4-(6-fluorobenzo[d]thiazol-2-ylamino)phenyl)thiazole-2-carboxamido)-3-methylbutanoic acid, Methyl 2-(5-(4-(4-tert-butylbenzamido)phenyl)thiazole-2-carboxamido)-3-methylbutanoate, 2-(5-(4-(4-tert-butylbenzamido)phenyl)thiazole-2-carboxamido)-3-methylbutanoic acid, Methyl 2-(4-(4-(3-(2-chlorophenyl)ureido)phenyl)thiazole-2-carboxamido)-3-methylbutanoate, 2-(4-(4-(3-(2-Chlorophenyl)ureido)phenyl)thiazole-2-carboxamido)-3-methylbutanoic acid, Methyl 2-(4-(4-(6-fluorobenzo[d]thiazol-2-ylamino)phenyl)thiazole-2-carboxamido)-3-methylbutanoate, 2-(4-(4-(6-fluorobenzo[d]thiazol-2-ylamino)phenyl)thiazole-2-carboxamido)-3-methylbutanoic acid, Methyl 2-(4-(4-(4-tert-butylbenzamido)phenyl)thiazole-2-carboxamido)-3-methylbutanoate, 2-(4-(4-(4-tert-butylbenzamido)phenyl)thiazole-2-carboxamido)-3-methylbutanoic acid,
Methyl-3-methyl-2-(4-(4-(3-(4-(trifluoromethyl)phenyl)ureido)phenyl)thiazole-2-carboxamido)butanoate,
3-methyl-2-(4-(4-(3-(4-(trifluoromethyl)phenyl)ureido)phenyl)thiazole-2-carboxamido)butanoic acid,
Methyl 2-(4-(4-(3-(3,4-dimethylphenyl)ureido)phenyl)thiazole-2-carboxamido)-3-methylbutanoate,
2-(4-(4-(3-(3,4-Dimethylphenyl)ureido)phenyl)thiazole-2-carboxamido)-3-methylbutanoic acid,
Methyl 2-(4-(4-(3-(4-chloro-2-phenoxyphenyl)ureido)phenyl)thiazole-2-carboxamido)-3-methylbutanoate,
2-(4-(4-(3-(4-chloro-2-phenoxyphenyl)ureido)phenyl)thiazole-2-carboxamido)-3-methylbutanoic acid,
Methyl 2-(4-(4-biphenyl-4-ylcarboxamidophenyl)thiazole-2-carboxamido)-3-methylbutanoate,
2-(4-(4-Biphenyl-4-ylcarboxamidophenyl)thiazole-2-carboxamido)-3-methylbutanoic acid,
Methyl 3-methyl-2-(4-(4-(4-pentylbenzamido)phenyl)thiazole-2-carboxamido)butanoate,
3-Methyl-2-(4-(4-(4-pentylbenzamido)phenyl)thiazole-2-carboxamido) butanoic acid,
Methyl 3-methyl-2-(N-methyl-5-(4-(4-pentylbenzamido)phenyl)thiazole-2-carboxamido)butanoate,
3-Methyl-2-(N-methyl-5-(4-(4-pentylbenzamido)phenyl)thiazole-2-carboxamido) butanoic acid,
Methyl 2-(5-(4-biphenyl-4-ylcarboxamidophenyl)-N-methylthiazole-2-carboxamido)-3-methylbutanoate,
2-(5-(4-Biphenyl-4-ylcarboxamidophenyl)-N-methylthiazole-2-carboxamido)-3-methylbutanoic acid,
Methyl 2-(5-(4-(4-tert-butylbenzamido)phenyl)-N-methylthiazole-2-carboxamido)-3-methylbutanoate,
2-(5-(4-(4-tert-Butylbenzamido)phenyl)-N-methylthiazole-2-carboxamido)-3-methylbutanoic acid,
Methyl 2-(4-(4-(2,4-dichlorophenylsulfonamido)phenyl)thiazole-2-carboxamido)-3-methylbutanoate,
2-(4-(4-(2,4-Dichlorophenylsulfonamido)phenyl)thiazole-2-carboxamido)-3-methylbutanoic acid,
Methyl 2-(5-(4-biphenyl-4-ylcarboxamidophenyl)thiazole-2-carboxamido)-3-methylbutanoate,
2-(5-(4-biphenyl-4-ylcarboxamidophenyl)thiazole-2-carboxamido)-3-methylbutanoic acid,
Methyl 2-(5-(4-(3-cyclohexylpropanamido)phenyl)thiazole-2-carboxamido)-3-methylbutanoate,
2-(5-(4-(3-cyclohexylpropanamido)phenyl)thiazole-2-carboxamido)-3-methylbutanoic acid,
Methyl 2-(5-(4-(2,3-dihydro-1H-indene-2-carboxamido)phenyl)thiazole-2-carboxamido)-3-methylbutanoate,
2-(5-(4-(2,3-dihydro-1H-indene-2-carboxamido)phenyl)thiazole-2-carboxamido)-3-methylbutanoic acid,
Methyl 2-(5-(4-(4,4-difluorocyclohexanecarboxamido)phenyl)thiazole-2-carboxamido)-3-methylbutanoate,
2-(5-(4-(4,4-difluorocyclohexanecarboxamido)phenyl)thiazole-2-carboxamido)-3-methylbutanoic acid,
(S)-methyl 2-(5-(4-(3-(2,3-dihydro-1H-inden-5-yl)ureido)phenyl)oxazole-2-carboxamido)-3-methylbutanoate,
(S)-2-(5-(4-(3-(2,3-dihydro-1H-inden-5-yl)ureido)phenyl)oxazole-2-carboxamido)-3-methylbutanoic acid,
(S)-Methyl 2-(5-(4-(3-(4-chlorophenyl)ureido)phenyl)oxazole-2-carboxamido)-3-methylbutanoate,
(S)-2-(5-(4-(3-(4-chlorophenyl)ureido)phenyl)oxazole-2-carboxamido)-3-methylbutanoic acid,
(S)-methyl 2-(5-(4-(3-(3-chlorophenyl)ureido)phenyl)oxazole-2-carboxamido)-3-methylbutanoate,
(S)-2-(5-(4-(3-(3-chlorophenyl)ureido)phenyl)oxazole-2-carboxamido)-3-methylbutanoic acid,
(S)-methyl 2-(5-(4-(3-(2-chloro-4-(trifluoromethyl)phenyl)ureido)phenyl)oxazole-2-carboxamido)-3-methylbutanoate,
(S)-2-(5-(4-(3-(2-chloro-4-(trifluoromethyl)phenyl)ureido)phenyl)oxazole-2-carboxamido)-3-methylbutanoic acid,
(S)-methyl 2-(5-(4-(3-(4-chloro-2-fluorophenyl)ureido)phenyl)oxazole-2-carboxamido)-3-methylbutanoate,
(S)-2-(5-(4-(3-(4-chloro-2-fluorophenyl)ureido)phenyl)oxazole-2-carboxamido)-3-methylbutanoic acid,
(S)-Methyl 2-(5-(4-(3-(2,3-dihydro-1H-inden-5-yl)ureido)phenyl)thiazole-2-carboxamido)-3-methylbutanoate,
(S)-2-(5-(4-(3-(2,3-dihydro-1H-inden-5-yl)ureido)phenyl)thiazole-2-carboxamido)-3-methylbutanoic acid,
(S)-methyl 2-(5-(4-(3-(4-chlorophenyl)ureido)phenyl)thiazole-2-carboxamido)-3-methylbutanoate,
(S)-2-(5-(4-(3-(4-chlorophenyl)ureido)phenyl)thiazole-2-carboxamido)-3-methylbutanoic acid,
(S)-Methyl 2-(5-(4-(3-(3-chlorophenyl)ureido)phenyl)thiazole-2-carboxamido)-3-methylbutanoate,
(S)-2-(5-(4-(3-(3-chlorophenyl)ureido)phenyl)thiazole-2-carboxamido)-3-methylbutanoic acid,
(S)-methyl 2-(5-(4-(3-(2-chloro-4-(trifluoromethyl)phenyl)ureido)phenyl)thiazole-2-carboxamido)-3-methylbutanoate,
(S)-2-(5-(4-(3-(2-chloro-4-(trifluoromethyl)phenyl)ureido)phenyl)thiazole-2-carboxamido)-3-methylbutanoic acid,
(S)-methyl 2-(5-(4-(3-(4-chloro-2-fluorophenyl)ureido)phenyl)thiazole-2-carboxamido)-3-methylbutanoate,
(S)-2-(5-(4-(3-(4-chloro-2-fluorophenyl)ureido)phenyl)thiazole-2-carboxamido)-3-methylbutanoic acid,
(S)-Methyl 2-(4-(4-(3-(4-chlorophenyl)ureido)phenyl)thiazole-2-carboxamido)-3-methylbutanoate,
(S)-2-(4-(4-(3-(4-Chlorophenyl)ureido)phenyl)thiazole-2-carboxamido)-3-methylbutanoic acid,
(S)-Methyl 2-(4-(4-(3-(2,3-dihydro-1H-inden-5-yl)ureido)phenyl)thiazole-2-carboxamido)-3-methylbutanoate,
(S)-2-(4-(4-(3-(2,3-dihydro-1H-inden-5-yl)ureido)phenyl)thiazole-2-carboxamido)-3-methylbutanoic acid,
(S)-methyl 2-(4-(4-(3-(3-chlorophenyl)ureido)phenyl)thiazole-2-carboxamido)-3-methylbutanoate,
(S)-2-(4-(4-(3-(3-chlorophenyl)ureido)phenyl)thiazole-2-carboxamido)-3-methylbutanoic acid,
(S)-Methyl 2-(4-(4-(3-(2-chloro-4-(trifluoromethyl)phenyl)ureido)phenyl)thiazole-2-carboxamido)-3-methylbutanoate,
(S)-2-(4-(4-(3-(2-chloro-4-(trifluoromethyl)phenyl)ureido)phenyl)thiazole-2-carboxamido)-3-methylbutanoic acid,
(S)-Methyl 2-(4-(4-(3-(4-chloro-2-fluorophenyl)ureido)phenyl)thiazole-2-carboxamido)-3-methylbutanoate,
(S)-2-(4-(4-(3-(4-chloro-2-fluorophenyl)ureido)phenyl)thiazole-2-carboxamido)-3-methylbutanoic acid,
Methyl 2-(5-(4-(4-(2-cyanopropan-2-yl)benzamido)phenyl)thiazole-2-carboxamido)-3-methylbutanoate,
2-(5-(4-(4-(2-cyanopropan-2-yl)benzamido)phenyl)thiazole-2-carboxamido)-3-methylbutanoic acid,
Methyl 2-(5-(4-(4-(3-cyanopentan-3-yl)benzamido)phenyl)thiazole-2-carboxamido)-3-methylbutanoate,
2-(5-(4-(4-(3-cyanopentan-3-yl)benzamido)phenyl)thiazole-2-carboxamido)-3-methylbutanoic acid,
Methyl 2-(5-(4-(benzylamino)phenyl)thiazole-2-carboxamido)-3-methylbutanoate,
Methyl 2-(5-(4-((4-fluorobenzyl)amino)phenyl)thiazole-2-carboxamido)-3-methylbutanoate, 2-(5-(4-((4-Fluorobenzyl)amino)phenyl)thiazole-2-carboxamido)-3-methylbutanoic acid, Methyl 2-(5-(4-(dibenzylamino)phenyl)thiazole-2-carboxamido)-3-methylbutanoate, 2-(5-(4-(dibenzylamino)phenyl)thiazole-2-carboxamido)-3-methylbutanoic acid, Methyl 2-(5-(4-(5-butylpicolinamido)phenyl)thiazole-2-carboxamido)-3-methylbutanoate, 2-(5-(4-(5-butylpicolinamido)phenyl)thiazole-2-carboxamido)-3-methylbutanoic acid, and stereoisomers thereof and tautomers thereof and prodrugs thereof and pharmaceutically acceptable salts and solvates thereof, According to a further aspect of the present invention, there is provided a process for the preparation of a compound of formula (I) and its salt, solvate or prodrug.

According to a further aspect of the present invention, there is provided a process for the preparation of a compound of formula (10)

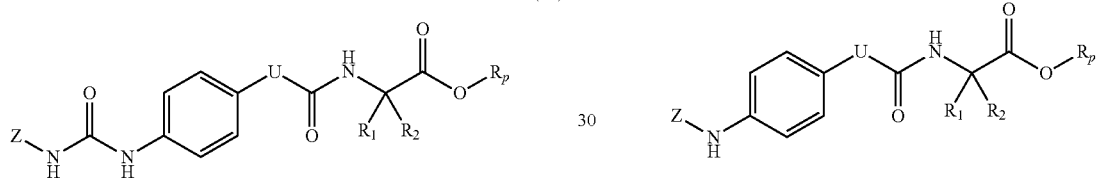

(10)

comprising,
reacting a compound of formula (9)

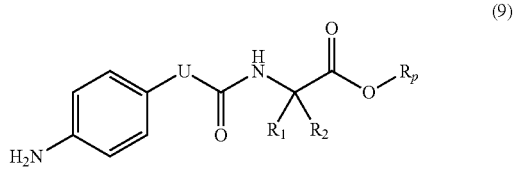

(9)

with an isocyanate of formula Z—NCO in a solvent such as tetrahydrofuran,
wherein, Z, U, $R_1$ and $R_2$ are as defined for formula (I) and $R_p$ is alkyl.

According to a further aspect of the present invention, there is provided a process for the preparation of a compound of formula (12)

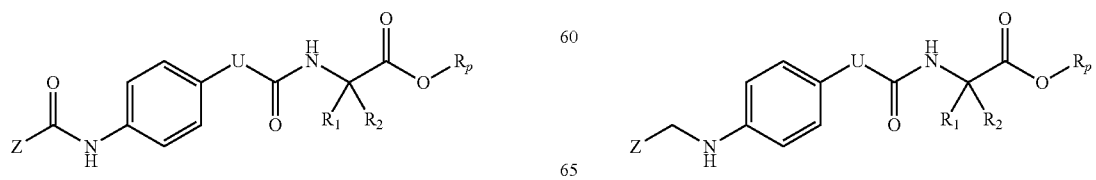

(12)

comprising,
reacting a compound of formula (9)

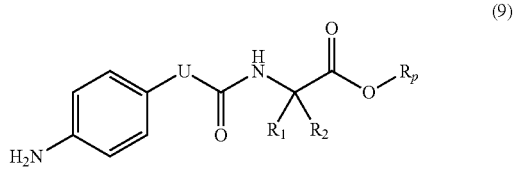

(9)

with a compound of formula Z—COCl in a solvent such as DCM and in presence of a base such as pyridine, or with a compound of formula Z—COOMe in presence of trimethylaluminum and a solvent such as toluene, wherein, Z, U, $R_1$, and $R_2$ are as defined for formula (I) and $R_p$ is alkyl.

According to a further aspect of the present invention, there is provided a process for the preparation of a compound of formula (14)

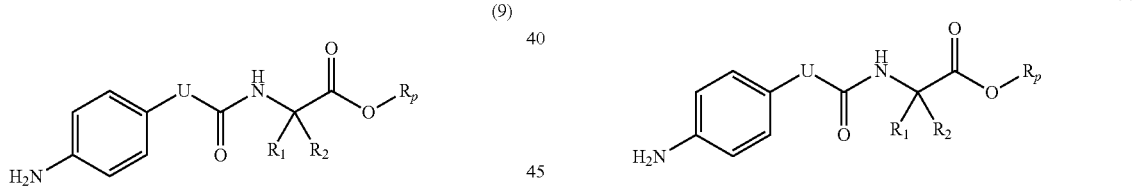

(14)

comprising,
reacting a compound of formula (9)

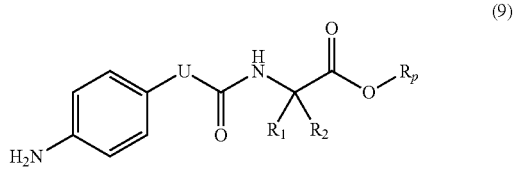

(9)

with a compound of formula Z—Cl in a solvent such as n-butanol in presence of hydrochloric acid in dioxane or with a compound of formula Z—Br in a solvent such as DCM in a presence of a base such as triethylamine, wherein, Z, U, $R_1$, and $R_2$ are as defined for formula (I) and $R_p$ is alkyl.

According to a further aspect of the present invention, there is provided a process for the preparation of a compound of formula (14a)

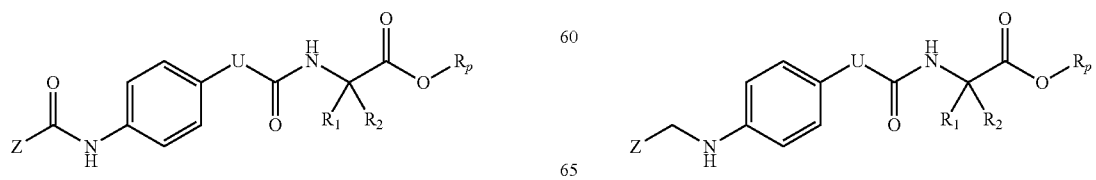

(14a)

comprising,
reacting a compound of formula (9)

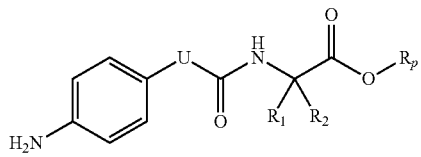
(9)

with a compound of formula Z—CH$_2$Cl or Z—CH$_2$Br in a solvent such as acetone in presence of a base such as potassium carbonate, wherein, Z, U, R$_1$, and R$_2$ are as defined for formula (I) and R$_p$ is alkyl.

According to a further aspect of the present invention, there is provided a process for the preparation of a compound of formula (18)

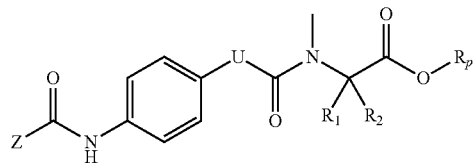
(18)

comprising,
reacting a compound of formula (17)

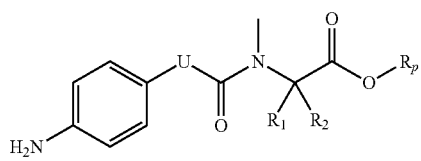
(17)

with a compound of formula Z—COCl, in a solvent such as DCM in presence of a base such as pyridine, wherein, Z, U, R$_1$, and R$_2$ are as defined for formula (I) and R$_p$ is alkyl.

According to a further aspect of the present invention, there is provided a process for the preparation of a compound of formula (20)

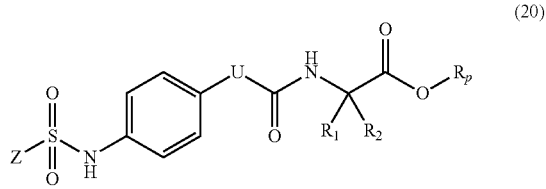
(20)

comprising,
reacting a compound of formula (9)

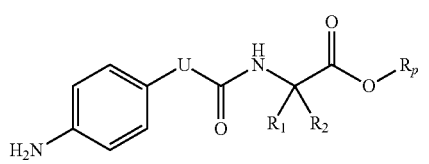
(9)

with a compound of formula Z—SO$_2$Cl in a solvent such as DCM in presence of a base such as pyridine, wherein, Z, U, R$_1$, and R$_2$ are as defined for formula (I) and R$_p$ is alkyl.

The compounds of formula (10), (12), (14), (18) and (20) can be converted to corresponding acids by alkaline hydrolysis; optionally converting the resultant acid into salts, solvates or prodrugs.

Methods of Preparation

The compounds of formula (I) can be prepared using various procedures, some of which are depicted in the schemes below. Those with skill in the art will appreciate that the specific starting compounds and reagents, such as acids, bases, solvents, reducing agents; temperature conditions etc. identified in the Schemes can be altered to prepare compounds encompassed by the present invention.

Scheme 1

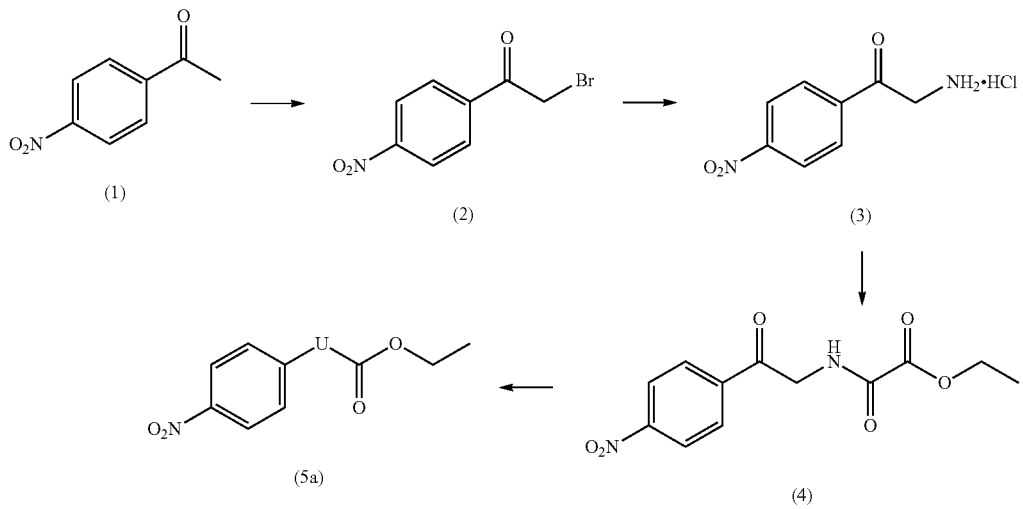

wherein, U is

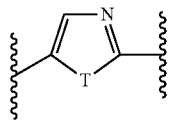

and T is —O— or —S—.

As illustrated in Scheme 1, compound of formula (1) can be treated with bromine in presence of a catalyst such as aluminium chloride in a solvent such as ether to provide a compound of formula (2). The 2-bromo-1-(4-nitrophenyl) ethanone of formula (2) can be treated with an amine such as hexamethylenetetramine in a solvent such as dichloromethane to provide a compound of formula (3). The compound of formula (3) can be refluxed with ethylchlorooxoacetate in a solvent such as ethyl acetate in presence of a base such as triethylamine to provide a compound of formula (4). The compound of formula (4) can be i) refluxed in presence of phosphorus oxychloride to provide a cyclized compound of formula (5a), wherein U is and T is —O—, or
ii) refluxed with Lawesson's reagent in a solvent such as 1,4-dioxane to provide a cyclized compound of formula (5a), wherein U is and T is —S—.

Scheme 2

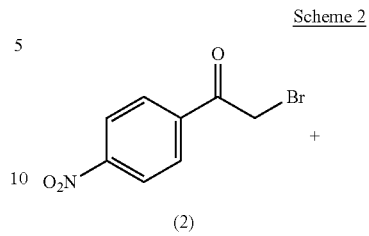

(2)

wherein, U is and T is —O— or S.

As illustrated in Scheme 2, compound of formula (2) can be refluxed with compound of formula (6) in a solvent such as methanol to provide a cyclized compound of formula (5b), wherein U is and T is —O— or —S—.

Scheme 3

-continued

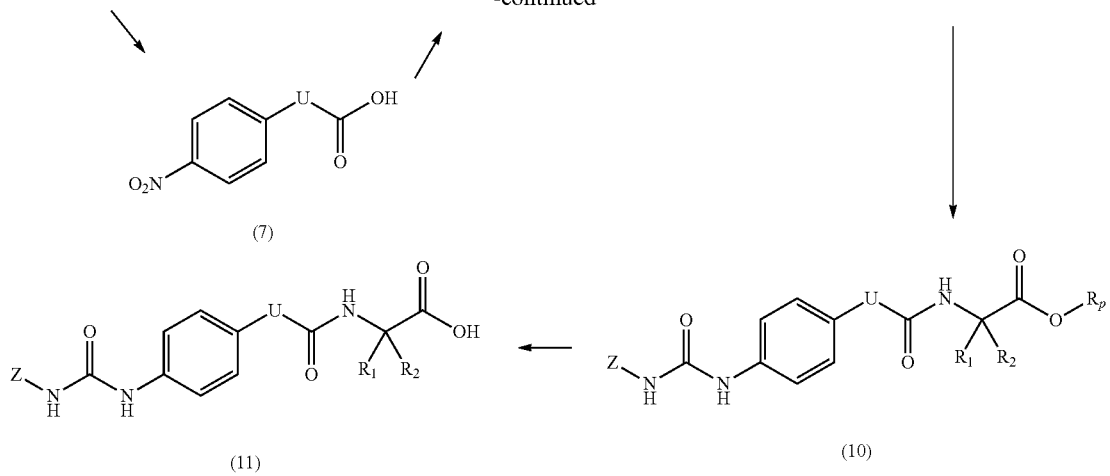

(7)

(11)

(10)

wherein, Z, U, $R_1$ and $R_2$ are as defined for formula (I) and $R_p$ is alkyl.

As illustrated in Scheme 3, compound of formula (5a) or (5b), wherein U is as defined for formula (I), can be i) treated with

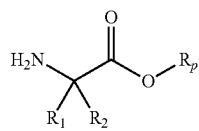

in presence of a base such as triethylamine in a solvent such as ethanol to provide a compound of formula (8) or ii) hydrolyzed in presence of a base such as lithium hydroxide in a solvent such as a tetrahydrofuran to provide a compound of formula (7). The compound of formula (7) can be treated with a compound of formula

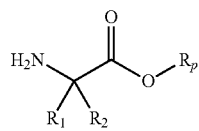

in presence of a coupling agent such as isobutyl chloroformate, in presence of a base such as triethylamine in a solvent such as tetrahydrofuran, N-methylmorpholine and the like to provide a compound of formula (8).

The nitro group of compound of formula (8) can be reduced in presence of a reducing agent such as iron/ammonium chloride to provide a compound of formula (9). The compound of formula (9) can be treated with an isocyanate of formula Z—NCO in a solvent such as tetrahydrofuran to form a compound of formula (10). The ester of formula (10) can be hydrolyzed in presence of a base such as lithium hydroxide in a solvent such as tetrahydrofuran to form an acid of formula (11), wherein Z, U, $R_1$, and $R_2$ are as defined for formula (I).

Scheme 4

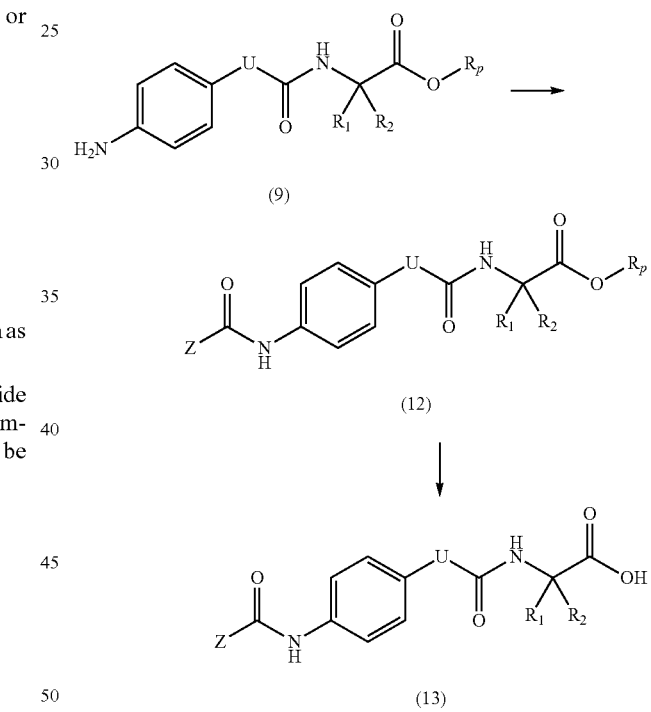

(9)

(12)

(13)

wherein, Z, U, $R_1$, and $R_2$ are as defined for formula (I) and $R_p$ is alkyl.

As illustrated in Scheme 4, compound of formula (9), wherein U, $R_1$ and $R_2$ are as defined for formula (I) and $R_p$ is alkyl, can be treated with a compound of formula Z—COCl, in presence of a base such as pyridine in a solvent such as dichloromethane or can be treated with a compound of formula Z—COOMe in presence of a reagent such as trimethylaluminum in a solvent such as toluene wherein Z is as defined for formula (I), to provide a compound of formula (12). The ester of formula (12) can be hydrolyzed in presence of a base such as lithium hydroxide in a solvent such as tetrahydrofuran to provide a compound of formula (13), wherein, Z, U, $R_1$, and $R_2$ are as defined for formula (I).

Scheme 5

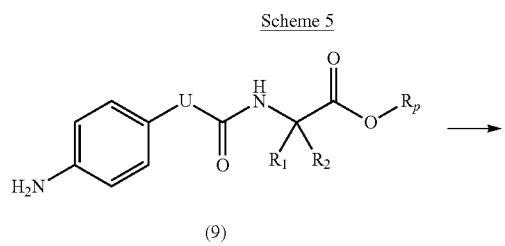

Scheme 5a

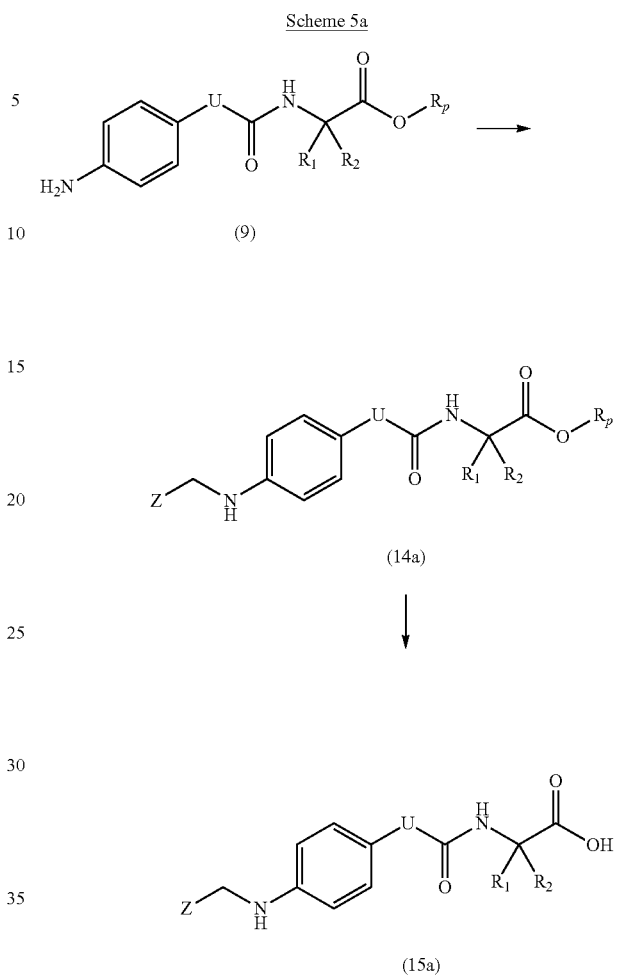

wherein, Z, U, $R_1$ and $R_2$ are as defined for formula (I) and $R_p$ is alkyl.

As illustrated in Scheme 5, compound of formula (9), wherein U, $R_1$ and $R_2$ are as defined for formula (I) and $R_p$ is alkyl, can be refluxed with a compound of formula Z—Cl or Z—Br, wherein Z is as defined for formula (I), in presence of an acid such as hydrochloric acid in a solvent such as 1,4-dioxane, ethanol and the like to provide a compound of formula (14). The compound of formula (14) can be hydrolyzed in presence of a base such as lithium hydroxide in a solvent such as tetrahydrofuran to provide a compound of formula (15), wherein Z, U, $R_1$, and $R_2$ are as defined for formula (I).

wherein, Z, U, $R_1$, and $R_2$ are as defined for formula (I) and $R_p$ is alkyl.

As illustrated in Scheme 5a, compound of formula (9), wherein U, $R_1$ and $R_2$ are as defined for formula (I) and $R_p$ is alkyl, can be reacted with a compound of formula Z—$CH_2$Cl or Z—$CH_2$Br, wherein Z is as defined for formula (I), in presence of a base such as potassium carbonate in a solvent such as acetone and the like to provide a compound of formula (14a). The compound of formula (14a) can be hydrolyzed in presence of a base such as lithium hydroxide in a solvent such as tetrahydrofuran to provide a compound of formula (15a), wherein Z, U, $R_1$ and $R_2$ are as defined for formula (I).

Scheme 6

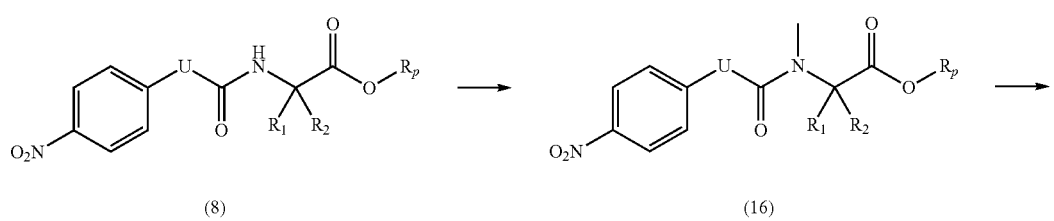

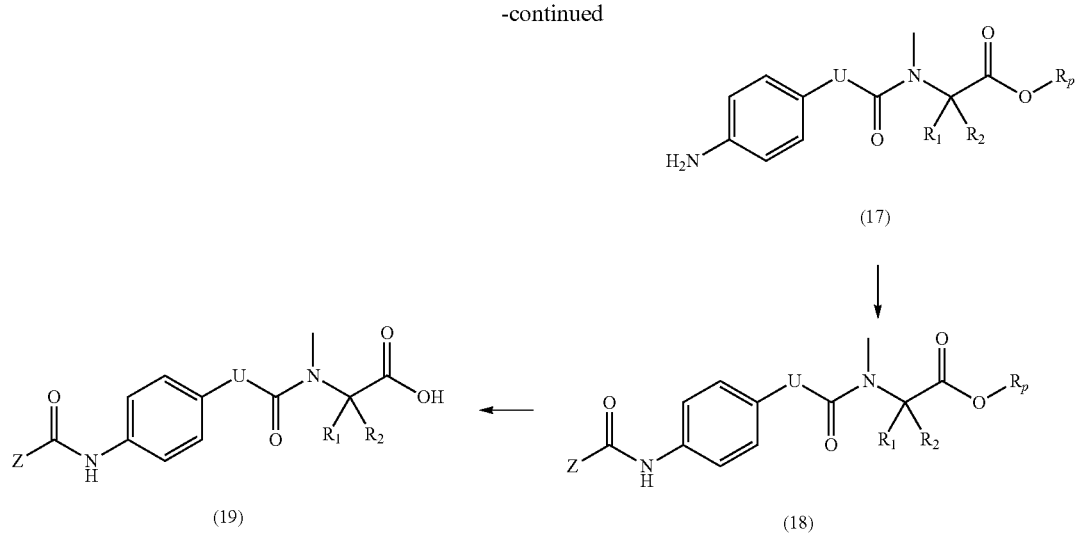

(17)

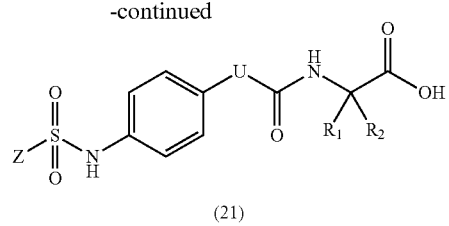

(19)       (18)

wherein, Z, U, R₁, and R₂ are as defined for formula (I) and $R_p$ is alkyl.

As illustrated in Scheme 6, compound of formula (8), wherein U, R₁, and R₂ are as defined for formula (I) and $R_p$ is alkyl, can be treated with methylating agent such as methyliodide in presence of a base such as cesium carbonate or potassium carbonate to provide a compound of formula (16). The nitro group of compound of formula (16) can be reduced in presence of a reducing agent such as iron/ammonium chloride to provide a compound of formula (17). The compound of formula (17) can be treated with a compound of formula Z—COCl, wherein Z is as defined for formula (I), in presence of a base such as pyridine and in a solvent such as dichloromethane to provide a compound of formula (18). The ester of formula (18) can be hydrolyzed in presence of a base such as lithium hydroxide and in a solvent such as tetrahydrofuran to provide a compound of formula (19), wherein Z, U, R₁ and R₂ are as defined for formula (I).

Scheme 7

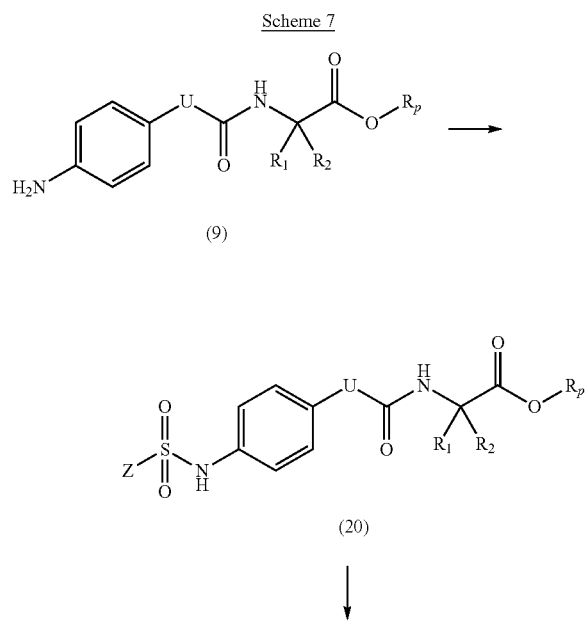

-continued (21)

wherein, Z, U, R₁, and R₂ are as defined for formula (I) and $R_p$ is alkyl.

As illustrated in Scheme 7, compound of formula (9), wherein U, R₁, and R₂ are as defined for formula (I) and $R_p$ is alkyl, can be treated with a compound of formula Z—SO₂Cl, wherein Z is as defined for formula (I), in presence of a base such as pyridine in a solvent such as dichloromethane to provide a compound of formula (20). The ester of formula (20) can be hydrolyzed in presence of a base such as lithium hydroxide in a solvent such as tetrahydrofuran to provide a compound of formula (21), wherein Z, U, R₁, and R₂ are as defined for formula (I).

The present invention also includes within its scope all isotopically labeled forms of compounds of formula (I), wherein one or more atoms of compounds of formula (I) are replaced by their respective isotopes. Examples of isotopes that may be incorporated into the compounds disclosed herein include, but are not limited to, isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, chlorine such as $^{36}Cl$, fluorine such as $^{18}F$ and sulphur such as $^{35}S$.

Substitution with heavier isotopes, for example, replacing one or more key carbon-hydrogen bonds with carbon-deuterium bond may show certain therapeutic advantages, for example, longer metabolism cycles, improved safety or greater effectiveness.

Isotopically labeled forms of compounds of formula (I), can be prepared by conventional techniques known to those skilled in the art or by processes analogous to those described above and in the subsequent Experimental section by using an appropriate isotopically labeled reagent instead of non-labeled reagent.

The compounds of the present invention represented by the general formula (I), which contain acidic groups, may be converted into salts with pharmaceutically acceptable bases. Such salts include, for example, alkali metal salts, like lithium, sodium and potassium salts; alkaline earth metal salts like calcium and magnesium salts, ammonium salts, for example, [tris(hydroxymethyl)aminomethane], trimethylamine salts and diethylamine salts; salts with amino acids such as lysine, arginine, guanidine and the like.

The compounds of the present invention represented by formula (I), which contain one or more basic groups, i.e. groups which can be protonated, can form an addition salt with an inorganic or organic acid. Examples of suitable acid addition salts include: acetates, alginates, ascorbates, aspartates, benzoates, benzenesulfonates, bisulfates, borates, cinnamates, citrates, ethanesulfonates, fumarates, glucuronates, glutamates, glycolates, hydrochlorides, hydrobromides, hydrofluorides, ketoglutarates, lactates, maleates, malonates, mesylate, nitrates, oxalates, palmoates, perchlorates, phosphates, picrates, salicylates, succinates, sulfamate, sulfates, tartrates, tosylate and other acids known to the person skilled in the art.

The pharmaceutically acceptable salts of the present invention can be synthesized from the subject compound, which contains a basic or an acidic moiety, by conventional chemical methods. Generally the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, tetrahydrofuran, dioxane or mixtures of these solvents. These salts can also be used for purification of the compounds obtained.

The present invention furthermore includes all solvates of the compounds of the formula (I), for example hydrates, and the solvates formed with other solvents of crystallization, such as alcohols, ethers, ethyl acetate, dioxane, dimethylformamide or a lower alkyl ketone, such as acetone, or mixtures thereof.

The present invention also includes prodrugs and other physiologically acceptable derivatives of compounds of formula (I).

The process of the present invention described herein therefore comprises the optional step of forming a salt and/or a solvate and/or a prodrug of the compound of formula (I).

An optically active from of a compound of the present invention may be obtained by using an optically active starting material or by resolution of a racemic form of the compound using standard procedures.

Methods of Treatment

The present compounds are DGAT-1 inhibitors and find use in the treatment of clinical conditions associated with obesity and obesity related disorders in a warm-blooded animal. The compounds of the present invention are particularly useful for the delay or treatment of a range of disease states associated with obesity, including diabetes mellitus, more specifically type 2 diabetes mellitus (T2DM), and complications arising therefrom (for example retinopathy, neuropathy and nephropathy), insulin resistance, impaired glucose tolerance (IGT), conditions of impaired fasting glucose, metabolic acidosis, ketosis, steatosis, dysmetabolic syndrome, arthritis, osteoporosis, and other obesity related disorders, which include peripheral vascular disease, (including intermittent claudication), cardiac failure and certain cardiac myopathies, hypertension, myocardial ischaemia, myocardial infarction, arteriosclerosis, atherosclerosis, hypercholesterolemia, hypertriglyceridemia, hyperlipidaemia, cerebral ischaemia and reperfusion, infertility and polycystic ovary syndrome, muscle weakness, diseases of the skin such as acne, various immunomodulatory diseases such as psoriasis, inflammatory bowel syndrome and inflammatory bowel disease such as Crohn's disease and ulcerative colitis. The compounds of the present invention may be useful for the treatment of Hepatitis C infection.

According to another aspect of the present invention, there is provided a method for the treatment of diseases mediated by DGAT-1, comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of diseases mediated by DGAT-1 selected from obesity and obesity related disorders comprising administering to a mammal in need thereof a therapeutically effective amount of a compound of formula (I) or a pharmaceutically acceptable salt or a pharmaceutically acceptable solvate thereof.

According to another aspect of the present invention, there is provided a method for the treatment of obesity comprising administering to a mammal in need thereof a therapeutically effective amount of a compound of formula (I) or a pharmaceutically acceptable salt or a pharmaceutically acceptable solvate thereof.

According to another aspect of the present invention, there is provided the use of a compound of formula (I) in the treatment of diseases mediated by DGAT-1.

According to another aspect of the present invention, there is provided the use of a compound of formula (I) in the treatment of diseases mediated by DGAT-1 selected from obesity and obesity related disorders.

According to another aspect of the present invention, there is provided the use of a compound of formula (I) or a pharmaceutically acceptable salt or a pharmaceutically acceptable solvate thereof, for the manufacture of a medicament for the treatment of diseases mediated by DGAT-1.

According to another aspect of the present invention, there is provided the use of a compound of formula (I) or a pharmaceutically acceptable salt or a pharmaceutically acceptable solvate thereof, for the manufacture of a medicament for the treatment of diseases mediated by DGAT-1 selected from obesity and obesity related disorders.

According to another aspect of the present invention, the obesity related disorders are selected from peripheral vascular disease, diabetes mellitus, insulin resistance, impaired glucose tolerance, diabetic neuropathy, diabetic nephropathy, diabetic retinopathy, hypercholesterolemia, hypertriglyceridemia, hyperlipidemia, metabolic acidosis, ketosis, steatosis, dysmetabolic syndrome, arthritis, osteoporosis, cardiovascular diseases such as hypertension, cardiac failure, cardiomyopathy, myocardial ischaemia, myocardial infarction, arteriosclerosis and atherosclerosis, cerebral ischaemia and reperfusion, infertility, polycystic ovary syndrome, muscle weakness, diseases of the skin such as acne, various immunomodulatory diseases such as psoriasis, inflammatory bowel syndrome or inflammatory bowel disease such as Crohn's disease and ulcerative colitis.

According to another aspect of the present invention, the obesity related disorders are selected from diabetes mellitus, insulin resistance, impaired glucose tolerance, diabetic neuropathy, diabetic nephropathy, diabetic retinopathy, metabolic acidosis, ketosis or steatosis.

According to another aspect of the present invention, the obesity related disorders are selected from peripheral vascular disease, hypercholesterolemia, hypertriglyceridemia, hyperlipidemia, dysmetabolic syndrome, cardiovascular diseases such as hypertension, cardiac failure, cardiomyopathy, myocardial ischaemia, myocardial infarction, arteriosclerosis or atherosclerosis.

According to another aspect of the present invention, the obesity related disorders are selected from arthritis, osteoporosis, cerebral ischaemia and reperfusion, infertility, polycystic ovary syndrome, muscle weakness, diseases of the skin such as acne, various immunomodulatory diseases such as psoriasis, inflammatory bowel syndrome and inflammatory bowel disease such as Crohn's disease or ulcerative colitis.

In particular, the compounds of the present invention are of interest for the delay or treatment of diabetes mellitus and/or obesity and/or obesity related disorders. The inhibition of DGAT1 activity may be applied as a sole therapy or in combination with one or more other substances and/or treatments for the indication being treated. Conjoint treatment may be beneficial in the treatment of metabolic syndrome (as defined by International Diabetes Federation). Such conjoint treatments may include the following main categories:

1) Anti-obesity therapies, such as those that cause weight loss by effects on food intake, nutrient absorption or energy expenditure, such as orlistat, sibutramine and the like;
2) CB1 receptor blocker such as rimonabant;
3) Insulin secretagogues, including sulphonylureas (for example glibenclamide, glipizide), prandial glucose regulators (for example repaglinide, nateglinide);
4) Agents that improve incretin action (for example dipeptidyl peptidase IV (DPPIV) inhibitors, and GLP-I agonists) or incretin mimetics such as exenatide;
5) Insulin sensitising agents, including PPARgamma agonists (for example pioglitazone and rosiglitazone), and agents with combined PPARalpha and gamma activity;
6) Agents that modulate hepatic glucose balance (for example metformin, fructose 1,6 bisphosphatase inhibitors, glycogen phopsphorylase inhibitors, glycogen synthase kinase inhibitors, glucokinase activators);
7) Agents designed to reduce the absorption of glucose from the intestine (for example acarbose);
8) Agents that prevent the reabsorption of glucose by the kidney (SGLT inhibitors);
9) Agents designed to treat the complications of prolonged hyperglycaemia (for example, aldose reductase inhibitors);
10) Anti-dyslipidaemia agents such as, HMG-CoA reductase inhibitors (e.g. statins), PPARα-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
11) Antihypertensive agents such as, β-blockers (e.g., atenolol, inderal); ACE inhibitors (e.g., lisinopril); Calcium antagonists (e.g., nifedipine); Angiotensin receptor antagonists (e.g., candesartan), a antagonists and diuretic agents (e.g., furosemide, benzthiazide);
12) Haemostasis modulators, such as antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and low molecular weight analogues, hirudin) and warfarin;
13) Agents which antagonise the actions of glucagon;
14) Anti-inflammatory agents, such as non-steroidal anti-inflammatory drugs (eg. aspirin) and steroidal anti-inflammatory agents (eg. cortisone);

A compound of formula (I) may be administered either simultaneously or before or after the other active ingredient, either separately by the same or different route of administration or together in the same pharmaceutical formulation.

In addition to their use in therapeutic medicine the compounds are also useful as pharmacological tools in the development and standardisation of in vitro and in vivo test systems for the evaluation of the effects of inhibitors of DGAT1 activity in laboratory animals, such as cats, dogs, rabbits, monkeys, rats and mice, as part of the search for new therapeutic agents.

Pharmaceutical Compositions and Methods

According to another aspect of the present invention, there is provided a pharmaceutical composition comprising a compound of formula (I) described hereinabove as active ingredient, or a pharmaceutical salt thereof, in association with a pharmaceutically acceptable carrier or excipient. The pharmaceutical composition is for use in the treatment of obesity, diabetes, insulin resistance, impaired glucose tolerance and conditions associated therewith.

The pharmaceutical composition of the present invention may be in a form suitable for i) oral use, for example, aqueous or oily suspensions, dispersible powders or granules, elixirs, emulsions, hard or soft capsules, lozenges, syrups, tablets or trouches; or ii) topical use, for example, creams, ointments, transdermal patches, gels, aqueous or oily solutions or suspensions; or iii) parenteral administration, for example, sterile aqueous or oily solution for intravenous, subcutaneous, intraperitoneal, intramuscular or as a suppository for rectal dosing or iv) for inhalation use, for example, aerosols.

The pharmaceutical preparations according to the invention are prepared in a manner known per se and familiar to one skilled in the art and may contain one or more agents selected from the group consisting of sweetening agents, flavoring agents, coloring agents and preserving agents. Tablets and capsules contain the active ingredient in admixture with pharmaceutically acceptable excipients, for example, diluents such as calcium carbonate, sorbitol, mannitol, lactose or dextrose; disintegrating and/or granulating agents such as microcrystalline cellulose, starch, agar or alginic acid; binding agents such as gelatin, tragacanth, polyvinylpyrrolidone, acacia, starch, magnesium or aluminum silicate and lubricating agents such as magnesium stearate, talc or stearic acid. The tablets may be uncoated or coated. The coating may be done to mask the unpleasant taste (for example, sugar coating) or to delay the disintegration (for example enteric coating).

Aqueous or oily suspensions contain the active ingredient in admixture with pharmaceutically acceptable excipients, for example, suspending agents such as sodium carboxymethylcellulose, methylcellulose or tragacanth; dispersing or wetting agents such as, lecithin or polyoxyethylene stearate; thickening agent such as beeswax or hard paraffin; preservatives such as methyl or ethyl paraben and anti-oxidants such as alpha-tocopherol.

Injectable preparations may be sterile aqueous solutions or suspensions or emulsions. Such preparations may contain adjuvants such as, preserving agents, stabilizing agents, wetting or emulsifying agents, salts and/or buffers for regulating osmotic pressure.

The pharmaceutical preparations normally contain about 1 to 99%, for example, about 5 to 70%, or from about 5 to about 30% or from by weight of the compound of the formula (I)

and/or its physiologically tolerable salt. The amount of the active ingredient of the compound of formula (I) and/or its physiologically tolerable salt in the pharmaceutical preparations normally is from about 5 to 500 mg.

The dose of the compounds of this invention, which is to be administered, can cover a wide range. The dose to be administered daily is to be selected to suit the desired effect. A suitable dosage for a subject of about 50-70 kg may be about 1 mg to 1000 mg/day of the compound of formula (I), and/or its physiologically tolerable salt, for example, about 1 to 500 mg/day of a compound of formula (I), or a pharmaceutically acceptable salt of the compound. If required, higher or lower daily doses can also be administered. Actual dosage levels of the active ingredients in the pharmaceutical compositions of this invention may be varied so as to obtain an amount of the active ingredient, which is effective to achieve the desired therapeutic response for a particular patient, composition, and mode of administration without causing undue side effects or being toxic to the patient.

The selected dosage level will depend upon a variety of factors, including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredient of the compound of general formula (I) and/or its physiologically acceptable salt and carrier substances, the pharmaceutical preparations can contain additives such as, for example, fillers, antioxidants, dispersants, emulsifiers, defoamers, flavors, preservatives, solubilizers or colorants. They can also contain two or more compounds of the general formula (I), and/or their physiologically tolerable salts. Furthermore, in addition to at least one compound of the general formula (I), and/or its physiologically tolerable salt, the pharmaceutical preparations can also contain one or more other therapeutically or prophylactically active ingredients.

It is understood that modifications that do not substantially affect the activity of the various embodiments of this invention are included within the invention disclosed herein. Accordingly, the following Examples are intended to illustrate but not to limit the present invention.

EXPERIMENTAL

The invention is further understood by reference to the following Examples, which are intended to be purely exemplary of the invention. The present invention is not limited in scope by the exemplified embodiments, which are intended as illustrations of single aspects of the invention only. Any methods that are functionally equivalent to those described in the Examples are within the scope of the invention. Various modifications of the invention in addition to those described herein will become apparent to those skilled in the art from the foregoing description. Such modifications fall within the scope of the appended claims.

Unless otherwise stated, all temperatures are in degree Celsius. Also, in these Examples and elsewhere, abbreviations have the following meanings:

| | |
|---|---|
| $NH_4Cl$ | Ammonium chloride |
| $CHCl_3$ | Chloroform |
| $CH_2Cl_2$ or DCM | Dichloromethane/ Methylene chloride |
| DMSO | Dimethyl sulfoxide |
| EtOH | Ethanol |
| EtOAc | Ethyl acetate |
| g | Gram |
| H | Hour(s) |
| HCl | Hydrochloric acid |
| ml | Milliliter |
| Pet ether | Petroleum ether |
| $POCl_3$ | Phosphorus oxychloride |
| KBr | Potassium bromide |
| RT | Room temperature (20-30° C.) |
| $NaHCO_3$ | Sodium bicarbonate |
| $Na_2CO_3$ | Sodium carbonate |
| NaOH | Sodium hydroxide |
| $Na_2SO_4$ | Sodium sulfate |
| THF | Tetrahydrofuran |
| $Et_3N$ | Triethylamine |

Intermediates

The following intermediates were used in the preparation of the Examples

Intermediate 1

Methyl 2-(5-(4-aminophenyl)oxazole-2-carboxamido)-3-methylbutanoate

A. 2-bromo-1-(4-nitrophenyl)ethanone

4-Nitroacetophenone (25 g) in ether (250 ml) was treated with aluminium chloride (catalytic amount) followed by bromine (7.77 ml) for 10 minutes and the reaction was stirred for 30 minutes. The reaction was quenched with aqueous $NaHCO_3$, the ether layer was separated, dried using $Na_2SO_4$ and concentrated. The residue was dissolved in EtOAc, dried using $Na_2SO_4$, and concentrated to get off white solid which was crystallized in EtOAc/Pet ether to yield 25.5 gm (69%) of the title compound. $^1$HNMR (CDCl$_3$, 300 MHz): δ 8.19 (d, 2H), 8.36 (d, 2H), 4.47 (s, 2H).

B. 2-amino-1-(4-nitrophenyl)ethanone Hydrochloride

Hexamethylenetetramine (20.1 g) was added to a solution of 2-bromo-1-(4-nitrophenyl)ethanone (step A product, 25 g) in DCM (250 ml) and the mixture was stirred for 1 hour. It was then filtered and the residue was dissolved in ethanolic HCl (40 mL HCl in 162 ml EtOH). The ethanolic solution was stirred for 3 hours and was left undisturbed for 2 days. The solution was filtered and the residue was washed with water and dried to yield 11.8 g (72%) of the title compound. $^1$HNMR (DMSO-d$_6$, 300 MHz): δ 8.3 (bs, 3H), 8.38 (d, 2H), 8.27 (d, 2H), 4.68 (s, 2H).

C. Ethyl 2-(2-(4-nitrophenyl)-2-oxoethylamino)-2-oxoacetate $Et_3N$ (8.88 ml) was added to a solution of 2-amino-1-(4-nitrophenyl)ethanone hydrochloride (step B product, 11.5 g) in EtOAc (115 ml). This was followed by drop wise addition of Ethylchlorooxoacetate (7.11 ml). The reaction mixture was refluxed for 2 hours. It was then cooled and quenched with water. The organic layer was separated, dried over Na$_2$SO$_4$ and the solvent was concentrated to get dark brown oil which was purified by column chromatography in 3:7 Ethyl acetate:Pet ether to get yellow solid. The solid was crystallized in ethyl acetate/pet ether to yield 8.9 g (59%) of the title compound. $^1$HNMR (DMSO-d$_6$, 300 MHz): δ 9.21 (t, 1H), 8.35 (d, 2H), 8.24 (d, 2H), 4.78 (d, 2H), 4.29 (q, 2H), 1.29 (t, 3H).

D. Ethyl 5-(4-nitrophenyl)oxazole-2-carboxylate

A solution of Ethyl 2-(2-(4-nitrophenyl)-2-oxoethylamino)-2-oxoacetate (step C product, 8.5 g) in POCl$_3$ (55 ml) was refluxed for 6 hours. The reaction mixture was cooled, quenched with ice and neutralized with sodium carbonate. DCM was added to it and the organic and aqueous layers were separated. Organic layer was dried over Na$_2$SO$_4$, filtered and concentrated under reduced pressure to get dark brown residue. The residue was chromatographed on silica gel in 2:8 Ethyl acetate:Pet ether to get pale brown colored solid which was crystallized in chloroform/pet ether to yield 4.82 g (60%) of the title compound. $^1$HNMR (CDCl$_3$, 300 MHz): δ 8.41 (d, 2H), 7.97 (d, 2H), 7.37 (s, 1H), 4.55 (q, 2H), 1.49 (t, 3H).

E. Methyl 3-methyl-2-(5-(4-nitrophenyl)oxazole-2-carboxamido)butanoate

An ethanolic solution of Ethyl 5-(4-nitrophenyl)oxazole-2-carboxylate (step D product, 3.4 g) and L-valine methyl ester hydrochloride (5.43 g) previously neutralized with Et$_3$N (4.52 ml), was heated in a sealed tube at 110° C. for 2 days. EtOH was removed under reduced pressure and the crude material was chromatographed on silica gel in 1:9 EtOAc:Pet ether to get cream colored solid which was crystallized in EtOAc/pet ether to yield 700 mg (31%) of the title compound. $^1$HNMR (DMSO-d$_6$, 300 MHz): δ 9.2 (d, 1H), 8.37 (d, 2H), 8.24 (s, 1H), 8.14 (d, 2H), 4.32 (m, 1H), 3.68 (s, 3H), 2.26 (m, 1H), 0.96 (t, 6H); MS (ES+): m/z 348 (M+1).

F. Methyl 2-(5-(4-aminophenyl)oxazole-2-carboxamido)-3-methylbutanoate

Methyl 3-methyl-2-(5-(4-nitrophenyl)oxazole-2-carboxamido)butanoate (step E product, 700 mg) was dissolved in a solvent mixture of EtOH (7 ml), THF (2.8 ml), and water (2.8 ml). Ammonium chloride (323 mg) and iron (264 mg) were then added and the reaction mixture was refluxed at 80° C. for 3 hours. It was then cooled, filtered through celite and the solvent was removed under reduced pressure to get dark brown residue. The residue was dissolved in water and extracted with EtOAc. Organic layer was separated, dried over Na$_2$SO$_4$ and concentrated to get dark brown residue which was purified by silica gel column chromatography in 2.5:7.5 EtOAc:CHCl$_3$ to get yellow solid which was crystallized in DCM/Pet ether to yield 550 mg (86%) yellow solid. $^1$HNMR (DMSO-d$_6$, 300 MHz): δ 8.83 (d, 1H), 7.55 (s, 1H), 7.48 (d, 2H), 6.66 (d, 2H), 5.63 (bs, 2H), 4.28 (m, 1H), 3.67 (s, 3H), 1.98 (m, 1H), 0.96 (d, 6H).

Intermediate 2

Methyl 2-(5-(4-aminophenyl)thiazole-2-carboxamido)-3-methylbutanoate

A. Ethyl 5-(4-nitrophenyl)thiazole-2-carboxylate

A solution of Ethyl 2-(2-(4-nitrophenyl)-2-oxoethylamino)-2-oxoacetate (Intermediate 1, step C, 5 g) and Lawesson's reagent (7.22 g) in 1,4-Dioxane (100 ml) was refluxed for 2 hours. The reaction mixture was cooled, water was added and the mixture was neutralized with saturated solution of Na$_2$CO$_3$. This was followed by addition of EtOAc and then the layers were separated. The organic layer was dried over Na$_2$SO$_4$, filtered and concentrated under reduced pressure to get dark brown residue. The residue was chromatographed on silica gel in 0.5:9.5 EtOAc:CHCl$_3$ to get dark yellow colored solid which was crystallized in CHCl$_3$/pet ether to yield 3.65 g (73%) of the title compound. $^1$H NMR (CDCl$_3$, 300 MHz): δ 8.33 (d, 2H), 8.3 (s, 1H), 7.83 (d, 2H), 4.54 (q, 2H), 1.49 (t, 3H); MS (ES+) m/z 279 (M+1).

B. 5-(4-nitrophenyl)thiazole-2-carboxylic acid

Ethyl 5-(4-nitrophenyl)thiazole-2-carboxylate (Intermediate 2, step A, 3.6 g) was dissolved in THF (90 ml). 1 Molar aqueous NaOH (52 ml) was added and stirred at RT for 15-20 minutes. The reaction mixture was acidified with 1M HCl, extracted with EtOAc. The organic layer was washed with brine, dried over Na$_2$SO$_4$ and concentrated under reduced pressure to get pale yellow colored solid. Solid was crystallized in EtOAc/Pet ether to yield 2.48 g (76%) of the title compound. $^1$H NMR (DMSO-d$_6$, 300 MHz): δ 14.21 (bs, 1H), 8.7 (s, 1H), 8.31 (d, 2H), 8.1 (d, 2H); MS (ES+): m/z 251 (M+1).

C. Methyl 3-methyl-2-(5-(4-nitrophenyl)thiazole-2-carboxamido)butanoate

N-methyl morpholine (1.01 ml) was added to a solution of 5-(4-nitrophenyl)thiazole-2-carboxylic acid (Intermediate 2, step B, 2.3 g) in THF (72 ml). The reaction mixture was stirred for 10 minutes at RT, cooled to −20° C. Isobutyl chloroformate (1.19 ml) was added and the mixture was stirred for 15-20 minutes at −20 to −30° C. This was followed by the addition of L-valine methyl ester hydrochloride (2.15 g) previously neutralized with Et$_3$N (1.8 ml). The reaction mixture was stirred at −20 to −30° C. for 5 minutes and was then allowed to gradually warm to RT. The solvent was removed under reduced pressure and the crude material was chromatographed on silica gel in 15:85 EtOAc:CHCl$_3$ to get pale yellow colored solid which was crystallized in EtOAc/Pet ether to yield 2.25 g (67%) of the title compound. $^1$H NMR (DMSO-d$_6$, 300 MHz): δ 8.95 (d, 1H), 8.7 (s, 1H), 8.34 (d, 2H), 8.09 (d, 2H), 4.33 (m, 1H), 3.68 (s, 3H), 2.27 (m, 1H), 0.95 (t, 6H); MS (ES+): m/z 364 (M+1).

D. Methyl 2-(5-(4-aminophenyl)thiazole-2-carboxamido)-3-methylbutanoate

Ammonium chloride (1.04 g) and iron (777 mg) were added to a solution of Methyl 3-methyl-2-(5-(4-nitrophenyl)thiazole-2-carboxamido)butanoate (Intermediate 2, step C, 2.15 g) in EtOH (21.5 ml), THF (8.6 ml), and Water (8.6 ml). The reaction mixture was refluxed at 80° C. for 3 hours. It was then cooled, filtered through celite and the solvent was removed under reduced pressure to get dark brown residue. The residue was taken in water and extracted with ethyl acetate. The organic layer was separated, dried over Na$_2$SO$_4$ and concentrated to get dark brown residue which was purified by column on silica gel in 2.5:7.5 EtOAc:chloroform to get yellow sticky solid which was crystallized in DCM/pet ether to yield 1.82 g (91%) of the title compound. $^1$HNMR (DMSO-d$_6$, 300 MHz): δ 8.59 (d, 1H), 8.15 (s, 1H), 7.42 (d, 2H), 6.63 (d, 2H), 5.76 (bs, 2H), 4.31 (m, 1H), 3.67 (s, 3H), 2.27 (m, 1H), 0.91 (d, 6H); MS (ES+): m/z 334 (M+1).

Intermediate 3

Methyl-2-(4-(4-aminophenyl)thiazole-2-carboxamido)-3-methyl butanoate

A. Ethyl 4-(4-nitrophenyl)thiazole-2-carboxylate

To 2-Bromo-1-(4-nitrophenyl)ethanone (Intermediate 1, step A, 9.2 g) in methanol (200 ml) ethyl thioxamate (5.0 g) was added and the reaction mixture was refluxed for 2 hours, The reaction mixture was cooled to RT, precipitated solid was filtered and dried to obtain the title compound. Yield: 7.1 gm (67%); $^1$H NMR (CDCl$_3$; 300 MHz): δ 8.33 (d, 2H), 8.17 (d, 2H), 7.96 (s, 1H), 4.56 (q, 2H), 1.51 (t, 3H).

B. 4-(4-Nitrophenyl)thiazole-2-carboxylic acid

To ethyl 4-(4-nitrophenyl)thiazole-2-carboxylate (Intermediate 3, step A, 7.0 g) in THF (70 ml) was added (1 ml) 1N lithium hydroxide monohydrate solution and reaction mixture was stirred for 4 hours at RT. Organic solvent was concentrated, water was added, and the reaction mixture was made acidic by dilute HCl solution. This resulted in precipitation of white solid, which was filtered and washed with water. The solid was dried to obtain the title compound. Yield: 6.2 gm (98%). $^1$H NMR (DMSO-d$_6$, 300 MHz): δ 8.78 (s, 1H), 8.32 (d, 4H).

C. Methyl 3-methyl-2-(4-(4-nitrophenyl)thiazole-2-carboxamido)butanoate

N-methyl morpholine (1.8 gm) was added to a solution of 4-(4-nitrophenyl)thiazole-2-carboxylic acid (Intermediate 3, step B, 4.5 gm) in THF (300 ml). The reaction mixture was stirred for 5 minutes and then cooled to −20° C. Isobutyl chloroformate (2.45 gm) was added to it and the reaction mixture was stirred for 20 minutes. To it was added L-valine methyl ester hydrochloride (7.2 gm) previously neutralized with triethylamine (4.63 gm) and the reaction mass was stirred for 3 hours as the temperature rose to RT. Organic solvent was concentrated and compound was purified by column chromatography (silica gel, EtOAc-petroleum ether) to obtain yellow solid as title compound. Yield: 4.4 gm (67%). $^1$H NMR (DMSO-d$_6$, 300 MHz): δ 8.36 (d, 2H), 8.14 (d, 2H), 7.94 (s, 1H), 7.80 (d, 1H), 4.77 (t, 1H), 3.83 (s, 3H), 2.37 (m, 1H), 1.071 (s, 6H).

D. Methyl-2-(4-(4-aminophenyl)thiazole-2-carboxamido)-3-methyl butanoate

To methyl 3-methyl-2-(4-(4-nitrophenyl)thiazole-2-carboxamido)butanoate (Intermediate 3, step C, 4.277 gm) in EtOH (40 ml) and water (20 ml), ammonium chloride (630 mg) and iron (1.97 gm) was added and reaction mixture was refluxed at 80° C. for 3 hours. The reaction mixture was cooled to RT, filtered through celite, and evaporated to obtain brown residue, aqueous sodium bicarbonate solution was added, then ethyl acetate was added and stirred, organic layer was collected and dried over Na$_2$SO$_4$ and concentrated. The residue obtained was purified by column chromatography (silica gel, EtOAc-petroleum ether) to obtain title compound as yellow solid. Yield: 2.7 gm (68%). $^1$H NMR (DMSO-d$_6$, 300 MHz): δ 8.71 (d, 1H), 8.03 (s, 1H), 7.78 (d, 2H), 6.64 (d, 2H), 5.38 (s, 2H), 4.38 (t, 1H), 3.69 (s, 3H), 2.30 (m, 1H), 0.98 (d, 6H).

Intermediate 4

Methyl 2-(5-(4-aminophenyl)-N-methylthiazole-2-carboxamido)-3-methylbutanoate

A. Methyl 3-methyl-2-(N-methyl-5-(4-nitrophenyl) thiazole-2-carboxamido)butanoate To methyl 3-methyl-2-(5-(4-nitrophenyl)thiazole-2-carboxamido)butanoate (Intermediate 2, step C, 1 g) in DMSO (10 ml), to this cesium carbonate (1.346 gm) was added and the reaction mixture was stirred for 5 minutes. To this, methyliodide (0.258 ml) was added and the reaction mixture was stirred for 1 hour. Reaction mixture was quenched using water. The residue obtained was filtered and dried to obtain the title compound. Yield: 0.870 gm (83%); $^1$H NMR (DMSO-d$_6$, 300 MHz): δ 8.65 (s, 1H), 8.33 (d, 2H), 8.08 (d, 2H), 6.18-4.75 (d, 1H), 3.68 (s, 3H), 3.46-2.96 (s, 3H), 2.38 (m, 1H), 1.03 (d, 3H), 0.91 (d, 3H); MS (ESI) m/z 378 [M+H]$^+$, 400 [M+Na]$^+$ B. Methyl 2-(5-(4-aminophenyl)-N-methylthiazole-2-carboxamido)-3-methylbutanoate To Methyl 3-methyl-2-(N-methyl-5-(4-nitrophenyl)thiazole-2-carboxamido) butanoate (Intermediate 4, step A 0.8 gm) in ethanol (8 ml) and water (4 ml), ammonium chloride (0.113 gm) and iron (0.355 gm) was added and reaction mixture was refluxed at 80° C. for 3 hours. The reaction mixture was cooled to RT and filtered through celite. The organic solvent was concentrated to obtain brown residue, aqueous sodium bicarbonate solution was added, then ethyl acetate was added and stirred, organic layer was collected and dried over Na$_2$SO$_4$ and concentrated. The residue obtained was purified by column chromatography (silica gel, EtOAc-petroleum ether) to obtain title compound as yellow solid. Yield: 0.7 gm (95%). 1H NMR (CDCl$_3$; 300 MHz): δ 7.91 (d, 1H), 7.45 (d, 2H), 6.77 (d, 2H), 6.45-5.02 (d, 1H), 3.74 (s, 3H), 3.56-3.06 (s, 3H), 2.45 (m, 1H), 1.09 (d, 3H), 1.00 (d, 3H); MS (ESI) m/z 348.1 [M+H]$^+$, 370.1 [M+Na]$^+$ Intermediate 5

Methyl 4-(2-cyanopropan-2-yl)benzoate

A solution of methyl iodide (5.35 ml) and methyl 4-(cyanomethyl)benzoate (5 g) in THF (25 ml) was added slowly to a solution of potassium tert-butoxide (8 g) in THF (25 ml) at −30° C. in an inert atmosphere. The reaction mixture was stirred at RT for about 2 hours. It was then quenched with water (10 ml) and EtOAc was added. The organic and aqueous layers were separated. Organic layer was washed successively with water, brine and dried over sodium sulfate. Organic solvent was concentrated to obtain violet residue which was purified by silica gel column chromatography using 20% EtOAc-Petroleum ether to obtain off white solid. The off white solid was crystallized in chloroform-petroleum ether to obtain title compound as white solid. $^1$HNMR (CDCl$_3$; 300 MHz): δ 8.06 (d, 2H), 7.58 (d, 2H), 3.97 (s, 3H), 1.76 (s, 6H); MS (ESI) m/z 204.1 [M+H]$^+$.

Intermediate 6

Methyl 4-(3-cyanopentan-3-yl)benzoate

The title compound was synthesized analogous to Intermediate 5, using ethyl iodide (4.11 ml) instead of methyl iodide. $^1$HNMR (CDCl$_3$, 300 MHz): 8.08-8.06 (d, 2H), 7.5-7.47 (d, 2H), 3.94 (s, 3H), 2.15-2.03 (m, 2H), 2.0-1.89 (m, 2H), 0.91 (t, 6H); MS (ESI) m/z 232.1 [M+H]$^+$.

EXAMPLES

Example 1

Methyl 3-methyl-2-(5-(4-(3-(3-(trifluoromethyl)phenyl)ureido)phenyl)oxazole-2-carboxamido)butanoate To a solution of methyl 2-(5-(4-aminophenyl)oxazole-2-carboxamido)-3-methylbutanoate (Intermediate 1, 150 mg) in THF (3 ml) was added 1-isocyanato-3-(trifluoromethyl)benzene (132 mg) and the mixture was stirred overnight at RT. The mixture was then concentrated, purified by column chromatography (EtOAc:Pet ether, 2:8) and crystallized in CHCl$_3$/Pet ether to give the title compound. Yield: 210 mg (88%). $^1$HNMR (DMSO-d$_6$, 300 MHz): δ 9.13 (s, 1H), 9.09 (s, 1H), 8.99 (d, 1H), 8.03 (d, 1H), 7.82 (s, 1H), 7.8 (d, 2H), 7.64 (d, 2H), 7.58 (dd, 1H), 7.55 (dd, 1H), 7.34 (m, 1H), 4.3, (m, 1H), 3.68 (s, 3H), 2.24 (m, 1H), 0.95 (d, 6H); MS (ES+) m/z 505 (M+1).

Example 2

3-Methyl-2-(5-(4-(3-(3-(trifluoromethyl)phenyl)ureido)phenyl)oxazole-2-carboxamido)butanoic acid To a solution of methyl 3-methyl-2-(5-(4-(3-(3-(trifluoromethyl)phenyl)ureido)phenyl) oxazole-2-carboxamido) butanoate (Example 1, 150 mg) in THF (3 ml) was added 1 M aqueous solution of Lithium hydroxide monohydrate (0.6 ml) and the mixture was stirred for 4 hours at RT. The reaction mixture was acidified with dilute HCl and extracted with EtOAc. The organic layer was separated, dried over Na$_2$SO$_4$, concentrated under reduced pressure and then crystallized in EtOAc to give the title compound. Yield: 125 mg (85%); $^1$H NMR (DMSO-d$_6$, 300 MHz): δ 12.93 (bs, 1H), 9.14 (s, 1H), 9.06 (s, 1H), 8.64 (d, 1H), 8.03 (d, 1H), 7.81 (s, 1H), 7.8 (d, 2H), 7.64 (d, 2H), 7.58 (dd, 1H), 7.52 (dd, 1H), 7.34 (m, 1H), 4.28, (m, 1H), 2.26 (m, 1H), 0.95 (d, 6H); MS (ES+) m/z 491 (M+1).

Example 3

Methyl 2-(5-(4-(3-(2-chlorophenyl)ureido)phenyl)oxazole-2-carboxamido)-3-methylbutanoate The title compound was synthesized analogous to Example 1, using 1-chloro-2-isocyanatobenzene and intermediate 1. Yield: 79%; $^1$HNMR (DMSO-d$_6$, 300 MHz): δ 9.68 (s, 1H), 8.98 (d, 1H), 8.39 (s, 1H), 8.15 (dd, 1H), 7.82 (s, 1H), 7.78 (d, 2H), 7.63 (d, 2H), 7.48 (dd, 1H), 7.34 (m, 1H), 7.05 (m, 1H), 4.3, (m, 1H), 3.68 (s, 3H), 2.26 (m, 1H), 0.95 (d, 6H); MS (ES+) m/z 471 (M+1).

Example 4

2-(5-(4-(3-(2-Chlorophenyl)ureido)phenyl)oxazole-2-carboxamido)-3-methylbutanoic acid The title compound was synthesized analogous to Example 2, using methyl 2-(5-(4-(3-(2-chlorophenyl)ureido)phenyl) oxazole-2-carboxamido)-3-methylbutanoate. Yield: 79%; $^1$H NMR (DMSO-d$_6$, 300 MHz): δ 12.93 (bs, 1H), 9.68 (s, 1H), 8.64 (d, 1H), 8.39 (s, 1H), 8.17 (dd, 1H), 7.81 (s, 1H), 7.78 (d, 2H), 7.63 (d, 2H), 7.48 (dd, 1H), 7.34 (m, 1H), 7.05 (m, 1H), 4.28, (m, 1H), 2.3 (m, 1H), 0.95 (d, 6H); MS (ES+) m/z 455 (M−1).

Example 5

Methyl 2-(5-(4-(3-(3,4-dimethylphenyl)ureido)phenyl)oxazole-2-carboxamido)-3-methylbutanoate The title compound was synthesized analogous to Example 1, using 4-isocyanato-1,2-dimethylbenzene and intermediate 1. Yield: 82%; $^1$H NMR (DMSO-d$_6$, 300 MHz): δ 8.97 (d, 1H), 8.89 (s, 1H), 8.56 (s, 1H), 7.79 (s, 1H), 7.77 (d, 2H), 7.61 (d, 2H), 7.24 (dd, 1H), 7.19 (dd, 1H), 7.04 (d, 1H), 4.3, (m, 1H), 3.68 (s, 3H), 2.28 (m, 1H), 2.19 (s, 3H), 2.15 (s, 3H), 0.95 (d, 6H); MS (ES+): m/z 465 (M+1).

Example 6

2-(5-(4-(3-(3,4-dimethylphenyl)ureido)phenyl)oxazole-2-carboxamido)-3-methylbutanoic acid The title compound was synthesized analogous to Example 2, using methyl 2-(5-(4-(3-(3,4-dimethylphenyl)ureido)phenyl)oxazole-2-carboxamido)-3-methylbutanoate. Yield: 79%; $^1$HNMR (DMSO-d$_6$, 300 MHz): δ 12.89 (bs, 1H), 8.9 (s, 1H), 8.63 (d, 1H), 8.57 (s, 1H), 7.83 (s, 1H), 7.79 (d, 2H), 7.61 (d, 2H), 7.24 (dd, 1H), 7.16 (dd, 1H), 7.04 (d, 1H), 4.28, (m, 1H), 2.27 (m, 1H), 2.19 (s, 3H), 2.08 (s, 3H), 0.95 (d, 6H); MS (ES+) m/z 451 (M+1).

Example 7

Methyl 2-(5-(4-(3-(4-chloro-2-phenoxyphenyl)ureido)phenyl)oxazole-2-carboxamido)-3-methylbutanoate The title compound was synthesized analogous to Example 1, using 4-chloro-1-isocyanato-2-phenoxybenzene and intermediate 1. Yield 79%; $^1$HNMR (DMSO-d$_6$, 300 MHz): δ 9.61 (s, 1H), 8.99 (d, 1H), 8.74 (s, 1H), 8.4 (d, 1H), 7.8 (s, 1H), 7.77 (d, 2H), 7.6 (d, 2H), 7.44 (d, 2H), 7.22 (dd, 1H), 7.1 (d, 2H), 7.0 (dd, 1H), 6.85 (d, 1H), 4.3, (m, 1H), 3.67 (s, 3H), 2.28 (m, 1H), 0.95 (d, 6H); MS (ES+): m/z 563 (M+1).

Example 8

2-(5-(4-(3-(4-chloro-2-phenoxyphenyl)ureido)phenyl)oxazole-2-carboxamido)-3-methylbutanoic acid The title compound was synthesized analogous to Example 2, using methyl 2-(5-(4-(3-(4-chloro-2-phenoxyphenyl)ureido)phenyl)oxazole-2-carboxamido)-3-methylbutanoate. Yield: 80%; $^1$HNMR (DMSO-d$_6$, 300 MHz): δ 12.96 (bs, 1H), 8.73 (s, 1H), 8.63 (d, 1H), 8.39 (s, 1H), 7.8 (s, 1H), 7.77 (d, 2H), 7.6 (d, 2H), 7.44 (d, 2H), 7.22 (dd, 1H), 7.11 (d, 2H), 7.0 (dd, 1H), 6.85 (d, 1H), 4.28 (m, 1H), 2.23 (m, 1H), 0.97 (d, 6H); MS (ES+) m/z 549 (M+1).

Example 9

Methyl 3-methyl-2-(5-(4-(3-(3-(trifluoromethyl)phenyl)ureido)phenyl)thiazole-2-carboxamido)butanoate To a solution of methyl 2-(5-(4-aminophenyl)thiazole-2-carboxamido)-3-methylbutanoate (Intermediate 2, 120 mg) in THF (2.4 ml) was added 1-isocyanato-3-(trifluoromethyl)benzene (101 mg) and the mixture was stirred overnight at RT. The mixture was concentrated, purified by column chromatography (EtOAc:Pet ether, 2:8) and crystallized in CHCl$_3$/pet ether to give the title compound. Yield: 156 mg (83%); $^1$HNMR (DMSO-d$_6$, 300 MHz): δ 9.12 (s, 1H), 9.08 (s, 1H), 8.36 (s, 1H), 8.03 (d, 1H), 7.74 (d, 2H), 7.61 (d, 2H), 7.55 (dd, 1H), 7.5 (m, 1H), 7.32 (dd, 1H), 4.33 (m, 1H), 3.68 (s, 3H), 2.26 (m, 1H), 0.92 (d, 6H); MS (ES+): m/z 521 (M+1).

Example 10

3-methyl-2-(5-(4-(3-(3-(trifluoromethyl)phenyl)ureido)phenyl)thiazole-2-carboxamido)butanoic acid To a solution of methyl 3-methyl-2-(5-(4-(3-(3-(trifluoromethyl)phenyl)ureido)phenyl) thiazole-2-carboxamido) butanoate (Example 9, 100 mg) in THF (2 ml) was added 1 M aqueous solution of Lithium hydroxide monohydrate (0.38 ml) and the mixture was stirred at RT for 4 hours. The reaction mixture was acidified with dilute HCl and extracted with EtOAc. The organic layer was separated, dried over Na$_2$SO$_4$, concentrated under reduced pressure and then crystallized in EtOAc to give the title compound. Yield: 60 mg (62%); $^1$H NMR (DMSO-d$_6$, 300 MHz): δ 12.97 (bs, 1H), 9.18 (s, 1H), 9.13 (s, 1H), 8.37 (d, 1H), 8.36 (s, 1H), 8.03 (d, 1H), 7.71 (d, 2H), 7.61 (d, 2H), 7.55 (dd, 1H), 7.5 (dd, 1H), 7.34 (d, 1H), 4.31, (m, 1H), 2.28 (m, 1H), 0.95 (d, 6H); MS (ES+): m/z 507 (M+1).

Example 11

Methyl 2-(5-(4-(3-(2-chlorophenyl)ureido)phenyl)thiazole-2-carboxamido)-3-methylbutanoate The title compound was synthesized analogous to Example 9, using 1-chloro-2-isocyanatobenzene and intermediate 2. Yield: 87%; $^1$HNMR (DMSO-d$_6$, 300 MHz): δ 9.67 (s, 1H), 8.74 (d, 1H), 8.38 (s, 1H), 8.36 (s, 1H), 8.15 (dd, 1H), 7.75 (d, 2H), 7.6 (d, 2H), 7.49 (dd, 1H), 7.32 (m, 1H), 7.06 (m, 1H), 4.33, (m, 1H), 3.68 (s, 3H), 2.26 (m, 1H), 0.95 (d, 6H); MS (ES+): m/z 487 (M+1).

Example 12

2-(5-(4-(3-(2-Chlorophenyl)ureido)phenyl)thiazole-2-carboxamido)-3-methylbutanoic acid The title compound was synthesized analogous to Example 10, using methyl 2-(5-(4-(3-(2-chlorophenyl)ureido)phenyl)thiazole-2-carboxamido)-3-methylbutanoate. Yield: 72%; $^1$HNMR (DMSO-d$_6$, 300 MHz): δ 12.96 (bs, 1H), 8.38 (s, 1H), 8.37 (d, 1H), 8.36 (s, 1H), 8.18 (dd, 1H), 7.75 (d, 2H), 7.6 (d, 2H), 7.46 (dd, 1H), 7.32 (m, 1H), 7.05 (m, 1H), 4.31, (m, 1H), 2.28 (m, 1H), 0.95 (d, 6H); MS (ES+): m/z 473 (M+1).

Example 13

Methyl 2-(5-(4-(3-(3,4-dimethylphenyl)ureido)phenyl)oxazole-2-carboxamido)-3-methylbutanoate The title compound was synthesized analogous to Example 9, using 4-isocyanato-1,2-dimethylbenzene and intermediate 2. Yield: 82%; $^1$H NMR (DMSO-d$_6$, 300 MHz): δ 8.89 (s, 1H), 8.73 (d, 1H), 8.56 (s, 1H), 8.35 (s, 1H), 7.69 (d, 2H), 7.58 (d, 2H), 7.24 (dd, 1H), 7.19 (dd, 1H), 7.05 (d, 1H), 4.33, (m, 1H), 3.68 (s, 3H), 2.28 (m, 1H), 2.2 (s, 3H), 2.16 (s, 3H), 0.95 (d, 6H); MS (ES+) m/z 481 (M+1).

Example 14

2-(5-(4-(3-(3,4-dimethylphenyl)ureido)phenyl)oxazole-2-carboxamido)-3-methylbutanoic acid The title compound was synthesized analogous to Example 10, using methyl 2-(5-(4-(3-(3,4-dimethylphenyl)ureido)phenyl)oxazole-2-carboxamido)-3-methylbutanoate. Yield: 68%; $^1$H NMR (DMSO-d$_6$, 300 MHz): δ 12.98 (bs, 1H), 8.91 (s, 1H), 8.56 (s, 1H), 8.36 (d, 1H), 8.34 (s, 1H), 7.72 (d, 2H), 7.58 (d, 2H), 7.24 (dd, 1H), 7.17 (dd, 1H), 7.05 (d, 1H), 4.31, (m, 1H), 2.27 (m, 1H), 2.23 (s, 3H), 2.20 (s, 3H), 0.95 (d, 6H); MS (ES+) m/z 467 (M+1).

Example 15

Methyl 3-methyl-2-(5-(4-(3-(2-phenoxyphenyl)ureido)phenyl)thiazole-2-carboxamido)butanoate The title compound was synthesized analogous to Example 9, using 1-isocyanato-2-phenoxybenzene and intermediate 2. Yield: 84%; $^1$H NMR (DMSO-d$_6$, 300 MHz): δ 9.53 (s, 1H), 8.73 (d, 1H), 8.54 (s, 1H), 8.35 (s, 1H), 8.27 (dd, 1H), 7.73 (d, 2H), 7.57 (d, 2H), 7.43 (dd, 2H), 7.17 (m, 1H), 7.1 (d, 1H), 7.07 (dd, 2H), 6.98 (d, 1H), 6.86 (d, 1H), 4.32 (m, 1H), 3.68 (s, 3H), 2.28 (m, 1H), 0.94 (d, 6H); MS (ES+) m/z 545 (M+1).

Example 16

3-methyl-2-(5-(4-(3-(2-phenoxyphenyl)ureido)phenyl)thiazole-2-carboxamido)butanoic acid The title compound was synthesized analogous to Example 10, using methyl 3-methyl-2-(5-(4-(3-(2-phenoxyphenyl)ureido)phenyl)thiazole-2-carboxamido)butanoate. Yield: 51%; $^1$H NMR (DMSO-d$_6$, 300 MHz): δ 12.98 (bs, 1H), 9.53 (s, 1H), 8.54 (s, 1H), 8.37 (d, 1H), 8.34 (s, 1H), 8.3 (dd, 1H), 7.73 (d, 2H), 7.5 (d, 2H), 7.43 (dd, 2H), 7.15 (m, 2H), 7.05 (d, 2H), 7.0 (dd, 1H), 6.86 (d, 1H), 4.31 (m, 1H), 2.27 (m, 1H), 0.94 (d, 6H); MS (ES+): m/z 531 (M+1).

Example 17

Methyl 2-(5-(4-(3-(4-chloro-2-phenoxyphenyl)ureido)phenyl)thiazole-2-carboxamido)-3-methylbutanoate The title compound was synthesized analogous to Example 9, using 4-chloro-1-isocyanato-2-phenoxybenzene and intermediate 2. Yield: 60%; $^1$HNMR (DMSO-d$_6$, 300 MHz): δ 9.61 (s, 1H), 8.73 (s, 1H), 8.71 (d, 1H), 8.4 (d, 1H), 8.36 (s, 1H), 7.74 (d, 2H), 7.54 (d, 2H), 7.44 (d, 2H), 7.2 (dd, 1H), 7.11 (d, 2H), 7.03 (dd, 1H), 6.86 (d, 1H), 4.33, (m, 1H), 3.68 (s, 3H), 2.26 (m, 1H), 0.95 (d, 6H); MS (ES+) m/z 579 (M+1).

Example 18

2-(5-(4-(3-(4-chloro-2-phenoxyphenyl)ureido)phenyl)thiazole-2-carboxamido)-3-methylbutanoic acid The title compound was synthesized analogous to Example 10, using methyl 2-(5-(4-(3-(4-chloro-2-phenoxyphenyl)ureido)phenyl)thiazole-2-carboxamido)-3-methylbutanoate.

Yield: 69%; $^1$HNMR (DMSO-$d_6$, 300 MHz): δ 12.99 (bs, 1H), 9.61 (s, 1H), 8.73 (s, 1H), 8.4 (d, 1H), 8.37 (d, 1H), 8.36 (s, 1H), 7.74 (d, 2H), 7.57 (d, 2H), 7.44 (d, 2H), 7.2 (dd, 1H), 7.11 (d, 2H), 7.0 (dd, 1H), 6.86 (d, 1H), 4.31 (m, 1H), 2.27 (m, 1H), 0.94 (d, 6H); MS (ES+) m/z 563 (M−1).

Example 19

Ethyl 2-(5-(4-(6-fluorobenzo[d]thiazol-2-ylamino)phenyl)thiazole-2-carboxamido)-3-methylbutanoate A solution of Methyl 2-(5-(4-aminophenyl)thiazole-2-carboxamido)-3-methylbutanoate (Intermediate 2, 150 mg) and 2-chloro-6-fluorobenzo[d]thiazole (101 mg) in EtOH (3 ml) was heated at 55-60° C. to get clear solution. 4M aqueous HCl in 1,4-Dioxane (0.11 ml) was added to it and the reaction mixture was refluxed at 80° C. for 20 hours. The solvent was removed under reduced pressure and the residue was purified by silica gel column chromatography (EtOAc:Pet ether, 2:8). The solid was crystallized in EtOAc/pet ether to give the title compound. Yield: 120 mg (53%); $^1$HNMR (DMSO-$d_6$, 300 MHz): δ 10.76 (s, 1H), 8.66 (d, 1H), 8.37 (s, 1H), 7.88 (d, 2H), 7.80 (d, 2H), 7.77 (d, 1H), 7.64 (dd, 1H), 7.2 (m, 1H), 4.29 (m, 1H), 4.16 (q, 2H), 2.27 (m, 1H), 1.22 (t, 3H), 0.95 (d, 6H); MS (ES+) m/z 499 (M+1).

Example 20

2-(5-(4-(6-fluorobenzo[d]thiazol-2-ylamino)phenyl)thiazole-2-carboxamido)-3-methylbutanoic acid To a solution of Ethyl 2-(5-(4-(6-fluorobenzo[d]thiazol-2-ylamino)phenyl)thiazole-2-carboxamido)-3-methylbutanoate (Example 19, 80 mg) in THF (1.6 ml) was added 1 M aqueous solution of Lithium hydroxide monohydrate (0.32 ml) and the mixture was stirred at RT for 4 hours. The reaction mixture was acidified with dilute HCl and extracted with EtOAc. The organic layer was separated, dried over $Na_2SO_4$ and concentrated under reduced pressure to get yellow solid, which was crystallized in ethyl acetate to give the title compound. Yield: 58 mg (77%); $^1$HNMR (DMSO-$d_6$, 300 MHz): δ 12.99 (bs, 1H), 10.76 (s, 1H), 8.36 (s, 1H), 8.34 (d, 1H), 7.88 (d, 2H), 7.8 (d, 2H), 7.77 (d, 1H), 7.65 (dd, 1H), 7.2 (m, 1H), 4.32, (m, 1H), 2.27 (m, 1H), 0.97 (d, 6H); MS (ES+): m/z 471 (M+1).

Example 21

Methyl 2-(5-(4-(4-tert-butylbenzamido)phenyl)thiazole-2-carboxamido)-3-methylbutanoate Pyridine (0.11 ml) was added to a solution of methyl 2-(5-(4-aminophenyl)thiazole-2-carboxamido)-3-methylbutanoate (Intermediate 2, 150 mg) in DCM (3 ml) and the reaction mixture was stirred for 5 minutes. 4-tert-butylbenzoyl chloride (0.125 ml) was then added and the reaction mixture was stirred for 1 h. The reaction mass was quenched with water. The organic layer was dried over $Na_2SO_4$ and evaporated under reduced pressure to get dark brown solid which was purified by silica gel column chromatography (EtOAc:CHCl$_3$, 2:8) to get off white solid. The solid was crystallized in CHCl$_3$/pet ether to give the title compound. Yield: 160 mg (72%) white solid. $^1$HNMR (DMSO-$d_6$, 300 MHz): δ 10.38 (s, 1H), 8.76 (d, 1H), 8.41 (s, 1H), 7.94 (d, 2H), 7.91 (d, 2H), 7.8 (d, 2H), 7.58 (d, 2H), 4.33 (m, 1H), 3.69 (s, 3H), 2.27 (m, 1H), 0.95 (d, 6H); MS (ES+): m/z 494 (M+1).

Example 22

2-(5-(4-(4-tert-butylbenzamido)phenyl)thiazole-2-carboxamido)-3-methylbutanoic acid To a solution of methyl 2-(5-(4-(4-tert-butylbenzamido)phenyl)thiazole-2-carboxamido)-3-methylbutanoate (110 mg) in THF (2.2 ml) was added 1 M aqueous solution of Lithium hydroxide monohydrate (0.44 ml) and the reaction mixture was stirred at RT for 4 hours. The reaction mixture was acidified with dilute HCl and extracted with EtOAc. The organic layer was separated, dried over $Na_2SO_4$, concentrated under vacuum to get off white solid which was crystallized in EtOAc to give the title compound. Yield: 87 mg (81%); $^1$H NMR (DMSO-$d_6$, 300 MHz): δ 13.02 (bs, 1H), 10.38 (s, 1H), 8.4 (s, 1H), 8.36 (d, 1H), 7.94 (d, 2H), 7.91 (d, 2H), 7.8 (d, 2H), 7.58 (d, 2H), 4.32 (m, 1H), 2.26 (m, 1H), 0.95 (d, 6H); MS (ES+) m/z 480 (M+1).

Example 23

Methyl 2-(4-(4-(3-(2-chlorophenyl)ureido)phenyl)thiazole-2-carboxamido)-3-methylbutanoate To methyl-2-(4-(4-aminophenyl)thiazole-2-carboxamido)-3-methylbutanoate (Intermediate 3, 170 mg) in THF (2 ml), 2-chlorophenyl isocyanate (94 mg) was added and reaction mixture was stirred for 16 hours. Organic solvent was concentrated obtained sticky solid, was purified by column chromatography (silica gel, EtOAc-petroleum ether) to obtain title compound as solid. Yield: 190 mg (76%). $^1$H NMR (DMSO-$d_6$, 300 MHz): δ 9.58 (s, 1H), 8.80 (d, 1H), 8.34 (s, 1H), 8.31 (s, 1H), 8.17 (d, 1H), 8.05 (d, 2H), 7.58 (d, 2H), 7.46 (d, 1H), 7.32 (t, 1H), 7.05 (t, 1H), 4.38 (t, 1H), 3.68 (s, 3H), 2.32 (m, 1H), 0.98 (t, 6H).

Example 24

2-(4-(4-(3-(2-Chlorophenyl)ureido)phenyl)thiazole-2-carboxamido)-3-methylbutanoic acid To methyl 2-(4-(4-(3-(2-chlorophenyl)ureido)phenyl)thiazole-2-carboxamido)-3-methylbutanoate (Example 23, 120 mg) in THF (2 ml), 1N lithium hydroxide monohydrate (1.2 ml) was added and reaction mixture was stirred for 16 hours at RT. Organic solvent was concentrated and added water, dilute HCl was added under stirring to pH acidic. The reaction mixture was filtered, and the residue was washed by water, and dried. The residue was dissolved in acetone, pet ether was added, solid was filtered and dried obtain title compound as solid. Yield: 70 mg (60%). $^1$H NMR (DMSO-$d_6$, 300 MHz): δ 12.98 (bs, 1H), 9.59 (s, 1H), 8.48 (d, 1H), 8.35 (s, 1H), 8.30 (s, 1H), 8.17 (d, 1H), 8.03 (d, 2H), 7.58 (d, 2H), 7.46 (d, 1H), 7.30 (t, 1H), 7.02 (t, 1H), 4.33 (s, 1H), 2.26 (s, 1H), 0.98 (d, 6H).

Example 25

Methyl 2-(4-(4-(6-fluorobenzo[d]thiazol-2-ylamino) phenyl)thiazole-2-carboxamido)-3-methylbutanoate To methyl-2-(4-(4-aminophenyl)thiazole-2-carboxamido)-3-methylbutanoate (Intermediate 3, 300 mg) in n-butanol (5 ml), 2-chloro-6-fluorobenzo[d]thiazole (202 mg) was added and the reaction mixture was heated at 70° C. and stirred for 10 minutes. 4M HCl in dioxane (0.131 gm) was added and the reaction mixture was stirred for 16 hours at 90° C. Organic solvent was concentrated to obtain a sticky solid, which was purified by column chromatography (silica gel, EtOAc-petroleum ether) to obtain title compound as solid. Yield: 130 mg (29%). $^1$H NMR (CDCl$_3$; 300 MHz): δ 7.97 (d, 2H), 7.83 (d, 1H), 7.67 (s, 1H), 7.64 (m, 4H), 7.38 (dd, 1H), 7.13 (td, 1H), 4.77 (q, 1H), 3.80 (s, 3H), 2.37 (m, 1H), 0.97 (dd, 6H).

Example 26

2-(4-(4-(6-fluorobenzo[d]thiazol-2-ylamino)phenyl) thiazole-2-carboxamido)-3-methylbutanoic acid The title compound was prepared from methyl 2-(4-(4-(6-fluorobenzo[d]thiazol-2-ylamino)phenyl)thiazole-2-carboxamido)-3-methylbutanoate as set forth in Example 24 and was obtained in 68% yield. $^1$H NMR (DMSO-d$_6$, 300 MHz): δ 10.71 (s, 1H), 8.42 (d, 1H), 8.29 (s, 1H), 8.06 (d, 2H), 7.89 (d, 2H), 7.75 (d, 1H), 7.60 (bs, 1H), 7.19 (t, 1H), 4.24 (s, 1H), 2.27 (s, 1H), 0.96 (d, 6H).

Example 27

Methyl 2-(4-(4-(4-tert-butylbenzamido)phenyl)thiazole-2-carboxamido)-3-methylbutanoate Pyridine (0.22 ml) was added to methyl-2-(4-(4-aminophenyl)thiazole-2-carboxamido)-3-methylbutanoate (Intermediate 3, 300 mg) in DCM (4 ml) and the reaction mixture was stirred for 5 minutes. 4-tert-butyl benzoyl chloride (230 mg) was added and reaction mixture was stirred for 16 hours at RT. Organic solvent was concentrated to obtain a sticky solid, which was purified by column chromatography (silica gel, EtOAc-petroleum ether) to obtain title compound as solid. Yield: 235 mg (53%). $^1$H NMR (DMSO-d$_6$, 300 MHz): δ 10.31 (s, 1H), 8.83 (d, 1H), 8.36 (s, 1H), 8.10 (d, 2H), 7.91 (dd, 4H), 7.56 (d, 2H), 4.38 (t, 1H), 3.68 (s, 3H), 2.35 (m, 1H), 1.31 (s, 9H), 0.98 (t, 6H).

Example 28

2-(4-(4-(4-tert-butylbenzamido)phenyl)thiazole-2-carboxamido)-3-methylbutanoic acid The title compound was prepared from methyl 2-(4-(4-(4-tert-butylbenzamido)phenyl) thiazole-2-carboxamido)-3-methylbutanoate as set forth in Example 24 and was obtained in 85% yield. $^1$H NMR (DMSO-d$_6$, 300 MHz): δ 10.31 (s, 1H), 8.53 (d, 1H), 8.35 (s, 1H), 8.08 (d, 2H), 7.91 (d, 4H), 7.55 (d, 2H), 4.35 (t, 1H), 2.31 (m, 1H), 1.31 (s, 9H), 0.98 (d, 6H).

Example 29

Methyl-3-methyl-2-(4-(4-(3-(4-(trifluoromethyl) phenyl)ureido)phenyl) thiazole-2-carboxamido)butanoate The title compound was synthesized analogous to Example 23, using 1-isocyanato-4-(trifluoromethyl)benzene and intermediate 3. Yield: 79%; $^1$H NMR (DMSO-d$_6$, 300 MHz): δ 9.14 (s, 1H), 8.99 (s, 1H), 8.80 (d, 1H), 8.32 (s, 1H), 8.06 (d, 2H), 7.66 (bs, 4H), 7.61 (d, 2H), 4.37 (s, 1H), 3.70 (s, 3H), 2.32 (m, 1H), 0.97 (s, 6H).

Example 30

3-methyl-2-(4-(4-(3-(4-(trifluoromethyl)phenyl)ureido)phenyl)thiazole-2-carboxamido)butanoic acid The title compound was prepared from methyl-3-methyl-2-(4-(4-(3-(4-(trifluoromethyl)phenyl)ureido)phenyl)thiazole-2-carboxamido)butanoate as set forth in Example 24 and was obtained in 72% yield. $^1$H NMR (DMSO-d$_6$, 300 MHz): δ 13.03 (bs, 1H), 9.18 (s, 1H), 9.03 (s, 1H), 8.50 (d, 1H), 8.32 (s, 1H), 8.04 (d, 2H), 7.66 (bs, 4H), 7.61 (d, 2H), 4.35 (s, 1H), 2.30 (m, 1H), 0.99 (d, 6H).

Example 31

Methyl 2-(4-(4-(3-(3,4-dimethylphenyl)ureido)phenyl)thiazole-2-carboxamido)-3-methylbutanoate The title compound was synthesized analogous to Example 23, using 4-isocyanato-1,2-dimethylbenzene and intermediate 3. Yield: 75%; $^1$H NMR (DMSO-d$_6$, 300 MHz): δ 8.80 (s, 2H), 8.51 (s, 1H), 8.30 (s, 1H), 8.03 (d, 2H), 7.57 (d, 2H), 7.24 (s, 1H), 7.19 (d, 1H), 7.07 (d, 1H), 4.39 (t, 1H), 3.70 (s, 3H), 2.31 (m, 1H), 2.19 (s, 3H), 2.16 (s, 3H), 0.97 (t, 6H).

Example 32

2-(4-(4-(3-(3,4-Dimethylphenyl)ureido)phenyl)thiazole-2-carboxamido)-3-methylbutanoic acid The title compound was prepared from methyl 2-(4-(4-(3-(3,4-dimethylphenyl)ureido)phenyl)thiazole-2-carboxamido)-3-methylbutanoate as set forth in Example 24 and was obtained in 88% yield. $^1$H NMR (DMSO-d$_6$, 300 MHz): δ 13.01 (bs, 1H), 8.81 (s, 1H), 8.52 (s, 1H), 8.48 (d, 1H), 8.28 (s, 1H), 7.99 (d, 2H), 7.56 (d, 2H), 7.22 (s, 1H), 7.17 (dd, 1H), 7.02 (d, 1H), 4.35 (t, 1H), 2.32 (m, 1H), 2.18 (s, 3H), 2.14 (s, 3H), 0.97 (d, 6H).

Example 33

Methyl 2-(4-(4-(3-(4-chloro-2-phenoxyphenyl)ureido)phenyl)thiazole-2-carboxamido)-3-methylbutanoate The title compound was synthesized analogous to Example 23, using 4-chloro-1-isocyanato-2-phenoxybenzene and intermediate 3. Yield: 61%; $^1$H NMR (DMSO-d$_6$, 300 MHz): δ 9.54 (s, 1H), 8.81 (d, 1H), 8.71 (s, 1H), 8.41 (s, 1H), 8.32 (s, 1H), 8.06 (d, 2H), 7.57 (d, 2H), 7.44 (d, 2H), 7.22 (t, 1H), 7.11 (d, 2H), 7.02 (d, 1H), 6.86 (d, 1H), 4.39 (t, 1H), 3.69 (s, 3H), 2.31 (m, 1H), 0.99 (d, 6H).

Example 34

2-(4-(4-(3-(4-chloro-2-phenoxyphenyl)ureido)phenyl)thiazole-2-carboxamido)-3-methylbutanoic acid The title compound was prepared from methyl 2-(4-(4-(3-(4-chloro-2-phenoxyphenyl)ureido)phenyl)thiazole-2-carboxamido)-3-methylbutanoate as set forth in Example 24 and was obtained in 93% yield. $^1$H NMR (DMSO-d$_6$, 300 MHz):

δ 12.97 (bs, 1H), 9.54 (s, 1H), 8.71 (s, 1H), 8.48 (d, 1H), 8.39 (d, 1H), 8.30 (s, 1H), 8.02 (d, 2H), 7.56 (d, 2H), 7.45 (t, 2H), 7.20 (t, 1H), 7.09 (d, 2H), 7.00 (dd, 1H), 6.84 (d, 1H), 4.34 (t, 1H), 2.30 (m, 1H), 0.97 (d, 6H).

Example 35

Methyl 2-(4-(4-biphenyl-4-ylcarboxamidophenyl) thiazole-2-carboxamido)-3-methylbutanoate The title compound was synthesized analogous to Example 27, using biphenyl-4-carbonyl chloride and intermediate 3. Yield: 61%; $^1$H NMR (DMSO-$d_6$, 300 MHz): δ 10.45 (s, 1H), 8.86 (d, 1H), 8.39 (s, 1H), 8.14 (m, 4H), 7.97 (d, 2H), 7.87 (d, 2H), 7.79 (d, 2H), 7.52 (t, 2H), 7.46 (d, 1H), 4.40 (t, 1H), 3.70 (s, 3H), 2.32 (m, 1H), 1.01 (t, 6H).

Example 36

2-(4-(4-Biphenyl-4-ylcarboxamidophenyl)thiazole-2-carboxamido)-3-methylbutanoic acid The title compound was prepared from methyl 2-(4-(4-biphenyl-4-ylcarboxamidophenyl) thiazole-2-carboxamido)-3-methylbutanoate as set forth in Example 24 and was obtained in 80% yield. $^1$H NMR (DMSO-$d_6$, 300 MHz): δ 10.48 (s, 1H), 8.37 (d, 1H), 8.31 (s, 1H), 8.10 (d, 2H), 8.03 (d, 2H), 7.95 (d, 2H), 7.84 (d, 2H), 7.76 (d, 2H), 7.52 (t, 2H), 7.43 (d, 1H), 3.97 (s, 1H), 2.20 (s, 1H), 0.90 (d, 6H).

Example 37

Methyl 3-methyl-2-(4-(4-(4-pentylbenzamido)phenyl)thiazole-2-carboxamido)butanoate The title compound was synthesized analogous to Example 27, using 4-pentylbenzoyl chloride and intermediate 3. Yield: 56%; $^1$H NMR (DMSO-$d_6$, 300 MHz): δ 10.32 (s, 1H), 8.84 (d, 1H), 8.37 (s, 1H), 8.12 (d, 2H), 7.91 (bs, 4H), 7.37 (d, 2H), 4.37 (t, 1H), 3.70 (s, 3H), 2.66 (s, 2H), 2.32 (m, 1H), 1.61 (s, 2H), 1.29 (s, 4H), 0.98 (t, 6H), 0.87 (s, 3H).

Example 38

3-Methyl-2-(4-(4-(4-pentylbenzamido)phenyl)thiazole-2-carboxamido) butanoic acid The title compound was prepared from methyl 3-methyl-2-(4-(4-(4-pentylbenzamido)phenyl)thiazole-2-carboxamido)butanoate as set forth in Example 24 and was obtained in 98% yield. $^1$H NMR (DMSO-$d_6$, 300 MHz): δ 13.00 (bs, 1H), 10.29 (s, 1H), 8.51 (d, 1H), 8.35 (s, 1H), 8.07 (d, 2H), 7.89 (bs, 4H), 7.35 (d, 2H), 4.33 (s, 1H), 2.75 (s, 2H), 2.28 (d, 1H), 1.59 (s, 2H), 1.28 (s, 4H), 0.97 (d, 6H), 0.85 (s, 3H).

Example 39

Methyl 3-methyl-2-(N-methyl-5-(4-(4-pentylbenzamido)phenyl)thiazole-2-carboxamido)butanoate The title compound was synthesized analogous to Example 27, using 4-pentylbenzoyl chloride and intermediate 4. Yield: 59%; $^1$H NMR (DMSO-$d_6$, 300 MHz): δ 10.38 (s, 1H), 8.86 (d, 1H), 7.95 (m, 4H), 7.78 (d, 2H), 7.37 (d, 2H), 6.04-4.76 (d, 1H), 3.68 (s, 3H), 3.47-2.95 (s, 3H), 2.68 (t, 2H), 2.38 (m, 1H), 1.63 (m, 2H), 1.30 (m, 4H), 1.03 (m, 3H), 0.90 (dd, 6H); MS (ESI) m/z 522.2 [M+H]$^+$.

Example 40

3-Methyl-2-(N-methyl-5-(4-(4-pentylbenzamido) phenyl)thiazole-2-carboxamido)butanoic acid The title compound was prepared from methyl 3-methyl-2-(N-methyl-5-(4-(4-pentylbenzamido)phenyl)thiazole-2-carboxamido)butanoate as set forth in Example 24 and was obtained in 72% yield. $^1$H NMR (DMSO-$d_6$, 300 MHz): δ 12.99 (bs, 1H), 10.38 (s, 1H), 8.36 (s, 1H), 7.92 (m, 4H), 7.78 (d, 2H), 7.37 (d, 2H), 6.06-4.68 (d, 1H), 3.45-2.94 (s, 3H), 2.68 (t, 2H), 2.32 (m, 1H), 1.63 (t, 2H), 1.30 (bs, 4H), 1.03 (bs, 3H), 0.88 (dd, 6H); MS (ESI) m/z 508.1 [M+H]$^+$.

Example 41

Methyl 2-(5-(4-biphenyl-4-ylcarboxamidophenyl)-N-methylthiazole-2-carboxamido)-3-methylbutanoate The title compound was synthesized analogous to Example 27, using biphenyl-4-carbonyl chloride and intermediate 4. Yield: 20%; $^1$HNMR (DMSO-$d_6$, 300 MHz): δ 10.52 (s, 1H), 8.88 (d, 1H), 8.10 (d, 2H), 7.97 (d, 2H), 7.87 (d, 2H), 7.80 (dd, 4H), 7.54 (t, 2H), 7.46 (1H), 6.28-4.76 (d, 1H), 3.69 (s, 3H), 3.47-2.95 (s, 3H), 2.38 (m, 1H), 1.03 (m, 3H), 0.91 (m, 3H); MS (ESI) m/z 528.2 [M+H]$^+$.

Example 42

2-(5-(4-Biphenyl-4-ylcarboxamidophenyl)-N-methylthiazole-2-carboxamido)-3-methylbutanoic acid The title compound was prepared from methyl 2-(5-(4-biphenyl-4-yl carboxamidophenyl)-N-methylthiazole-2-carboxamido)-3-methylbutanoate as set forth in Example 24 and was obtained in 66% yield. $^1$HNMR (DMSO-$d_6$, 300 MHz): δ 10.52 (s, 1H), 8.37 (s, 1H), 8.09 (d, 2H), 7.94 (s, 2H), 7.87 (d, 2H), 7.78 (bs, 4H), 7.52 (s, 2H), 7.46 (1H), 6.02-4.68 (d, 1H), 3.45-2.94 (s, 3H), 2.30 (s, 1H), 1.04 (s, 3H), 0.89 (s, 3H); MS (ESI) m/z 514.1 [M+H]$^+$, 536.1 [M+Na]$^+$.

Example 43

Methyl 2-(5-(4-(4-tert-butylbenzamido)phenyl)-N-methylthiazole-2-carboxamido)-3-methylbutanoate The title compound was synthesized analogous to Example 27, using 4-tert-butylbenzoyl chloride and intermediate 4. Yield: 56%; $^1$H NMR (DMSO-$d_6$, 300 MHz): δ 10.38 (s, 1H), 8.37 (s, 1H), 8.04 (m, 4H), 7.78 (d, 2H), 7.57 (d, 2H), 6.27-4.76 (d, 1H), 3.69 (s, 3H), 3.47-2.95 (s, 3H), 2.35 (m, 1H), 1.33 (s, 9H), 1.11 (bs, 3H), 0.90 (bs, 3H); MS (ESI): m/z 508.2 [M+H]$^+$.

Example 44

2-(5-(4-(4-tert-Butylbenzamido)phenyl)-N-methylthiazole-2-carboxamido)-3-methylbutanoic acid The title compound was prepared from methyl 2-(5-(4-(4-tert-butylbenzamido)phenyl)-N-methylthiazole-2-carboxamido)-3-methylbutanoate as set forth in Example 24 and was obtained in 85% yield. $^1$H NMR (DMSO-$d_6$, 300 MHz): δ 12.98 (bs, 1H), 10.38 (s, 1H), 8.37 (s, 1H), 7.90 (s, 4H), 7.65

(d, 2H), 7.57 (d, 2H), 6.10-4.68 (d, 1H), 3.45-2.94 (s, 3H), 2.29 (s, 1H), 1.32 (s, 9H), 1.03 (bs, 3H), 0.89 (bs, 3H); MS (ESI) m/z 494. [M+H]$^+$.

Example 45

Methyl 2-(4-(4-(2,4-dichlorophenylsulfonamido) phenyl)thiazole-2-carboxamido)-3-methylbutanoate Pyridine (1.5 ml) was added to a solution of methyl-2-(4-(4-aminophenyl)thiazole-2-carboxamido)-3-methylbutanoate (Intermediate 3, 160 mg) in DCM (4 ml), and reaction mixture was stirred for 5 minutes. 2,4 dichloro benzenesulfonyl chloride (130 mg) was added and reaction mixture was stirred for 16 hours at RT. Organic solvent was concentrated to obtain sticky solid, was purified by column chromatography (silica gel, EtOAc-petroleum ether) to obtain title compound as solid. Yield: 215 mg (82%); $^1$H NMR (CDCl$_3$, 300 MHz): δ 7.97 (d, 1H), 7.81 (d, 2H), 7.75 (d, 1H), 7.63 (s, 1H), 7.51 (d, 1H), 7.33 (dd, 1H), 7.21 (d, 2H), 7.13 (bs, 1H), 4.73 (m, 1H), 3.78 (s, 3H), 2.32 (m, 1H), 1.04 (dd, 6H); MS (ESI) m/z 542.0 [M+H]$^+$.

Example 46

2-(4-(4-(2,4-Dichlorophenylsulfonamido)phenyl) thiazole-2-carboxamido)-3-methylbutanoic acid The title compound was prepared from methyl 2-(4-(4-(2,4-dichlorophenylsulfonamido) phenyl)thiazole-2-carboxamido)-3-methylbutanoate as set forth in Example 24 and was obtained in 66% yield. $^1$H NMR (CDCl$_3$, 300 MHz): δ 8.00 (d, 1H), 7.80 (d, 3H), 7.74 (d, 1H), 7.63 (s, 1H), 7.49 (d, 1H), 7.33 (dd, 1H), 7.22 (d, 2H), 4.80 (m, 1H), 2.42 (m, 1H), 1.08 (dd, 6H); MS (ESI) m/z 528.0 [M+H]$^+$.

Example 47

Methyl 2-(5-(4-biphenyl-4-ylcarboxamidophenyl) thiazole-2-carboxamido)-3-methylbutanoate The title compound was synthesized analogous to Example 27, using biphenyl-4-carbonyl chloride and intermediate 2. Yield: 54%; $^1$H NMR (DMSO-d$_6$, 300 MHz): δ 10.50 (s, 1H), 8.75 (d, 1H), 8.41 (s, 1H), 8.10 (d, 2H), 7.97 (d, 2H), 7.87 (m, 6H), 7.54 (t, 2H), 7.45 (t, 1H), 4.36 (t, 1H), 3.68 (s, 3H), 2.31 (m, 1H), 0.97 (t, 6H); MS (ESI) m/z 514.1 [M+H]$^+$.

Example 48

2-(5-(4-biphenyl-4-ylcarboxamidophenyl)thiazole-2-carboxamido)-3-methylbutanoic acid The title compound was prepared from methyl 2-(5-(4-biphenyl-4-ylcarboxamidophenyl) thiazole-2-carboxamido)-3-methylbutanoate as set forth in Example 24 and was obtained in 82% yield. $^1$H NMR (DMSO-d$_6$, 300 MHz): δ 13.00 (bs, 1H), 10.50 (s, 1H), 8.40 (s, 1H), 8.39 (d, 1H), 8.10 (d, 2H), 7.97 (d, 2H), 7.87 (m, 6H), 7.54 (t, 2H), 7.45 (t, 1H), 4.34 (m, 1H), 2.32 (m, 1H), 0.97 (d, 6H); MS (ESI) m/z 500.1 [M+H]$^+$.

Example 49

Methyl 2-(5-(4-(3-cyclohexylpropanamido)phenyl) thiazole-2-carboxamido)-3-methylbutanoate The title compound was synthesized analogous to Example 27, using 3-cyclohexylpropanoyl chloride and intermediate 2. Yield: 49%; $^1$H NMR (DMSO-d$_6$, 300 MHz): δ 10.09 (s, 1H), 8.74 (d, 1H), 8.35 (s, 1H), 7.71 (s, 4H), 4.32 (t, 1H), 3.69 (s, 3H), 2.36 (t, 2H), 2.30 (m, 1H), 1.73 (m, 5H), 1.51 (q, 2H), 1.17 (m, 4H), 0.96 (t, 6H), 0.92 (m, 2H); MS (ESI) m/z 472.0 [M+H]$^+$.

Example 50

2-(5-(4-(3-cyclohexylpropanamido)phenyl)thiazole-2-carboxamido)-3-methylbutanoic acid The title compound was prepared from methyl 2-(5-(4-(3-cyclohexylpropanamido) phenyl)thiazole-2-carboxamido)-3-methylbutanoate as set forth in Example 24 and was obtained in 76% yield. $^1$H NMR (DMSO-d$_6$, 300 MHz): δ 13.01 (bs, 1H), 10.08 (s, 1H), 8.36 (d, 1H), 8.34 (s, 1H), 7.71 (s, 4H), 4.32 (m, 1H), 2.36 (t, 2H), 2.29 (m, 1H), 1.73 (m, 5H), 1.54 (q, 2H), 1.25 (m, 4H), 0.96 (t, 6H), 0.91 (m, 2H); MS (ESI) m/z 458.0 [M+H]$^+$.

Example 51

Methyl 2-(5-(4-(2,3-dihydro-1H-indene-2-carboxamido)phenyl)thiazole-2-carboxamido)-3-methylbutanoate The title compound was synthesized analogous to Example 27, using 2,3-dihydro-1H-indene-2-carbonyl chloride and intermediate 2. Yield: 18%; $^1$H NMR (DMSO-d$_6$, 300 MHz): δ 10.28 (s, 1H), 8.75 (d, 1H), 8.37 (s, 1H), 7.75 (s, 4H), 7.25 (m, 2H), 7.16 (m, 2H), 4.35 (t, 1H), 3.68 (s, 3H), 3.43 (m, 1H), 3.19 (d, 4H), 2.28 (m, 1H), 0.96 (t, 6H); MS (ESI) m/z 487.0 [M+H]$^+$.

Example 52

2-(5-(4-(2,3-dihydro-1H-indene-2-carboxamido) phenyl)thiazole-2-carboxamido)-3-methylbutanoic acid The title compound was prepared from methyl 2-(5-(4-(2,3-dihydro-1H-indene-2-carboxamido)phenyl)thiazole-2-carboxamido)-3-methylbutanoate as set forth in Example 24 and was obtained in 74% yield. $^1$HNMR (DMSO-d$_6$, 300 MHz): δ 12.97 (bs, 1H), 10.28 (s, 1H), 8.39 (d, 2H), 7.75 (s, 4H), 7.25 (m, 2H), 7.16 (m, 2H), 4.32 (m, 1H), 3.46 (m, 1H), 3.17 (d, 4H), 2.29 (m, 1H), 0.96 (d, 6H); MS (ESI) m/z 464.2 [M+H]$^+$.

Example 53

Methyl 2-(5-(4-(4,4-difluorocyclohexanecarboxamido)phenyl)thiazole-2-carboxamido)-3-methylbutanoate The title compound was synthesized analogous to Example 27, using 4,4-difluorocyclohexanecarbonyl chloride and intermediate 3. Yield: 62%; $^1$HNMR (DMSO-d$_6$, 300 MHz): δ 10.18 (s, 1H), 8.73 (d, 1H), 8.36 (s, 1H), 7.72 (s, 4H), 4.35 (t, 1H), 3.68 (s, 3H), 2.28 (m, 1H), 2.13 (m, 2H), 1.94 (m, 4H), 1.80 (m, 3H), 0.96 (t, 6H); MS (ESI) m/z 480 [M+H]$^+$.

Example 54

2-(5-(4-(4,4-difluorocyclohexanecarboxamido)phenyl)thiazole-2-carboxamido)-3-methylbutanoic acid The title compound was prepared from methyl 2-(5-(4-(4,4-difluorocyclohexane carboxamido)phenyl)thiazole-2-carboxamido)-3-methylbutanoate as set forth in Example 24 and was obtained in 88% yield. ¹H NMR (DMSO-d₆, 300 MHz): δ 12.99 (bs, 1H), 10.19 (s, 1H), 8.36 (s, 2H), 7.72 (s, 4H), 4.31 (t, 1H), 2.27 (m, 1H), 2.08 (m, 3H), 1.95 (m, 3H), 1.80 (m, 3H), 0.96 (d, 6H); MS (ESI) m/z 466.0 [M+H]⁺.

Example 55

(S)-methyl 2-(5-(4-(3-(2,3-dihydro-1H-inden-5-yl) ureido)phenyl)oxazole-2-carboxamido)-3-methylbutanoate The title compound was synthesized analogous to Example 1, using 5-isocyanato-2,3-dihydro-1H-indene (84.87 mg, 0.533 mmol) and intermediate 1. Yield: 92%; ¹H NMR (DMSO-d₆, 300 MHz): δ 9.005-8.978 (d, 1H), 8.912 (s, 1H), 8.624 (s, 1H), 7.804 (s, 1H), 7.781-7.752 (d, J=8.7 Hz, 2H), 7.617-7.587 (d, J=9 Hz, 2H), 7.395 (s, 1H), 7.172-7.106 (m, 2H), 4.328-4.277 (m, 1H), 3.681 (s, 3H), 2.860-2.772 (m, 4H), 2.286-2.217 (m, 1H), 2.052-2.154 (m, 2H), 0.980-0.928 (d, J=6.9 Hz, 6H); MS (ESI) m/z 475 [M−H], 477 [M+H]⁺.

Example 56

(S)-2-(5-(4-(3-(2,3-dihydro-1H-inden-5-yl)ureido) phenyl)oxazole-2-carboxamido)-3-methylbutanoic acid The title compound was synthesized analogous to Example 2, using methyl 2-(5-(4-(3-(2,3-dihydro-1H-inden-5-yl)ureido)phenyl)oxazole-2-carboxamido)-3-methylbutanoate. Yield: 87%; ¹H NMR (DMSO-d₆, 300 MHz): δ 12.942 (s, 1H), 8.924 (s, 1H), 8.655-8.634 (d, 2H), 7.797 (s, 1H), 7.781-7.752 (d, J=8.7 Hz, 2H), 7.616-7.587 (d, J=8.7 Hz, 2H), 7.396 (s, 1H), 7.172-7.105 (m, 2H), 4.306-4.256 (dd, J=1.5, 6.6 Hz, 1H), 2.859-2.771 (m, 4H), 2.279-2.212 (m, 1H), 2.051-1.953 (m, 2H), 0.975-0.952 (d, J=6.9 Hz, 6H); MS (ESI) m/z 461 (M−H), 463 (M+H).

Example 57

(S)-Methyl 2-(5-(4-(3-(4-chlorophenyl)ureido)phenyl)oxazole-2-carboxamido)-3-methylbutanoate The title compound was synthesized analogous to Example 1, using 1-chloro-4-isocyanatobenzene (0.533 mmol) and intermediate 1. ¹H NMR (DMSO-d₆, 300 MHz): δ 9.011-8.983 (d, 2H), 8.919 (s, 1H), 7.813 (s, 1H), 7.792-7.763 (d, J=8.7 Hz, 2H), 7.624-7.595 (d, J=8.7 Hz, 2H), 7.518-7.488 (d, J=9 Hz, 2H), 7.357-7.327 (d, J=9 Hz, 2H), 4.327-4.276 (m, 1H), 3.680 (s, 3H), 2.285-2.216 (m, 1H), 0.979-0.957 (d, J=6.6 Hz, 6H); MS (ESI) m/z 471 (M+H)⁺.

Example 58

(S)-2-(5-(4-(3-(4-chlorophenyl)ureido)phenyl)oxazole-2-carboxamido)-3-methylbutanoic acid The title compound was synthesized analogous to Example 2, using (S)-Methyl 2-(5-(4-(3-(4-chlorophenyl)ureido)phenyl)oxazole-2-carboxamido)-3-methylbutanoate.
¹H NMR (DMSO-d₆, 300 MHz): δ 12.940 (s, 1H), 9.056 (s, 1H), 8.965 (s, 1H), 8.659-8.631 (d, 1H), 7.807 (s, 1H), 7.792-7.763 (d, J=8.7 Hz, 2H), 7.624-7.595 (d, J=8.7 Hz, 2H), 7.519-7.489 (d, J=9 Hz, 2H), 7.356-7.327 (d, J=8.7 Hz, 2H), 4.304-4.255 (dd, J=1.5, 6.6 Hz, 1H), 2.278-2.211 (m, 1H), 0.974-0.951 (d, J=6.9 Hz, 6H); MS (ESI) m/z 455 [M−H], 457 [M+H]⁺.

Example 59

(S)-methyl 2-(5-(4-(3-(3-chlorophenyl)ureido)phenyl)oxazole-2-carboxamido)-3-methylbutanoate The title compound was synthesized analogous to Example 1, using 1-chloro-3-isocyanatobenzene (0.533 mmol) and intermediate 1. ¹H NMR (DMSO-d₆, 300 MHz): δ 9.056 (s, 1H), 9.013-8.986 (d, 2H), 7.820 (s, 1H), 7.799-7.770 (d, J=8.7 Hz, 2H), 7.728-7.704 (m, 1H), 7.631-7.601 (d, J=9 Hz, 2H), 7.347-7.268 (m, 2H), 7.059-7.024 (m, 1H), 4.328-4.277 (m, 1H), 3.680 (s, 3H), 2.286-2.218 (m, 1H), 0.980-0.958 (d, J=6.6 Hz, 6H); MS (ESI) m/z 469 (M−H), 470 (M+H)⁺.

Example 60

(S)-2-(5-(4-(3-(3-chlorophenyl)ureido)phenyl)oxazole-2-carboxamido)-3-methylbutanoic acid The title compound was synthesized analogous to Example 2, using methyl 2-(5-(4-(3-(3-chlorophenyl)ureido)phenyl)oxazole-2-carboxamido)-3-methylbutanoate. ¹HNMR (DMSO-d₆, 300 MHz): δ 12.932 (s, 1H), 9.066 (s, 1H), 8.997 (s, 1H), 8.667-8.639 (d, 1H), 7.814 (s, 1H), 7.799-7.771 (d, J=8.4 Hz, 2H), 7.727-7.703 (m, 1H), 7.630-7.601 (d, J=9 Hz, 2H), 7.347-7.268 (m, 2H), 7.052-7.029 (m, 1H), 4.306-4.256 (dd, J=1.2, 6.9 Hz, 1H), 2.279-2.212 (m, 1H), 0.975-0.952 (d, J=6.9 Hz, 6H); MS (ESI) m/z 455 (M−H), 457 (M+H).

Example 61

(S)-methyl 2-(5-(4-(3-(2-chloro-4-(trifluoromethyl) phenyl)ureido) phenyl)oxazole-2-carboxamido)-3-methylbutanoate The title compound was synthesized analogous to Example 1, using 2-chloro-4-(trifluoromethyl)-1-isocyanatobenzene (0.533 mmol) and intermediate 1. ¹H NMR (DMSO-d₆, 300 MHz): δ 9.883 (s, 1H), 9.025-8.998 (d, 1H), 8.707 (s, 1H), 8.498-8.469 (d, J=8.7 Hz, 1H), 7.904-7.898 (d, J=1.8 Hz, 1H), 7.842 (s, 1H), 7.837-7.807 (d, J=9 Hz, 2H), 7.723-7.688 (dd, J=1.8, 9 Hz, 1H), 7.653-7.624 (d, J=8.7 Hz, 2H), 4.332-4.2827 (m, 1H), 3.682 (s, 3H), 2.228-2.219 (m, 1H), 0.982-0.960 (d, J=6.6 Hz, 6H); MS (ESI) m/z 537 (M−H), 539 (M+H).

Example 62

(S)-2-(5-(4-(3-(2-chloro-4-(trifluoromethyl)phenyl) ureido)phenyl)oxazole-2-carboxamido)-3-methylbutanoic acid The title compound was synthesized analogous to Example 2, using methyl 2-(5-(4-(3-(2-chloro-4-(trifluoromethyl)phenyl)ureido)phenyl)oxazole-2-carboxamido)-3-methylbutanoate. ¹H-NMR (DMSO-d₆, 300 MHz): δ 12.944 (s, 1H), 9.888 (s, 1H), 8.709 (s, 1H), 8.681-8.653 (d, 1H), 8.499-8.469 (d, J=9 Hz, 1H), 7.903-7.899 (d, J=1.2 Hz, 1H), 7.836 (s, 1H), 7.836-7.808 (d, J=8.4 Hz, 2H), 7.723-7.692 (d, J=9.3 Hz, 1H), 7.653-7.624 (d, J=8.1 Hz, 2H), 4.308-4.259 (m, 1H), 2.258-2.236 (m, 1H), 0.976-0.954 (d, J=6.6 Hz, 6H); MS (ESI) m/z 523 (M−H), 525 (M+H).

Example 63

(S)-methyl 2-(5-(4-(3-(4-chloro-2-fluorophenyl)ureido)phenyl)oxazole-2-carboxamido)-3-methylbutanoate The title compound was synthesized analogous to Example 1, using 4-chloro-2-fluoro-1-isocyanatobenzene (0.533 mmol) and intermediate 1. $^1$H-NMR (DMSO-$d_6$, 300 MHz): δ 9.356 (s, 1H), 9.017-8.990 (d, 1H), 8.733 (s, 1H), 8.208-8.149 (m, 1H), 7.826 (s, 1H), 7.809-7.780 (d, J=8.7 Hz, 2H), 7.623-7.593 (d, J=9 Hz, 2H), 7.514-7.470 (d, J=2.1, 11.1 Hz, 1H), 7.270-7.241 (dd, J=0.6, 8.7 Hz, 1H), 4.328-4.277 (m, 1H), 3.680 (s, 3H), 2.286-2.217 (m, 1H), 0.979-0.957 (d, J=6.6 Hz, 6H); MS (ESI) m/z 487 (M−H), 489 (M+H).

Example 64

(S)-2-(5-(4-(3-(4-chloro-2-fluorophenyl)ureido)phenyl)oxazole-2-carboxamido)-3-methylbutanoic acid The title compound was synthesized analogous to Example 2, using methyl 2-(5-(4-(3-(4-chloro-2-fluorophenyl)ureido)phenyl)oxazole-2-carboxamido)-3-methylbutanoate. $^1$HNMR (DMSO-$d_6$, 300 MHz): δ 12.939 (s, 1H), 9.413 (s, 1H), 8.763 (s, 1H), 8.671-8.643 (d, J=8.4 Hz, 1H), 8.208-8.149 (t, J=8.7, 9 Hz, 1H), 7.819 (s, 1H), 7.809-7.780 (d, J=8.7 Hz, 2H), 7.624-7.595 (d, J=8.7 Hz, 2H), 7.513-7.468 (dd, J=3, 11.5 Hz, 1H), 7.267-7.237 (d, J=9 Hz, 1H), 4.306-4.257 (m, 1H), 2.278-2.211 (m, 1H), 0.974-0.952 (d, J=6.6 Hz, 6H); MS (ESI) m/z 473 (M−H), 475 (M+H)$^+$.

Example 65

(S)-Methyl 2-(5-(4-(3-(2,3-dihydro-1H-inden-5-yl)ureido)phenyl)thiazole-2-carboxamido)-3-methylbutanoate The title compound was synthesized analogous to Example 9, using 5-isocyanato-2,3-dihydro-1H-indene (0.599 mmol) and intermediate 2. $^1$HNMR (DMSO-$d_6$, 300 MHz): δ ppm 8.891 (s, 1H), 8.732-8.704 (d, 1H), 8.602 (s, 1H), 8.347 (s, 1H), 7.717-7.689 (d, J=8.4 Hz, 2H), 7.575-7.547 (d, J=8.4 Hz, 2H), 7.289 (s, 1H), 7.172-7.101 (m, 2H), 4.349-4.299 (t, J=7.2, 7.8 Hz, 1H), 3.681 (s, 3H), 2.859-2.770 (m, 4H), 2.328-2.204 (m, 1H), 2.054-1.952 (m, 2H), 0.965-0.923 (d, J=6.3 Hz, 6H); MS (ESI) m/z 491 (M−H), 493 (M+H)$^+$.

Example 66

(S)-2-(5-(4-(3-(2,3-dihydro-1H-inden-5-yl)ureido)phenyl)thiazole-2-carboxamido)-3-methylbutanoic acid The title compound was synthesized analogous to Example 10, using (S)-methyl 2-(5-(4-(3-(2,3-dihydro-1H-inden-5-yl)ureido)phenyl)thiazole-2-carboxamido)-3-methylbutanoate. $^1$HNMR (DMSO-$d_6$, 300 MHz): δ 12.940 (s, 1H), 8.897 (s, 1H), 8.608 (s, 1H), 8.362-8.339 (d, 2H), 7.718-7.689 (d, J=8.7 Hz, 2H), 7.577-7.549 (d, J=8.4 Hz, 2H), 7.390 (s, 1H), 7.132 (m, 2H), 4.334-4.306 (m, 1H), 2.860-2.771 (m, 4H), 2.312-2.254 (m, 1H), 2.027-1.979 (m, 2H), 0.967-0.946 (d, J=6.3 Hz, 6H); MS (ESI) m/z 477 (M−H), 479 (M+H).

Example 67

(S)-methyl 2-(5-(4-(3-(4-chlorophenyl)ureido)phenyl)thiazole-2-carboxamido)-3-methylbutanoate The title compound was synthesized analogous to Example 9, using 1-chloro-4-isocyanatobenzene and intermediate 2. $^1$HNMR (DMSO-$d_6$, 300 MHz): δ 8.991 (s, 1H), 8.897 (s, 1H), 8.737-8.710 (d, 1H), 8.353 (s, 1H), 7.730-7.701 (d, J=8.7 Hz, 2H), 7.583-7.554 (d, J=8.7 Hz, 2H), 7.513-7.484 (d, J=8.7 Hz, 2H), 7.355-7.325 (d, J=9 Hz, 2H), 4.324-4.287 (t, J=7.2, 7.8 Hz, 1H), 3.681 (s, 3H), 2.342-2.242 (m, 1H), 0.965-0.923 (d, J=6.3 Hz, 6H); MS (ESI) m/z 487 (M+H)$^+$.

Example 68

(S)-2-(5-(4-(3-(4-chlorophenyl)ureido)phenyl)thiazole-2-carboxamido)-3-methylbutanoic acid The title compound was synthesized analogous to Example 10, using (S)-methyl 2-(5-(4-(3-(4-chlorophenyl)ureido)phenyl)thiazole-2-carboxamido)-3-methylbutanoate. $^1$HNMR (DMSO-$d_6$, 300 MHz): δ 12.940 (s, 1H), 9.021 (s, 1H), 8.928 (s, 1H), 8.367-8.346 (d, 1H), 7.730-7.702 (d, J=8.4 Hz, 2H), 7.585-7.556 (d, J=8.7 Hz, 2H), 7.514-7.485 (d, J=8.7 Hz, 2H), 7.355-7.325 (d, J=9 Hz, 2H), 4.334-4.286 (dd, J=2.4, 6 Hz, 1H), 2.274-2.252 (m, 1H), 0.964-0.945 (d, J=5.7 Hz, 6H); MS (ESI) m/z 471 (M−H), 473 (M+H).

Example 69

(S)-Methyl 2-(5-(4-(3-(3-chlorophenyl)ureido)phenyl)thiazole-2-carboxamido)-3-methylbutanoate The title compound was synthesized analogous to Example 9, using 1-chloro-3-isocyanatobenzene and intermediate 2. $^1$HNMR (DMSO-$d_6$, 300 MHz): δ 9.337 (s, 1H), 8.741-8.713 (d, 2H), 8.362 (s, 1H), 8.203-8.144 (t, J=8.7, 9 Hz, 1H), 7.744-7.716 (d, J=8.4 Hz, 2H), 7.581-7.552 (d, J=8.7 Hz, 2H), 7.507-7.463 (d, J=2.7, 11.1 Hz, 1H), 7.266-7.237 (d, J=3.7 Hz, 2H), 4.350-4.299 (t, J=7.5, 7.8 Hz, 1H), 3.681 (s, 3H), 2.306-2.238 (m, 1H), 0.965-0.923 (d, J=6.3 Hz, 6H); MS (ESI) m/z 485 (M−H), 487 (M+H)$^+$.

Example 70

(S)-2-(5-(4-(3-(3-chlorophenyl)ureido)phenyl)thiazole-2-carboxamido)-3-methylbutanoic acid The title compound was synthesized analogous to Example 10, using (S)-methyl 2-(5-(4-(3-(3-chlorophenyl)ureido)phenyl)thiazole-2-carboxamido)-3-methylbutanoate. $^1$HNMR (DMSO-$d_6$, 300 MHz): δ 12.959 (s, 1H), 9.354 (s, 1H), 8.722-8.715 (d, 1H), 8.369-8.341 (m, 3H), 8.203-8.144 (d, J=8.7, 9 Hz, 1H), 7.745-7.716 (d, J=8.7 Hz, 2H), 7.582-7.553 (d, J=8.7 Hz, 2H), 7.506-7.462 (dd, J=2.1, 11.1 Hz, 1H), 7.266-7.237 (d, J=8.7 Hz, 1H), 4.333-4.285 (dd, J=2.4, 6 Hz, 1H), 2.217-2.208 (m, 1H), 0.967-0.945 (d, J=6.6 Hz, 6H); MS (ESI) m/z 471 (M−H), 473 (M+H)$^+$.

Example 71

(S)-methyl 2-(5-(4-(3-(2-chloro-4-(trifluoromethyl)phenyl)ureido) phenyl)thiazole-2-carboxamido)-3-methylbutanoate The title compound was synthesized analogous to Example 9, using 2-chloro-4-(trifluoromethyl)-1-isocyanatobenzene and intermediate 2. ¹HNMR (DMSO-d$_6$, 300 MHz): δ 9.860 (s, 1H), 8.747-8.720 (d, 2H), 8.687 (s, 1H), 8.495-8.465 (d, J=9 Hz, 1H), 8.376 (s, 1H), 7.892 (s, 1H), 7.769-7.741 (d, J=8.4 Hz, 2H), 7.718-7.688 (d, J=9 Hz, 1H), 7.611-7.582 (d, J=8.7 Hz, 2H), 4.351-4.301 (t, J=7.5 Hz, 1H), 3.682 (s, 3H), 2.285-2.262 (m, 1H), 0.967-0.924 (t, J=6.6 Hz, 6H); MS (ESI) m/z 555 (M+H).

Example 72

(S)-2-(5-(4-(3-(2-chloro-4-(trifluoromethyl)phenyl) ureido)phenyl)thiazole-2-carboxamido)-3-methylbutanoic acid The title compound was synthesized analogous to Example 10, using (S)-methyl 2-(5-(4-(3-(2-chloro-4-(trifluoromethyl)phenyl)ureido)phenyl)thiazole-2-carboxamido)-3-methylbutanoate. ¹HNMR (DMSO-d$_6$, 300 MHz): δ 13.022 (s, 1H), 9.871 (s, 1H), 8.695 (s, 1H), 8.495-8.466 (d, J=8.7 Hz, 1H), 8.370-8.351 (d, J=5.7 Hz, 2H), 7.895 (s, 1H), 7.772-7.743 (d, J=8.7 Hz, 2H), 7.721-7.687 (d, J=10.2 Hz, 1H), 7.613-7.584 (d, J=8.7 Hz, 2H), 4.332-4.284 (dd, J=2.1, 6 Hz, 1H), 2.319-2.209 (m, 1H), 0.964-0.942 (t, J=6.6 Hz, 6H); MS (ESI) m/z 539 (M−H), 541 (M+H)⁺.

Example 73

(S)-methyl 2-(5-(4-(3-(4-chloro-2-fluorophenyl)ureido)phenyl)thiazole-2-carboxamido)-3-methylbutanoate The title compound was synthesized analogous to Example 9, using 2-chloro-4-(trifluoromethyl)-1-isocyanatobenzene and intermediate 2. ¹HNMR (DMSO-d$_6$, 300 MHz): δ 9.037 (s, 1H), 8.966 (s, 1H), 8.741-8.713 (d, J=8.4 Hz, 1H), 8.359 (s, 1H), 7.736-7.708 (m 3H), 7.590-7.561 (d, J=8.7 Hz, 2H), 7.317-7.294 (m, 1H), 7.056-7.034 (m, 1H), 4.350-4.300 (t, J=7.5, 7.8 Hz, 1H), 3.681 (s, 3H), 2.284-2.261 (m, 1H), 0.966-0.923 (t, J=6.3, 6.6 Hz, 6H); MS (ESI) m/z 504 (M−H), 505 (M+H).

Example 74

(S)-2-(5-(4-(3-(4-chloro-2-fluorophenyl)ureido)phenyl)thiazole-2-carboxamido)-3-methylbutanoic acid The title compound was synthesized analogous to Example 10, using (S)-methyl 2-(5-(4-(3-(4-chloro-2-fluorophenyl) ureido)phenyl)thiazole-2-carboxamido)-3-methylbutanoate. ¹HNMR (DMSO-d$_6$, 300 MHz): δ 13.002 (s, 1H), 9.045 (s, 1H), 8.976 (s, 1H), 8.369-8.342 (m, 2H), 7.738 (m, 3H), 7.591-7.563 (d, J=8.4 Hz, 2H), 7.347-7.296 (m, 1H), 7.050-7.028 (m, 1H), 4.335-4.287 (t, J=2.1, 6 Hz, 1H), 2.320-2.231 (m, 1H), 0.966-0.946 (d, J=6 Hz, 6H); MS (ESI) m/z 489 (M−H), 491 (M+H)⁺.

Example 75

(S)-Methyl 2-(4-(4-(3-(4-chlorophenyl)ureido)phenyl)thiazole-2-carboxamido)-3-methylbutanoate The title compound was synthesized analogous to Example 23, using 4-chlorophenyl isocyanate and intermediate 3. ¹HNMR (DMSO-d$_6$, 300 MHz): δ 8.912 (s, 1H), 8.870 (s, 1H), 8.820-8.792 (d, J=8.4 Hz, 1H), 8.318 (s, 1H), 8.052-8.024 (d, J=8.4 Hz, 2H), 7.590-7.561 (d, J=8.7 Hz, 2H), 7.521-7.492 (d, J=8.7 Hz, 2H), 7.356-7.326 (d, J=9 Hz, 2H), 4.395-4.343 (t, J=7.8 Hz, 1H), 3.700 (s, 3H), 2.319-2.273 (m, 1H), 1.000-0.953 (t, J=6.9, 7.2 Hz, 6H); MS (ESI) m/z 485 (M−H), 487 (M+H)⁺.

Example 76

(S)-2-(4-(4-(3-(4-Chlorophenyl)ureido)phenyl)thiazole-2-carboxamido)-3-methylbutanoic acid The title compound was synthesized analogous to Example 24, using (S)-methyl 2-(4-(4-(3-(4-chlorophenyl)ureido)phenyl)thiazole-2-carboxamido)-3-methylbutanoate. ¹HNMR (DMSO-d$_6$, 300 MHz): δ 12.990 (s, 1H), 9.039 (s, 1H), 9.008 (s, 1H), 8.512-8.483 (d, J=8.7 Hz, 1H), 8.313 (s, 1H), 8.031-8.002 (d, J=8.7 Hz, 2H), 7.588-7.559 (d, J=8.7 Hz, 2H), 7.519-7.489 (d, J=9 Hz, 2H), 7.351-7.321 (d, J=9 Hz, 2H), 4.373-4.323 (dd, J=2.4, 6.3 Hz, 1H), 2.325-2.258 (m, 1H), 0.994-0.971 (d, J=6.9, 7.2 Hz, 6H); MS (ESI) 471 (M−H), 473 (M+H)⁺.

Example 77

(S)-Methyl 2-(4-(4-(3-(2,3-dihydro-1H-inden-5-yl) ureido)phenyl)thiazole-2-carboxamido)-3-methylbutanoate The title compound was synthesized analogous to Example 23, using 2,3-dihydro-5-isocyanato-1H-indene and intermediate 3. ¹HNMR (DMSO-d$_6$, 300 MHz): δ 8.817-8.795 (d, 2H), 8.578 (s, 1H), 8.306 (s, 1H), 8.040-8.011 (d, J=8.7 Hz, 2H), 7.582-7.553 (d, J=8.7 Hz, 2H), 7.401 (s, 1H), 7.170-7.104 (m, 2H), 4.394-4.342 (t, J=7.5, 8.1 Hz, 1H), 3.700 (s, 3H), 2.863-2.773 (m, 4H), 2.343-2.274 (m, 1H), 2.087-1.981 (m, 2H), 1.001-0.953 (t, J=7.2 Hz, 6H); MS (ESI) m/z 491 (M−H), 493 (M+H)⁺.

Example 78

(S)-2-(4-(4-(3-(2,3-dihydro-1H-inden-5-yl)ureido) phenyl)thiazole-2-carboxamido)-3-methylbutanoic acid The title compound was synthesized analogous to Example 24, using (S)-methyl 2-(4-(4-(3-(2,3-dihydro-1H-inden-5-yl) ureido)phenyl)thiazole-2-carboxamido)-3-methylbutanoate. ¹HNMR (DMSO-d$_6$, 300 MHz): δ 13.029 (s, 1H), 8.834 (s, 1H), 8.592 (s, 1H), 8.508-480 (d, J=8.4 Hz, 1H), 8.304 (s, 1H), 8.021-7.992 (d, J=8.7 Hz, 2H), 7.581-7.552 (d, J=8.7 Hz, 2H), 7.397 (s, 1H), 7.142-7.102 (m, 2H), 4.374-4.324 (dd, J=2.1, 6.3 Hz, 1H), 2.862-2.771 (m, 4H), 2.326-2.259 (m, 1H), 2.053-1.979 (m, 2H), 0.995-0.973 (t, J=6.6 Hz, 6H); MS (ESI) m/z 477 (M−H), 479 (M+H)⁺.

Example 79

(S)-methyl 2-(4-(4-(3-(3-chlorophenyl)ureido)phenyl)thiazole-2-carboxamido)-3-methylbutanoate The title compound was synthesized analogous to Example 23, using 3-chlorophenyl isocyanate and intermediate 3. ¹HNMR (DMSO-d$_6$, 300 MHz): δ 8.959 (s, 1H), 8.940 (s, 1H), 8.826-8.798 (d, J=8.4 Hz, 1H), 8.325 (s, 1H), 8.058-8.030 (d, J=8.4 Hz, 2H), 7.734 (s, 1H), 7.596-7.567 (d, J=8.7 Hz, 2H), 7.318-7.294 (m, 2H), 7.046-7.023 (m, 1H), 4.395-4.343 (t, J=7.8 Hz, 1H), 3.700 (s, 3H), 2.320-2.274 (m, 1H), 1.001-0.953 (t, J=6.9, 7.5 Hz, 6H); MS (ESI) m/z 485 (M−H), 487 (M+H)⁺.

Example 80

(S)-2-(4-(4-(3-(3-chlorophenyl)ureido)phenyl)thiazole-2-carboxamido)-3-methylbutanoic acid The title compound was synthesized analogous to Example 24, using (S)-methyl 2-(4-(4-(3-(3-chlorophenyl)ureido)phenyl)thiazole-2-carboxamido)-3-methylbutanoate. $^1$HNMR (DMSO-$d_6$, 300 MHz): δ 11.177 (s, 2H), 8.303 (s, 2H), 7.990-7.963 (d, J=8.7 Hz, 2H), 7.186 (s, 1H), 7.747-7.719 (d, J=8.4 Hz, 2H), 7.443-7.416 (d, J=8.1 Hz, 1H), 7.310-7.256 (t, J=8.1 Hz, 1H), 6.987-7.691 (d, J=7.8 Hz, 1H), 4.309-4.264 (dd, J=3.3, 5.1 Hz, 1H), 2.305-2.242 (m, 1H), 0.999-0.979 (d, J=6 Hz, 6H); MS (ESI) m/z 471 (M–H), 473 (M+H)$^+$.

Example 81

(S)-Methyl 2-(4-(4-(3-(2-chloro-4-(trifluoromethyl)phenyl)ureido) phenyl)thiazole-2-carboxamido)-3-methylbutanoate The title compound was synthesized analogous to Example 23, using 2-chloro-4-(trifluoromethyl)-1-isocyanatobenzene and intermediate 3. $^1$HNMR (DMSO-$d_6$, 300 MHz): δ 9.801 (s, 1H), 8.832-8.804 (d, J=8.4 Hz, 1H), 8.680 (s, 1H), 8.515-8.486 (d, J=8.7 Hz, 1H), 8.348 (s, 1H), 8.095-8.067 (d, J=8.4 Hz, 2H), 7.897-7.893 (d, J=1.2 Hz, 2H), 7.721-7.686 (dd, J=1.8, 9 Hz, 1H), 7.621-7.593 (d, J=8.4 Hz, 2H), 4.401-4.344 (t, J=8.1, 9 Hz, 1H), 3.702 (s, 3H), 2.351-2.280 (m, 1H), 1.003-0.955 (t, J=7.2 Hz, 6H); MS (ESI) m/z 553 (M–H), 555 (M+H)$^+$.

Example 82

(S)-2-(4-(4-(3-(2-chloro-4-(trifluoromethyl)phenyl)ureido)phenyl)thiazole-2-carboxamido)-3-methylbutanoic acid The title compound was synthesized analogous to Example 24, using (S)-methyl 2-(4-(4-(3-(2-chloro-4-(trifluoromethyl)phenyl)ureido)phenyl)thiazole-2-carboxamido)-3-methylbutanoate. $^1$HNMR (DMSO-$d_6$, 300 MHz): δ 13.049 (s, 1H), 9.916 (s, 1H), 8.729 (s, 1H), 8.582-8.480 (dd, J=2.7, 8.7 Hz, 2H), 8.344 (s, 1H), 8.074-8.045 (d, J=8.7 Hz, 2H), 7.890-7.885 (d, J=1.5 Hz, 1H), 7.715-7.681 (dd, J=1.5, 9 Hz, 1H), 7.626-7.597 (d, J=8.7 Hz, 2H), 4.378-4.329 (dd, J=2.1, 6.3 Hz, 1H), 2.326-2.260 (m, 1H), 0.996-0.973 (t, J=6.9 Hz, 6H); MS (ESI) m/z 539 (M–H), 541 (M+H)$^+$.

Example 83

(S)-Methyl 2-(4-(4-(3-(4-chloro-2-fluorophenyl)ureido)phenyl)thiazole-2-carboxamido)-3-methylbutanoate The title compound was synthesized analogous to Example 23, using 4-chloro-2-fluoro-1-isocyanatobenzene and intermediate 3. $^1$HNMR (DMSO-$d_6$, 300 MHz): δ 9.281 (s, 1H), 8.824-8.796 (d, J=8.4 Hz, 1H), 8.703 (s, 1H), 8.330 (s, 1H), 8.227-8.168 (t, J=8.7, 9 Hz, 1H), 8.069-8.040 (d, J=8.7 Hz, 2H), 7.589-7.560 (s, J=8.7 Hz, 2H), 7.508-7.463 (d, J=2.1, 11.1 Hz, 1H), 7.268-7.238 (d, J=9 Hz, 1H), 4.395-4.343 (t, J=7.8 Hz, 1H), 3.700 (s, 3H), 2.341-2.273 (m, 1H), 1.000-0.953 (t, J=6.9, 7.2 Hz, 6H); MS (ESI) m/z 503 (M–H), 505 (M+H)$^+$.

Example 84

(S)-2-(4-(4-(3-(4-chloro-2-fluorophenyl)ureido)phenyl)thiazole-2-carboxamido)-3-methylbutanoic acid The title compound was synthesized analogous to Example 24, using (S)-methyl 2-(4-(4-(3-(4-chloro-2-fluorophenyl)ureido)phenyl)thiazole-2-carboxamido)-3-methylbutanoate. $^1$HNMR (DMSO-$d_6$, 300 MHz): δ 13.009 (s, 1H), 9.351 (s, 1H), 8.733 (s, 1H), 8.511-8.482 (d, J=8.7 Hz, 1H), 8.325 (s, 1H), 8.222-8.163 (t, J=8.7, 9 Hz, 1H), 8.048-8.019 (d, J=8.7 Hz, 2H), 7.589-7.560 (d, J=8.7 Hz, 2H), 7.501-7.457 (dd, J=2.1, 11.1 Hz, 1H), 7.263-7.233 (d, J=9 Hz, 1H), 4.374-4.325 (dd, J=2.1, 6.3 Hz, 1H), 2.324-2.258 (m, 1H), 0.994-0.971 (t, J=6.9 Hz, 6H); MS (ESI) m/z 489 (M–H), 491 (M+H)$^+$.

Example 85

Methyl 2-(5-(4-(4-(2-cyanopropan-2-yl)benzamido)phenyl)thiazole-2-carboxamido)-3-methylbutanoate Trimethyl aluminium (0.36 ml, 2M solution in toluene) was added to a solution of methyl 4-(2-cyanopropan-2-yl)benzoate (Intermediate 5, 100 mg) and methyl 2-(5-(4-aminophenyl) thiazole-2-carboxamido)-3-methylbutanoate (Intermediate 2, 150 mg) in toluene (12 ml). The reaction mixture was heated to 80° C. for 4 hours in a sealed tube. Reaction mass was cooled to RT, water was added and neutralized with saturated aqueous solution of ammonium chloride. Methylene chloride was added to it. Organic and aqueous layers were separated. Organic layer was washed successively with 1N HCl, saturated NaHCO$_3$ and brine solution. It was then dried over sodium sulfate and concentrated to obtain dark brown residue which was purified by silica gel column chromatography in EtOAc-Petroleum ether to obtain pale brown solid. The solid was crystallized in CHCl$_3$-petroleum ether to obtain title compound as off white solid. Yield: 75 mg (33%); $^1$HNMR (DMSO-$d_6$, 300 MHz): δ 10.49 (s, 1H), 8.75 (d, 1H), 8.41 (s, 1H), 8.04 (d, 2H), 7.93 (d, 2H), 7.81 (d, 2H), 7.71 (d, 2H), 4.33 (m, 1H), 3.68 (s, 3H), 2.27 (m, 1H), 1.74 (s, 6H), 0.95 (m, 6H); MS (ES+) m/z 505.2 (M+1).

Example 86

2-(5-(4-(4-(2-cyanopropan-2-yl)benzamido)phenyl)thiazole-2-carboxamido)-3-methylbutanoic acid To methyl 2-(5-(4-(4-(2-cyanopropan-2-yl)benzamido)phenyl)thiazole-2-carboxamido)-3-methylbutanoate (Example 85, 65 mg) in THF (1 ml), methanol (1 ml) and 1M lithium hydroxide monohydrate (0.51 ml) was added and reaction mixture was stirred overnight at RT. Organic solvent was concentrated and added water, dilute HCl was added under stirring to pH acidic. The reaction mixture was filtered, to obtain the title compound. Yield: 22 mg (35%). $^1$HNMR (DMSO-$d_6$, 300 MHz): δ 13.0 (bs, 1H), 10.49 (s, 1H), 8.4 (s, 1H), 8.37 (d, 1H), 8.04 (d, 2H), 7.93 (d, 2H), 7.81 (d, 2H), 7.71 (d, 2H), 4.31 (m, 1H), 2.25 (m, 1H), 1.74 (s, 6H), 0.97 (m, 6H); MS (ES+) m/z 491.2 (M+1).

Example 87

Methyl 2-(5-(4-(4-(3-cyanopentan-3-yl)benzamido)phenyl)thiazole-2-carboxamido)-3-methylbutanoate The title compound was synthesized analogous to Example 85, using methyl 4-(3-cyanopentan-3-yl)benzoate (Intermediate 6) and intermediate 2. ¹HNMR (DMSO-d₆, 300 MHz) δ 10.52 (s, 1H), 8.78 (d, 1H), 8.41 (s, 1H), 8.03 (d, 2H), 7.93 (d, 2H), 7.81 (d, 2H), 7.62 (d, 2H), 4.33 (m, 1H), 3.68 (s, 3H), 2.26 (m, 1H), 2.1-2.02 (m, 4H), 0.95 (t, 6H), 0.81 (t, 6H); MS (ES+): m/z 533.2 (M+1).

Example 88

2-(5-(4-(4-(3-cyanopentan-3-yl)benzamido)phenyl) thiazole-2-carboxamido)-3-methylbutanoic acid The title compound was synthesized analogous to Example 86, using methyl 2-(5-(4-(4-(3-cyanopentan-3-yl)benzamido)phenyl)thiazole-2-carboxamido)-3-methylbutanoate. ¹HNMR (DMSO-d₆, 300 MHz): δ 13.03 (bs, 1H), 10.52 (s, 1H), 8.4 (s, 1H), 8.37 (d, 1H), 8.03 (d, 2H), 7.93 (d, 2H), 7.81 (d, 2H), 7.62 (d, 2H), 4.29 (m, 1H), 2.25 (m, 1H), 2.12-1.99 (m, 4H), 0.96 (d, 6H), 0.81 (t, 6H); MS (ES+) m/z 519.2 (M+1).

Example 89

Methyl 2-(5-(4-(benzylamino)phenyl)thiazole-2-carboxamido)-3-methylbutanoate

To a solution of methyl 2-(5-(4-aminophenyl)thiazole-2-carboxamido)-3-methylbutanoate (Intermediate 2, 200 mg) in DCM (6 ml) was added triethyl amine (0.417 ml, 5.0 equiv.) and benzyl bromide (308 mg, 3.0 eq) and the reaction mixture was stirred for 2 days at RT. The solvent was evaporated and the residue was purified by column chromatography using 1% ethylacetate in chloroform to give the title compound. Yield: 50 mg (20%). ¹H NMR (CDCl₃; 300 MHz): δ 7.87 (s, 1H), 7.66 (d, 1H), 7.44 (d, 2H), 7.38 (m, 5H), 7.32 (m, 1H), 6.68 (d, 2H), 4.74 (m, 1H), 4.40 (s, 2H), 3.79 (s, 3H), 2.34 (m, 1H), 1.05 (t, 6H); MS (ESI) m/z 424.2 [M+H]⁺, 446.1 [M+Na]⁺.

Example 90

Methyl 2-(5-(4-((4-fluorobenzyl)amino)phenyl)thiazole-2-carboxamido)-3-methylbutanoate To a solution of the methyl 2-(5-(4-aminophenyl)thiazole-2-carboxamido)-3-methylbutanoate (Intermediate 2, 250 mg) in acetone (8 ml) was added potassium carbonate (155 mg, 1.5 eq) and 1-(bromomethyl)-4-fluorobenzene (0.112 ml, 1.2 eq). The reaction mixture was stirred for 8 hours at 60-65° C. Water was added after the completion of the reaction, and the reaction mixture was extracted with ethyl acetate. Organic layer was washed with water and concentrated. The compound was purified by column chromatography using 10-15% ethylacetate in petroleum ether to give the title compound. Yield: 130 mg (39%). ¹H NMR (CDCl₃; 300 MHz): δ 7.87 (s, 1H), 7.66 (d, 1H), 7.44 (d, 2H), 7.37 (m, 2H), 7.08 (t, 2H), 6.68 (d, 2H), 4.74 (m, 1H), 4.37 (s, 2H), 3.79 (s, 3H), 2.37 (m, 1H), 1.05 (t, 6H); MS (ESI) m/z 442.1 [M+H]⁺, 464.1 [M+Na]⁺.

Example 91

2-(5-(4-((4-Fluorobenzyl)amino)phenyl)thiazole-2-carboxamido)-3-methylbutanoic acid The title compound was synthesized analogous to Example 86, using methyl 2-(5-(4-((4-fluorobenzyl)amino)phenyl) thiazole-2-carboxamido)-3-methylbutanoate. ¹HNMR (CDCl₃; 300 MHz): δ 7.89 (s, 1H), 7.68 (d, 1H), 7.44 (d, 2H), 7.37 (m, 2H), 7.08 (t, 2H), 6.68 (d, 2H), 4.77 (m, 1H), 4.37 (s, 2H), 2.42 (m, 1H), 1.01 (t, 6H); MS (ESI) m/z 428.1 [M+H]⁺, 450.1 [M+Na]⁺.

Example 92

Methyl 2-(5-(4-(dibenzylamino)phenyl)thiazole-2-carboxamido)-3-methylbutanoate

The title compound was synthesized analogous to Example 89, except that base used was potassium carbonate instead of triethylamine and solvent used was acetone instead of DCM and benzyl bromide used was 1.2 equivalent. ¹H NMR (DMSO-d₆; 300 MHz): δ 8.60 (b, 1H), 8.16 (d, 1H), 7.50 (d, 2H), 7.37 (m, 4H), 7.28 (m, 6H), 6.75 (d, 2H), 4.78 (s, 4H), 4.33 (t, 1H), 3.66 (s, 3H), 2.31 (m, 1H), 0.94 (m, 6H); MS (ESI) m/z 514.2 [M+H]⁺, 536.2 [M+Na]⁺.

Example 93

2-(5-(4-(dibenzylamino)phenyl)thiazole-2-carboxamido)-3-methylbutanoic acid

The title compound was synthesized analogous to Example 86, using methyl 2-(5-(4-(dibenzylamino)phenyl)thiazole-2-carboxamido)-3-methylbutanoate. ¹H NMR (DMSO-d₆; MHz): δ 13.00 (bs, 1H), 8.23 (m, 2H), 7.15 (d, 2H), 7.37 (d, 4H), 7.28 (m, 6H), 6.75 (d, 2H), 4.79 (s, 4H), 4.29 (m, 1H), 2.25 (m, 1H), 0.94 (m, 6H); MS (ESI) m/z 500.2 [M+H]⁺.

Example 94

Methyl 2-(5-(4-(5-butylpicolinamido)phenyl)thiazole-2-carboxamido)-3-methylbutanoate A solution of 5-butylpicolinic acid (1 mL) in thionyl chloride (24 eq.) was heated at 60-70° C. for 1 hour to form 5-butylpicolinoyl chloride. Excess of thionyl chloride was removed. Methyl 2-(5-(4-aminophenyl)thiazole-2-carboxamido)-3-methylbutanoate (Intermediate 2, 200 mg) in DCM (5 mL) and pyridine (5 mL) was added to 5-butylpicolinoyl chloride and the reaction mixture was stirred for 1 hour at RT. Solvent was removed and ether was added to it. The solution was stirred, filtered, washed with water and dried obtain the title compound. ¹H NMR (DMSO-d₆; 300 MHz): δ 10.81 (s, 1H), 8.57 (d, 1H), 8.60 (s, 1H), 8.41 (s, 1H), 8.12 (m, 3H), 7.92 (d, 1H), 7.81 (d, 2H), 4.35 (t, 1H), 3.68 (s, 3H), 2.75 (t, 2H), 2.28 (m, 1H), 1.64 (m, 2H), 1.37 (m, 2H), 0.97 (m, 9H); MS (ESI) m/z 495.2 [M+H]⁺.

Example 95

2-(5-(4-(5-butylpicolinamido)phenyl)thiazole-2-carboxamido)-3-methylbutanoic acid The title compound was synthesized analogous to Example 86, using Methyl 2-(5-(4-(5-butylpicolinamido)phenyl)thiazole-2-carboxamido)-3-methylbutanoate. ¹H NMR (DMSO-d₆; 300 MHz): δ 12.96 (bs, 1H), 10.81 (s, 1H), 8.59 (s, 1H), 8.40 (d, 2H), 8.07 (m, 3H), 7.92 (d, 1H), 7.80 (d, 2H), 4.30 (t, 1H), 2.73 (m, 2H), 2.27 (m, 1H), 1.61 (m, 2H), 1.33 (m, 2H), 0.94 (m, 9H); MS (ESI) m/z 481.2 [M+11]⁺.

Pharmacology Data

The efficacy of the compounds of the present invention can be determined by a number of pharmacological assays well known in the art, such as described below. The exemplified pharmacological assays, which follow herein below, have been carried out with the compounds of the present invention.

Materials:
Tissue culture materials, (Nunc)
Tissue culture media, (Invitrogen, US)
Fetal bovine serum (FBS), (Hyclone, US)
Bovine serum albumin (BSA), (Sigma, US)
sn-1,2-dioleoylglycerol (Sigma, US)
Sucrose (Sigma, US)
2-propanol (Qualigens, IN)
Heptane (Qualigens, IN)
$^{14}$C Oleoyl CoA (GE Healthcare)
Sf9 cells were obtained from American Type Culture Collection (ATCC)
Bradford Reagent (Sigma, US)
Cellfectin (Invitrogen, US)
Growth media: Graces's Insect media with 10% FBS (Hyclone, US)

Abbreviations:
FBS Fetal Bovine serum
ORF Open Reading Frame
DAB DGAT Assay Buffer
AESSM Alkaline Ethanol Stop Solution Mix
$KH_2PO_4$ Potassium Dihydrogen Phosphate
EDTA Ethylene Diamine Tetraacetic Acid
LB Luria Bertani
BSA Bovine serum albumin
PPO 2,5-Diphenyloxazole
POPOP 1,4-bis(5-phenyloxazol-2-yl)benzene
EDTA Ethylene Diamine Tetraacetic Acid Example 96

In-Vitro Protocol for DGAT-1 Assay

Sf9 Culture and Treatment

Sf9 cells were grown in T25 flasks containing Graces's Insect media (Invitrogen, US) with 10% FBS (Hyclone, US) with antibiotic (100 units/mL penicillin, 100 μg/mL streptomycin sulphate, 0.25 μg/mL amphotericin B as Fungizone) grown in a 27° C. incubator.

Viral Stock Preparation hDGAT-1ORF expression clone (RZPDo839C09146 in pDEST vector) was obtained from RZPD, Germany. hDGAT-1 bacmid DNA was obtained by transformation of the hDGAT expression clone into DH10Bac E. coli competent cells. Approximately 1 μg of hDGAT-1 bacmid DNA was infected into Sf9 cells with Cellfectin (Invitrogen, US) reagent. Following infection, Sf9 cells were incubated at 27° C. for 30 minutes. Five hours after infection, the media was replaced with growth media containing antibiotic (100 units/mL penicillin, 100 μg/mL streptomycin sulphate, 0.25 μg/mL amphotericin B as Fungizone) and incubated at 27° C. for 72 hours. The supernatant containing the virus was centrifuged at 1500 g for 5 minutes, passed through 0.22 μm filter, and subsequently stored at 4° C. The virus was further amplified three more times by re-infection of Sf9 cells and the viral titer was determined by plaque assay.

Preparation of DGAT-1 Microsomes from Sf9 Cells

Sf9 cells were seeded in spinner flasks on day 0 at a cell density of $1 \times 10^6$ and infected on day 1 with hDGAT-1 baculovirus at a multiplicity of infection (MOI) of 5 and a cell density of $2 \times 10^6$. On day 3 (or 66-72 hours), cells were harvested and centrifuged at 2500 g for 10 minutes. Pellet was resuspended in lysis buffer (100 mM sucrose, 50 mM KCl, 40 mM $KH_2PO_4$, 30 mM EDTA, pH 7.2) and passed through 21-gauge needle approximately 10 times. The mixture was centrifuged at 12,000 rpm in a Sigma 12158-H rotor at 4° C. for 30 minutes. The supernatant was subjected to centrifugation at 35,000 rpm in a Beckman Ti-45 rotor at 4° C. for 1 hour. The resultant pellet containing the microsomes were resuspended overnight in 1 mL of lysis buffer and total protein concentration was estimated using Bradford Reagent (Sigma, US). Microsomes were aliquoted and stored at −80° C.

Measurement of DGAT-1 Activity

Frozen aliquots of hDGAT-1 containing microsomes were thawed (5-10 mg/mL total protein) on ice and diluted to a working stock of 1 mg/mL with DGAT Assay Buffer (DAB). The DGAT reaction assay was performed by following the procedure described in U.S. Pat. No. 6,607,893 with some modifications that are described below.

Preparation of DGAT-1 substrate mixture: 1 mL stock solution of DGAT-1 substrate mixture contains 5.6 μL of $^{14}$C oleoyl CoA (16.8 nCi) and 105-μL 1,2-dioleoyl-sn-glycerol (1228.5 μM)

Preparation of stock solution: 1,2-dioleoyl-sn-glycerol stock (19.5 mM) was prepared by dissolving 25 mg of 1,2-dioleoyl-sn-glycerol (Sigma, US) in 2060 μL of acetone.

The assay was performed in duplicates in a reaction volume of 100 μL. The reaction volume consisted of:
(i) 27.5 μL of DGAT assay buffer (0.25M Sucrose, 1 mM EDTA (pH 8.0), 150 mM Tris-HCl, pH 7.4, 1.25 mg/mL fatty acid free BSA),
(ii) 10 μL of compound of present invention or standard (dissolved in DMSO and diluted to 10× with DAB and screened at 10 μM, 5 μM and 1 μM),
(iii) 60 μL DGAT-1 substrate mixture taken from a 1 mL stock (16.8 nCi of $^{14}$C oleoyl CoA and 1228.5 μM of 1,2-dioleyl-sn-glycerol),
(iv) 2.5 of 1 mg/mL of microsomes (the amount of assay buffer was varied depending upon the concentration of microsome to make up the volume to 100 μL).

Procedure:

The reaction was started by the addition of 2.5 of 1 mg/mL of microsomes (iv) to the mixture and incubated at 37° C. for 10 minutes. The reaction was stopped by the addition of 300 μL of Alkaline Ethanol Stop Solution Mix (AESSM; 12.5% of 100% non-denatured ethanol, 10% deionized water, 2.5% 1N NaOH, 75% stop solution (78.4% isopropanol, 19.6% n-heptane, 2% deionized water)) followed by addition of 600 μL of n-heptane. The mixture was vortexed and the triglycerides formed were extracted into the organic heptane phase. 250 μL of the heptane phase was added into 4 mL scintillation cocktail (66.72% toluene, 33.3% TritonX-100, 0.5% PPO, 0.02% POPOP) and counted on a liquid scintillation counter for 1 minute.

The % Inhibition of hDGAT-1 at 1 μM is displayed in the following table for representative examples of the present invention.

| Example No. | % inhibition of hDGAT-1 at 1 μM | Example No. | % inhibition of hDGAT-1 at 1 μM |
|---|---|---|---|
| 2 | ++ | 22 | ++ |
| 4 | ++ | 24 | + |
| 6 | ++ | 26 | + |
| 8 | ++ | 28 | + |
| 16 | ++ | 30 | + |
| 10 | ++ | 32 | + |
| 12 | ++ | 34 | + |
| 14 | ++ | 36 | + |

-continued

| Example No. | % inhibition of hDGAT-1 at 1 μM | Example No. | % inhibition of hDGAT-1 at 1 μM |
|---|---|---|---|
| 18 | ++ | 38 | + |
| 20 | ++ | 40 | ++ |
| 42 | ++ | 44 | ++ |
| 46 | + | 48 | ++ |
| 50 | ++ | 52 | ++ |
| 54 | ++ | 56 | ++ |
| 58 | ++ | 62 | ++ |
| 64 | ++ | 68 | ++ |
| 70 | ++ | 72 | ++ |
| 74 | ++ | 86 | ++ |
| 88 | ++ | 91 | + |
| 93 | + | 95 | ++ |

% Inhibition Ranges in μM
+ >0% Inhibition ≤50
++ >50% Inhibition ≤100

In-Vivo Protocol

Animals were housed and cared for in accordance with the Guidelines in force published by CPCSEA (Committee for the Purpose of Control and Supervision of Experiments on Animals), Tamil Nadu, India. Procedures using laboratory animals were approved by the IAEC (Institutional Animal Ethics Committee) of the Research Centre of Piramal Life Sciences Limited, Mumbai, India.

Example 97

Study Protocol for Screening of Compounds for Fat Tolerance Test (ftt) in Mice

Swiss mice of age 4-5 weeks and body weight between 25-30 g were selected for study. After overnight fasting, animals were divided into three groups based on plasma triglyceride level with same mean and variation Animals were administered with either vehicle (1% Tween 80 in 0.5% carboxy methylcellulose) or with compounds of the present invention (3 mg/kg, p.o.). Compounds of the present invention were prepared as suspension in 0.5% carboxy methylcellulose (CMC) with 1% Tween 80. 30 minutes after the treatment, olive oil load (10 ml/kg, p.o.) was given. Blood samples were collected at 1, 2, 3 and 4 h after the fat (olive oil) load. Plasma was separated and triglyceride level was measured using commercially available kits (Diasys, Germany). Percentage reduction in area under curve ($AUC_{0-4h}$) of the test compound was calculated by taking $AUC_{0-4h}$ of the vehicle group as 100%.

| Example No. | % Reduction (Plasma triglyceride) |
|---|---|
| 4 | + |
| 10 | ++ |
| 12 | ++ |
| 14 | ++ |
| 16 | ++ |
| 18 | ++ |
| 20 | ++ |
| 22 | ++ |

% Reduction (Plasma triglyceride) Scoring Details
+ >0% Reduction ≤50
++ >50% Reduction ≤100

REFERENCES FOR IN-VIVO PROTOCOL

1. Koji Ueshima, Hitomi Akihisa-Umeno, Akira Nagayoshi, Shoji Takakura, Masahiko Matsuo, Seitaro Mutoh. A gastrointestinal lipase inhibitor reduces progression of atherosclerosis in mice fed a western-type diet. *European Journal of Pharmacology*, 501, 137-142 (2004).
2. L-K Han et al. "Anti-obesity effects in rodents of dietary teasaponin, a lipase inhibitor" *International Journal of Obesity*, 25, 1459-1464 (2001).
3. Katherine J. D. Ashbourne Excoffon et al. "Correction of Hypertriglyceridemia and Impaired Fat Tolerance in Lipoprotein Lipase-Deficient Mice by Adenovirus-Mediated Expression of Human Lipoprotein Lipase" *Arteriosclerosis, Thrombosis, and Vascular Biology*, 17, 2532-2539, (1997).

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

The invention claimed is:
1. A compound of formula (I)

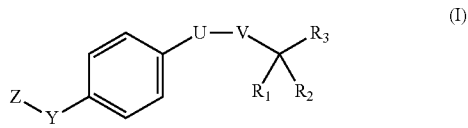

wherein,
Z is selected from unsubstituted or substituted alkylcycloalkyl, unsubstituted or substituted cycloalkyl, unsubstituted or substituted aryl, unsubstituted or substituted heteroaryl and unsubstituted or substituted heterocycle, wherein each of substituted alkylcycloalkyl, cycloalkyl, aryl, heteroaryl and heterocycle is substituted with one or more substituents selected from $R^a$;

$R^a$ at each occurrence is selected from halogen, oxo, thio, nitro, —CN, —$OR_x$, —$S(=O)_mR_x$, —$S(=O)_nNR_1R_2$, —$OCOR_x$, —$SCOR_x$, —$NR_xR_y$, —$NR_xCOR_y$, —$NR_x$-$COOR_y$, —$NR_xSOR_y$, —$NR_xSO_2R_y$, —$NR_xCONR_xR_y$, —$COR_x$, —$COOR_x$, —$CONR_xR_y$, —$(CR_xR_y)_n$—$OR_x$, alkyl, haloalkyl, alkenyl, alkynyl, cycloalkyl, alkylcycloalkyl, aryl, alkylaryl, heterocyclyl, alkylheterocyclyl, heteroaryl and alkylheteroaryl; wherein $R_x$ and $R_y$ are independently selected from H, alkyl, alkenyl, alkynyl, cycloalkyl, alkylcycloalkyl, aryl, alkylaryl, heterocyclyl, alkylheterocyclyl, heteroaryl and alkylheteroaryl; said alkyl, haloalkyl, alkenyl, alkynyl, cycloalkyl, alkylcycloalkyl, aryl, alkylaryl, heterocyclyl, alkylheterocyclyl, heteroaryl and alkylheteroaryl are optionally substituted with $R^b$;

$R^b$ at each occurrence is selected from halogen, nitro, —CN, hydroxy, alkoxy, —COOH, —$NH_2$ and alkyl;
Y is selected from —($CH_2$)—N($R_4$)—, —N($R_4$)—, —N($R_4$)CON($R_5$)—, —N($R_4$)CSN($R_5$)—, —$NR_4C$ (O)—, —N(R$_4$)(C=NR$_4$)N(R$_5$)—, —CON(R$_4$)—, —NR$_4$SO$_2$— and —SO$_2$NR$_4$—;
U is selected from

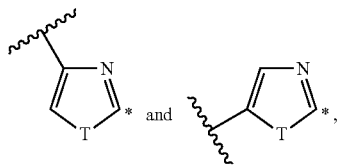

wherein T is —O— or —S—;
V is selected from —CONR$_4$—, —CSNR$_4$—, —C(O), —C(S)—, —COC(R$_4$)(R$_5$) and —SO$_2$NR$_4$;
R$_3$ is selected from —COOR$_p$, —CONR$_p$R$_q$, —CONR$_p$SO$_2$R$_q$ and a carboxylic acid isostere selected from tetrazol-5-yl, 5-trifluoromethyl-1,2,4-triazol-3-yl, 5-(methylsulfonyl)-1,2,4-triazol-3-yl and 2,5-dihydro-5-oxo-1,2,4-oxadiazol-3-yl;
R$_1$, R$_2$, R$_4$ and R$_5$ at each occurence are independently selected from H and unsubstituted or substituted alkyl, wherein substituted alkyl is substituted with substituents selected from R$^a$;
R$_p$ and R$_q$ are independently selected from H, unsubstituted or substituted alkyl, unsubstituted or substituted aryl, unsubstituted or substituted heterocyclyl, or unsubstituted or substituted heteroaryl, wherein each of substituted alkyl, aryl, heterocycle and heteroaryl is substituted with one or more substituents selected from R$^a$;
or R$_1$ and R$_2$ together with the carbon to which they are attached form a three- to six-membered carbocyclic ring, wherein the ring may be optionally substituted with one or more substituents selected from R$^a$;
m is an integer from 0 to 2;
n is an integer from 1 to 2;
* indicates the point of attachment to —V— and

indicates the point of attachment to phenyl ring; or
a stereoisomer, tautomer or a pharmaceutically acceptable salt thereof.

2. A compound of formula (I) according to claim 1,

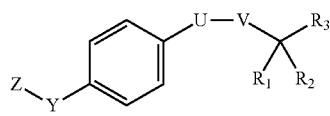

(I)

wherein,
Z is selected from unsubstituted or substituted alkylcycloalkyl, unsubstituted or substituted cycloalkyl, unsubstituted or substituted aryl, unsubstituted or substituted heteroaryl and unsubstituted or substituted heterocycle, wherein each of substituted alkylcycloalkyl, cycloalkyl, aryl, heteroaryl and heterocycle is substituted with one or more substituents selected from R$^a$;
R$^a$ at each occurrence is selected from halogen, nitro, —CN, —OR$_x$, —S(=O)$_m$R$_x$, —S(=O)$_n$NR$_1$R$_2$,
—NR$_x$R$_y$, —NR$_x$COR$_y$, —NR$_x$SOR$_y$, —NR$_x$SO$_2$R$_y$, —NR$_x$CONR$_x$R$_y$, —COOR$_x$, —CONR$_x$R$_y$, —(CR$_x$R$_y$)$_n$—OR$_x$, alkyl, haloalkyl, aryl and heteroaryl; wherein R$_x$ and R$_y$ are independently selected from H and alkyl; wherein alkyl is optionally substituted with one or more halogen or cyano groups;
Y is selected from —(CH$_2$)—N(R$_4$)—, —N(R$_4$)—, —N(R$_4$)CON(R$_5$)—, —NR$_4$C(O)—, —CON(R$_4$)—, —NR$_4$SO$_2$— and —SO$_2$NR$_4$—;
U is selected from

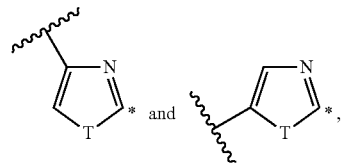

wherein T is —O— or —S—;
V is —CONR$_4$—;
R$_1$, R$_2$, R$_4$ and R$_5$ at each occurrence are independently selected from H and unsubstituted alkyl;
R$_3$ is selected from —COOR$_p$ or a carboxylic acid isostere selected from tetrazol-5-yl, 5-trifluoromethyl-1,2,4-triazol-3-yl, 5-(methylsulfonyl)-1,2,4-triazol-3-yl and 2,5-dihydro-5-oxo-1,2,4-oxadiazol-3-yl; wherein R$_p$ is selected from H, unsubstituted or substituted alkyl, unsubstituted or substituted aryl, unsubstituted or substituted heterocyclyl, or unsubstituted or substituted heteroaryl, wherein each of substituted alkyl, aryl, heterocycle and heteroaryl is substituted with one or more substituents selected from R$^a$;
m is an integer from 0 to 2;
n is an integer from 1 to 2;
* indicates the point of attachment to —V— and

indicates the point of attachment to phenyl ring; or
a stereoisomer, tautomer or a pharmaceutically acceptable salt thereof.

3. The compound according to claim 1, wherein Z is unsubstituted or substituted alkylcycloalkyl.

4. The compound according to claim 3, wherein Z is ethylcyclohexyl.

5. The compound according to claim 1, wherein Z is unsubstituted or substituted cycloalkyl.

6. The compound according to claim 5, wherein Z is cycloalkyl substituted with one or more halogen.

7. The compound according to claim 1, wherein Z is unsubstituted or substituted aryl.

8. The compound according to claim 7, wherein Z is unsubstituted or substituted phenyl.

9. The compound according to claim 8, wherein Z is phenyl substituted with one or more groups selected from haloalkyl, halogen, aryl, —OR$_x$ and alkyl, wherein alkyl is optionally substituted with one or more halogen or cyano groups and R$_x$ is aryl.

10. The compound according to claim 1, wherein Z is unsubstituted or substituted heteroaryl.

11. The compound according to claim 10, wherein Z is heteroaryl substituted with alkyl or halogen.

12. The compound according to claim 11, wherein Z is selected from unsubstituted or substituted benzothiazolyl or unsubstituted or substituted pyridyl, wherein the substituent is fluoro or alkyl.

13. The compound according to claim 1, wherein Y is selected from —N($R_4$)—, —N($R_4$)CON($R_5$)—, —$NR_4$C(O)—, —($CH_2$)—N($R_4$)—, —CON($R_4$)— and —$SO_2NR_4$—, wherein $R_4$ and $R_5$ are independently selected from H and unsubstituted alkyl.

14. The compound according to claim 1, wherein Y is selected from —NH—, —NHCONH—, —$CH_2$—N($CH_2$-Phenyl)-, —$CH_2$—NH—, —CONH— and —$SO_2$NH—.

15. The compound according to claim 1, wherein V is —$CONR_4$—, wherein $R_4$ is selected from H and unsubstituted alkyl.

16. The compound according to claim 15, wherein V is selected from —CONH— and —CON($CH_3$)—.

17. The compound according to claim 1, wherein $R_1$ and $R_2$ are independently selected from H and substituted or unsubstituted alkyl.

18. The compound according to claim 17, wherein $R_1$ and $R_2$ are independently selected from H and isopropyl.

19. The compound according to claim 1 or claim 2, wherein $R_3$ is —$COOR_p$, wherein $R_p$ is H or alkyl.

20. The compound according to claim 19, wherein $R_3$ is selected from —COOH and —$COOCH_3$.

21. A compound according to claim 1, selected from:
Methyl 3-methyl-2-(5-(4-(3-(3-(trifluoromethyl)phenyl)ureido)phenyl)oxazole-2-carboxamido)butanoate,
3-Methyl-2-(5-(4-(3-(3-(trifluoromethyl)phenyl)ureido)phenyl)oxazole-2-carboxamido) butanoic acid,
Methyl 2-(5-(4-(3-(2-chlorophenyl)ureido)phenyl)oxazole-2-carboxamido)-3-methylbutanoate,
2-(5-(4-(3-(2-Chlorophenyl)ureido)phenyl)oxazole-2-carboxamido)-3-methylbutanoic acid,
Methyl 2-(5-(4-(3-(3,4-dimethylphenyl)ureido)phenyl)oxazole-2-carboxamido)-3-methylbutanoate,
2-(5-(4-(3-(3,4-dimethylphenyl)ureido)phenyl)oxazole-2-carboxamido)-3-methylbutanoic acid,
Methyl 2-(5-(4-(3-(4-chloro-2-phenoxyphenyl)ureido)phenyl)oxazole-2-carboxamido)-3-methylbutanoate,
2-(5-(4-(3-(4-chloro-2-phenoxyphenyl)ureido)phenyl)oxazole-2-carboxamido)-3-methylbutanoic acid,
Methyl 3-methyl-2-(5-(4-(3-(3-(trifluoromethyl)phenyl)ureido)phenyl)thiazole-2-carboxamido)butanoate,
3-methyl-2-(5-(4-(3-(3-(trifluoromethyl)phenyl)ureido)phenyl)thiazole-2-carboxamido)butanoic acid,
Methyl 2-(5-(4-(3-(2-chlorophenyl)ureido)phenyl)thiazole-2-carboxamido)-3-methylbutanoate,
2-(5-(4-(3-(2-Chlorophenyl)ureido)phenyl)thiazole-2-carboxamido)-3-methylbutanoic acid,
Methyl 2-(5-(4-(3-(3,4-dimethylphenyl)ureido)phenyl)oxazole-2-carboxamido)-3-methylbutanoate,
2-(5-(4-(3-(3,4-dimethylphenyl)ureido)phenyl)oxazole-2-carboxamido)-3-methylbutanoic acid,
Methyl 3-methyl-2-(5-(4-(3-(2-phenoxyphenyl)ureido)phenyl)thiazole-2-carboxamido)butanoate,
3-methyl-2-(5-(4-(3-(2-phenoxyphenyl)ureido)phenyl)thiazole-2-carboxamido)butanoic acid,
Methyl 2-(5-(4-(3-(4-chloro-2-phenoxyphenyl)ureido)phenyl)thiazole-2-carboxamido)-3-methylbutanoate,
2-(5-(4-(3-(4-chloro-2-phenoxyphenyl)ureido)phenyl)thiazole-2-carboxamido)-3-methylbutanoic acid,
Ethyl 2-(5-(4-(6-fluorobenzo[d]thiazol-2-ylamino)phenyl)thiazole-2-carboxamido)-3-methylbutanoate,
2-(5-(4-(6-fluorobenzo[d]thiazol-2-ylamino)phenyl)thiazole-2-carboxamido)-3-methylbutanoic acid,
Methyl 2-(5-(4-(4-tert-butylbenzamido)phenyl)thiazole-2-carboxamido)-3-methylbutanoate,
2-(5-(4-(4-tert-butylbenzamido)phenyl)thiazole-2-carboxamido)-3-methylbutanoic acid,
Methyl 2-(4-(4-(3-(2-chlorophenyl)ureido)phenyl)thiazole-2-carboxamido)-3-methylbutanoate,
2-(4-(4-(3-(2-Chlorophenyl)ureido)phenyl)thiazole-2-carboxamido)-3-methylbutanoic acid,
Methyl 2-(4-(4-(6-fluorobenzo[d]thiazol-2-ylamino)phenyl)thiazole-2-carboxamido)-3-methylbutanoate,
2-(4-(4-(6-fluorobenzo[d]thiazol-2-ylamino)phenyl)thiazole-2-carboxamido)-3-methylbutanoic acid,
Methyl 2-(4-(4-(4-tert-butylbenzamido)phenyl)thiazole-2-carboxamido)-3-methylbutanoate,
2-(4-(4-(4-tert-butylbenzamido)phenyl)thiazole-2-carboxamido)-3-methylbutanoic acid,
Methyl-3-methyl-2-(4-(4-(3-(4-(trifluoromethyl)phenyl)ureido)phenyl)thiazole-2-carboxamido)butanoate,
3-methyl-2-(4-(4-(3-(4-(trifluoromethyl)phenyl)ureido)phenyl)thiazole-2-carboxamido)butanoic acid,
Methyl 2-(4-(4-(3-(3,4-dimethylphenyl)ureido)phenyl)thiazole-2-carboxamido)-3-methylbutanoate,
2-(4-(4-(3-(3,4-Dimethylphenyl)ureido)phenyl)thiazole-2-carboxamido)-3-methylbutanoic acid,
Methyl 2-(4-(4-(3-(4-chloro-2-phenoxyphenyl)ureido)phenyl)thiazole-2-carboxamido)-3-methylbutanoate,
2-(4-(4-(3-(4-chloro-2-phenoxyphenyl)ureido)phenyl)thiazole-2-carboxamido)-3-methylbutanoic acid,
Methyl 2-(4-(4-biphenyl-4-ylcarboxamidophenyl)thiazole-2-carboxamido)-3-methylbutanoate,
2-(4-(4-Biphenyl-4-ylcarboxamidophenyl)thiazole-2-carboxamido)-3-methylbutanoic acid,
Methyl 3-methyl-2-(4-(4-(4-pentylbenzamido)phenyl)thiazole-2-carboxamido)butanoate,
3-Methyl-2-(4-(4-(4-pentylbenzamido)phenyl)thiazole-2-carboxamido) butanoic acid,
Methyl 3-methyl-2-(N-methyl-5-(4-(4-pentylbenzamido)phenyl)thiazole-2-carboxamido)butanoate,
3-Methyl-2-(N-methyl-5-(4-(4-pentylbenzamido)phenyl)thiazole-2-carboxamido) butanoic acid,
Methyl 2-(5-(4-biphenyl-4-ylcarboxamidophenyl)-N-methylthiazole-2-carboxamido)-3-methylbutanoate,
2-(5-(4-Biphenyl-4-ylcarboxamidophenyl)-N-methylthiazole-2-carboxamido)-3-methylbutanoic acid,
Methyl 2-(5-(4-(4-tert-butylbenzamido)phenyl)-N-methylthiazole-2-carboxamido)-3-methylbutanoate,
2-(5-(4-(4-tert-Butylbenzamido)phenyl)-N-methylthiazole-2-carboxamido)-3-methylbutanoic acid,
Methyl 2-(4-(4-(2,4-dichlor)phenylsulfonamido)phenyl)thiazole-2-carboxamido)-3-methylbutanoate,
2-(4-(4-(2,4-Dichlorophenylsulfonamido)phenyl)thiazole-2-carboxamido)-3-methylbutanoic acid,
Methyl 2-(5-(4-biphenyl-4-ylcarboxamidophenyl)thiazole-2-carboxamido)-3-methylbutanoate,
2-(5-(4-biphenyl-4-ylcarboxamidophenyl)thiazole-2-carboxamido)-3-methylbutanoic acid,
Methyl 2-(5-(4-(3-cyclohexylpropanamido)phenyl)thiazole-2-carboxamido)-3-methylbutanoate,
2-(5-(4-(3-cyclohexylpropanamido)phenyl)thiazole-2-carboxamido)-3-methylbutanoic acid,
Methyl 2-(5-(4-(2,3-dihydro-1H-indene-2-carboxamido)phenyl)thiazole-2-carboxamido)-3-methylbutanoate,
2-(5-(4-(2,3-dihydro-1H-indene-2-carboxamido)phenyl)thiazole-2-carboxamido)-3-methylbutanoic acid, Methyl 2-(5-(4-(4,4-difluorocyclohexanecarboxamido) phenyl)thiazole-2-carboxamido)-3-methylbutanoate,
2-(5-(4-(4,4-difluorocyclohexanecarboxamido)phenyl) thiazole-2-carboxamido)-3-methylbutanoic acid,
(S)-methyl 2-(5-(4-(3-(2,3-dihydro-1H-inden-5-yl)ureido)phenyl)oxazole-2-carboxamido)-3-methylbutanoate,
(S)-2-(5-(4-(3-(2,3-dihydro-1H-inden-5-yl)ureido)phenyl)oxazole-2-carboxamido)-3-methylbutanoic acid,
(S)-Methyl 2-(5-(4-(3-(4-chlorophenyl)ureido)phenyl)oxazole-2-carboxamido)-3-methylbutanoate,
(S)-2-(5-(4-(3-(4-chlorophenyl)ureido)phenyl)oxazole-2-carboxamido)-3-methylbutanoic acid,
(S)-methyl 2-(5-(4-(3-(3-chlorophenyl)ureido)phenyl)oxazole-2-carboxamido)-3-methylbutanoate,
(S)-2-(5-(4-(3-(3-chlorophenyl)ureido)phenyl)oxazole-2-carboxamido)-3-methylbutanoic acid,
(S)-methyl 2-(5-(4-(3-(2-chloro-4-(trifluoromethyl)phenyl)ureido)phenyl)oxazole-2-carboxamido)-3-methylbutanoate,
(S)-2-(5-(4-(3-(2-chloro-4-(trifluoromethyl)phenyl)ureido)phenyl)oxazole-2-carboxamido)-3-methylbutanoic acid,
(S)-methyl 2-(5-(4-(3-(4-chloro-2-fluorophenyl)ureido) phenyl)oxazole-2-carboxamido)-3-methylbutanoate,
(S)-2-(5-(4-(3-(4-chloro-2-fluorophenyl)ureido)phenyl) oxazole-2-carboxamido)-3-methylbutanoic acid,
(S)-Methyl 2-(5-(4-(3-(2,3-dihydro-1H-inden-5-yl)ureido)phenyl)thiazole-2-carboxamido)-3-methylbutanoate,
(S)-2-(5-(4-(3-(2,3-dihydro-1H-inden-5-yl)ureido)phenyl)thiazole-2-carboxamido)-3-methylbutanoic acid,
(S)-methyl 2-(5-(4-(3-(4-chlorophenyl)ureido)phenyl) thiazole-2-carboxamido)-3-methylbutanoate,
(S)-2-(5-(4-(3-(4-chlorophenyl)ureido)phenyl)thiazole-2-carboxamido)-3-methylbutanoic acid,
(S)-Methyl 2-(5-(4-(3-(3-chlorophenyl)ureido)phenyl) thiazole-2-carboxamido)-3-methylbutanoate,
(S)-2-(5-(4-(3-(3-chlorophenyl)ureido)phenyl)thiazole-2-carboxamido)-3-methylbutanoic acid,
(S)-methyl 2-(5-(4-(3-(2-chloro-4-(trifluoromethyl)phenyl)ureido)phenyl)thiazole-2-carboxamido)-3-methylbutanoate,
(S)-2-(5-(4-(3-(2-chloro-4-(trifluoromethyl)phenyl)ureido)phenyl)thiazole-2-carboxamido)-3-methylbutanoic acid,
(S)-methyl 2-(5-(4-(3-(4-chloro-2-fluorophenyl)ureido) phenyl)thiazole-2-carboxamido)-3-methylbutanoate,
(S)-2-(5-(4-(3-(4-chloro-2-fluorophenyl)ureido)phenyl) thiazole-2-carboxamido)-3-methylbutanoic acid,
(S)-Methyl 2-(4-(4-(3-(4-chlorophenyl)ureido)phenyl) thiazole-2-carboxamido)-3-methylbutanoate,
(S)-2-(4-(4-(3-(4-Chlorophenyl)ureido)phenyl)thiazole-2-carboxamido)-3-methylbutanoic acid,
(S)-Methyl 2-(4-(4-(3-(2,3-dihydro-1H-inden-5-yl)ureido)phenyl)thiazole-2-carboxamido)-3-methylbutanoate,
(S)-2-(4-(4-(3-(2,3-dihydro-1H-inden-5-yl)ureido)phenyl)thiazole-2-carboxamido)-3-methy)butanoic acid,
(S)-methyl 2-(4-(4-(3-(3-chlorophenyl)ureido)phenyl) thiazole-2-carboxamido)-3-methylbutanoate,
(S)-2-(4-(4-(3-(3-chlorophenyl)ureido)phenyl)thiazole-2-carboxamido)-3-methylbutanoic acid,
(S)-Methyl 2-(4-(4-(3-(2-chloro-4-(trifluoromethyl)phenyl))ureido)phenyl)thiazole-2-carboxamido)-3-methylbutanoate,
(S)-2-(4-(4-(3-(2-chloro-4-(trifluoromethyl)phenyl)ureido)phenyl)thiazole-2-carboxamido)-3-methylbutanoic acid,
(S)-Methyl 2-(4-(4-(3-(4-chloro-2-fluorophenyl)ureido) phenyl)thiazole-2-carboxamido)-3-methylbutanoate,
(S)-2-(4-(4-(3-(4-chloro-2-fluorophenyl)ureido)phenyl) thiazole-2-carboxamido)-3-methylbutanoic acid,
Methyl 2-(5-(4-(4-(2-cyanopropan-2-yl)benzamido)phenyl)thiazole-2-carboxamido)-3-methylbutanoate,
2-(5-(4-(4-(2-cyanopropan-2-yl)benzamido)phenyl)thiazole-2-carboxamido)-3-methylbutanoic acid,
Methyl 2-(5-(4-(4-(3-cyanopentan-3-yl)benzamido)phenyl)thiazole-2-carboxamido)-3-methylbutanoate,
2-(5-(4-(4-(3-cyanopentan-3-yl)benzamido)phenyl)thiazole-2-carboxamido)-3-methylbutanoic acid,
Methyl 2-(5-(4-(benzylamino)phenyl)thiazole-2-carboxamido)-3-methylbutanoate,
Methyl 2-(5-(4-((4-fluorobenzyl)amino)phenyl)thiazole-2-carboxamido)-3-methylbutanoate,
2-(5-(4-((4-Fluorobenzyl)amino)phenyl)thiazole-2-carboxamido)-3-methylbutanoic acid,
Methyl 2-(5-(4-(dibenzylamino)phenyl)thiazole-2-carboxamido)-3-methylbutanoate,
2-(5-(4-(dibenzylamino)phenyl)thiazole-2-carboxamido)-3-methylbutanoic acid,
Methyl 2-(5-(4-(5-butylpicolinamido)phenyl)thiazole-2-carboxamido)-3-methylbutanoate, and
2-(5-(4-(5-butylpicolinamido)phenyl)thiazole-2-carboxamido)-3-methylbutanoic acid;
or a stereoisomer, tautomer or pharmaceutically acceptable salt or solvate thereof.

22. A pharmaceutical composition, comprising a therapeutically effective amount of a compound of formula (I) according to claim 1 or a pharmaceutically acceptable salt thereof, together with a pharmaceutically acceptable excipient or carrier.

23. A method for the treatment of diseases mediated by diacylglycerol acyltransferase-1 (DGAT-1), comprising administering to a mammal in need thereof a therapeutically effective amount of a compound of formula (I) according to claim 1, or a pharmaceutically acceptable salt thereof, wherein the DGAT-1 mediated disease is obesity or an obesity related disorder wherein the obesity related disorder is selected from diabetes mellitus, insulin resistance, impaired glucose tolerance, diabetic neuropathy, diabetic nephropathy, diabetic retinopathy, hypercholesterolemia, hypertriglyceridemia, hyperlipidemia, steatosis, cardiovascular diseases selected from hypertension; cardiac failure; cardiomyopathy; myocardial ischemia; myocardial infarction; atherosclerosis, and acne wherein the treatment is alleviating, slowing the progression of, or attenuating the DGAT-1 mediated disease.

24. A process for the preparation of a compound of formula (10)

(10)

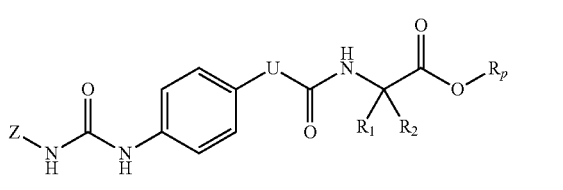

69 which comprises the steps of:
reacting a compound of formula (9)

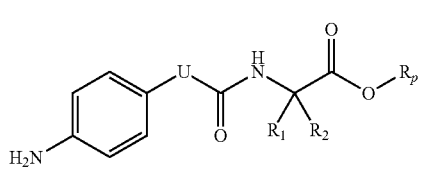
(9)

with an isocyanate of formula Z—NCO in tetrahydrofuran as a solvent,
wherein, Z, U, $R_1$, and $R_2$ are as defined in claim 1 or claim 2 and $R_p$ is alkyl;
optionally converting the resulting ester to corresponding acid by alkaline hydrolysis;
optionally converting the resultant acid into a pharmaceutically acceptable salt.

25. A process for the preparation of a compound of formula (12)

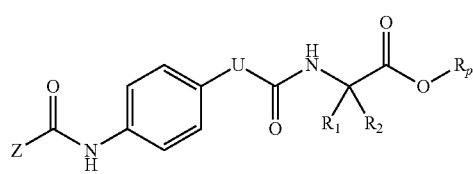
(12)

comprising the steps of:
reacting a compound of formula (9)

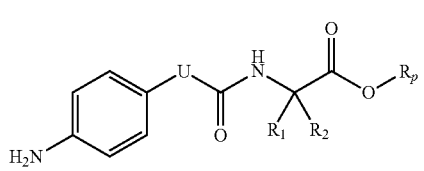
(9)

with a compound of formula Z—COCl in DCM as a solvent and in presence of pyridine as a base or with a compound of formula Z—COOMe, in presence of trimethylaluminum and toluene as the solvent, to obtain the compound of formula (12), wherein, Z, U, $R_1$, and $R_2$ are as defined in claim 1 or claim 2 and $R_p$ is alkyl; optionally converting the resulting ester to corresponding acid by alkaline hydrolysis; optionally converting the resultant acid into a pharmaceutically acceptable salt.

26. A process for the preparation of a compound of formula (14)

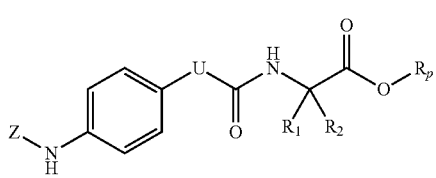
(14)

70 comprising the steps of:
reacting a compound of formula (9)

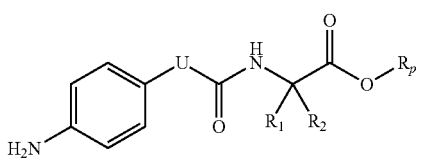
(9)

with a compound of formula Z—Cl in n-butanol as a solvent, in presence of hydrochloric acid in dioxane or
with a compound of formula Z—Br in dichloromethane (DCM) as a solvent in presence of triethylamine as a base, to obtain the compound of formula (14), wherein, Z, U, $R_1$, and $R_2$ are as defined in claim 1 or claim 2 and $R_p$ is alkyl; optionally converting the resulting ester to corresponding acid by alkaline hydrolysis; optionally converting the resultant acid into a pharmaceutically acceptable salt.

27. A process for the preparation of a compound of formula (14a)

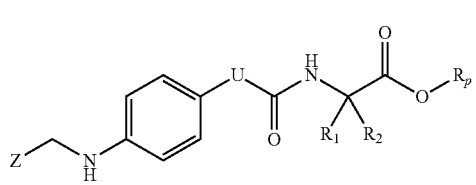
(14a)

comprising the steps of:
reacting a compound of formula (9)

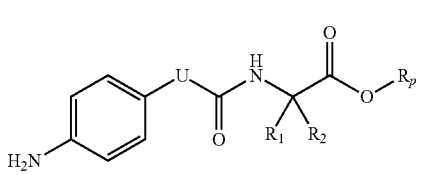
(9)

with a compound of formula Z—$CH_2$Cl or Z—$CH_2$Br in acetone as a solvent, in presence of potassium carbonate as a base to obtain the compound of formula (14a), wherein, Z, U, $R_1$, and $R_2$ are as defined in claim 1 or claim 2 and $R_p$ is alkyl; optionally converting the resulting ester to the corresponding acid by alkaline hydrolysis; optionally converting the resultant acid into a pharmaceutically acceptable salt.

28. A process for the preparation of a compound of formula (18)

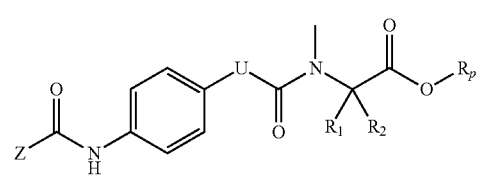
(18)

comprising the steps of:
reacting a compound of formula (17)

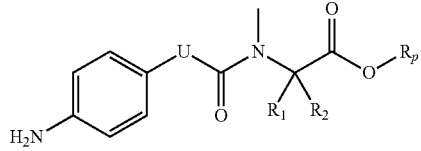
(17)

with a compound of formula Z—COCl,
wherein, Z, U, $R_1$, and $R_2$ are as defined in claim 1 or claim 2 and $R_p$ is alkyl;
optionally converting the resulting ester to the corresponding acid by alkaline hydrolysis;
optionally converting the resultant acid into a pharmaceutically acceptable salt.

29. A process for the preparation of a compound of formula (20)

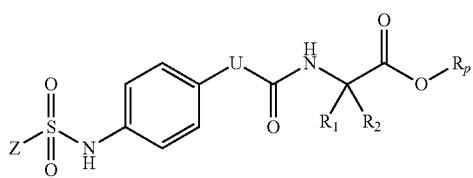
(20)

comprising the steps of:

reacting a compound of formula (9)

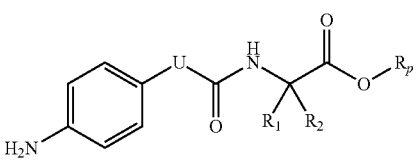
(9)

with a compound of formula Z—$SO_2Cl$ in DCM as a solvent in presence of pyridine as a base, wherein, Z, U, $R_1$, and $R_2$ are as defined in claim 1 or claim 2 and $R_p$ is alkyl; optionally converting the resulting ester to the corresponding acid by alkaline hydrolysis; optionally converting the resultant acid into a pharmaceutically acceptable salt.

\* \* \* \* \*